(12) United States Patent
Hohsaka

(10) Patent No.: US 8,372,960 B2
(45) Date of Patent: Feb. 12, 2013

(54) MUTANT TRNA FOR INTRODUCING UNNATURAL AMINO ACID INTO PROTEIN

(75) Inventor: Takahiro Hohsaka, Ishikawa (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 1293 days.

(21) Appl. No.: 12/084,967

(22) PCT Filed: Nov. 14, 2006

(86) PCT No.: PCT/JP2006/323064
§ 371 (c)(1),
(2), (4) Date: May 14, 2008

(87) PCT Pub. No.: WO2007/055429
PCT Pub. Date: May 18, 2007

(65) Prior Publication Data
US 2011/0224411 A1    Sep. 15, 2011

(30) Foreign Application Priority Data

Nov. 14, 2005  (JP) ................................. 2005-329115

(51) Int. Cl.
*C07K 1/107* (2006.01)
*C07H 21/02* (2006.01)

(52) U.S. Cl. ...................... 536/23.1; 514/44 A; 530/409

(58) Field of Classification Search ......................... None
See application file for complete search history.

(56) References Cited

PUBLICATIONS

Turacatti et al Probing the Structure and Function of the Tachykinin Neurokinin-2 Receptor through Biosynthetic Incorporation of Fluorescent Amino Acids at Specific Sites.*

Probing the Structure and Function of the Tachykinin Neurokinin-2 receptor through Biosynthetic Incorporation of Fluorescent Amino Acids at Specific Sites JBC 1996, vol. 271, No. 33, pp. 19991-19998.*

Yamao, F. et al., "UGA is read as tryptophan in *Mycoplasma capricolum*", Proc. Natl. Acad. Sci. USA, vol. 82, pp. 2306-2309, (1985).

Anderson, J.C. et al., "An expanded genetic code with a functional quadruplet codon", Proc. Natl. Acad. Sci. USA, vol. 101 No. 20, pp. 7566-7571, (2004).

Santoro, S.W. et al., "An archaebacteria-derived glutamyl-Trna synthetase and tRNA pair for unnatural amino acid mutagenesis of proteins in *Escherichia coli*", Nucleic Acids Research, vol. 31, No. 23, pp. 6700-6709, (2003).

Hohsaka, T. et al. "Efficient Incorporation of Nonnatural Amino Acids with Large Aromatic Groups into Streptavidin in In Vitro Protein Synthesizing Systems", Journal, American Chemical Society, vol. 121 pp. 34-40, (1999).

Kajihara, D. et al., "2 Shurui no Keiko Kyoshiki Aminosan o Bui Tokuiteki ni Donyu shita Tanpaushitsu no Sakusei to FRET Bunsekl", The Chemical Society of Japan Koen Yokoshu, vol. 85, p. 1213, (2005) (with partial English translation).

* cited by examiner

*Primary Examiner* — Kagnew H Gebreyesus
(74) *Attorney, Agent, or Firm* — Oblon, Spivak, McClelland, Maier & Neustadt, L.L.P.

(57) ABSTRACT

It is an objective of the present invention to provide tRNA that has CUA or CCCG as an anticodon and is aminoacylated with an unnatural amino acid, such tRNA being capable of efficiently introducing an unnatural amino acid into a protein without competing with a termination factor. Such tRNA is a mutant tRNA for tryptophan which has G at the 5' end, C as a base pairing with the G at the 5' end, and A as a base next to the C on the 3' side, such tRNA being a mutant tRNA which pairs with a stop codon and has CUA as an anticodon or a mutant tRNA which pairs with a stop codon or a 4-base codon has CUA or CCCG as an anticodon, into which a single base has been inserted just before the CCA sequence at the 3' end.

11 Claims, 52 Drawing Sheets

Fig. 3A

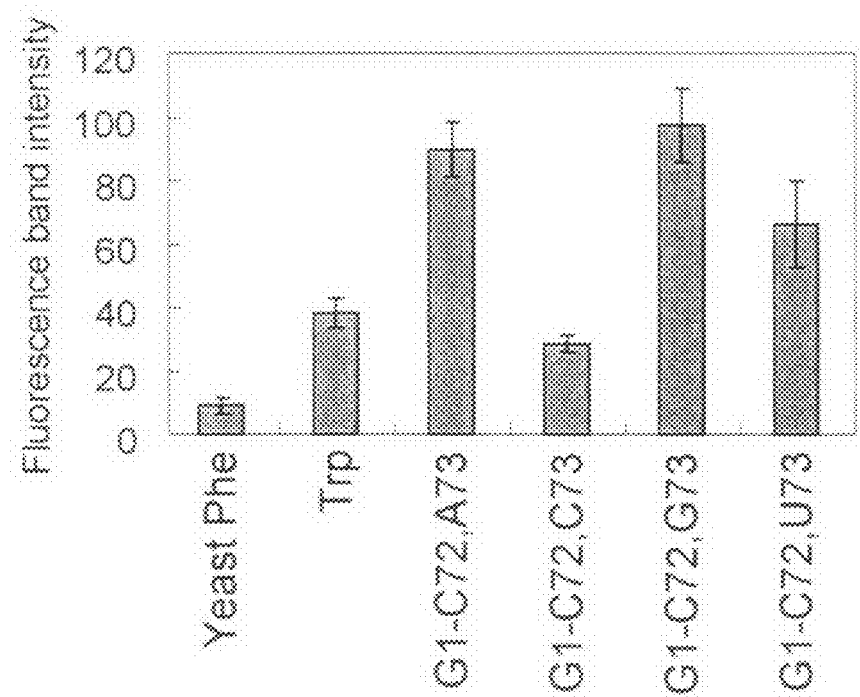

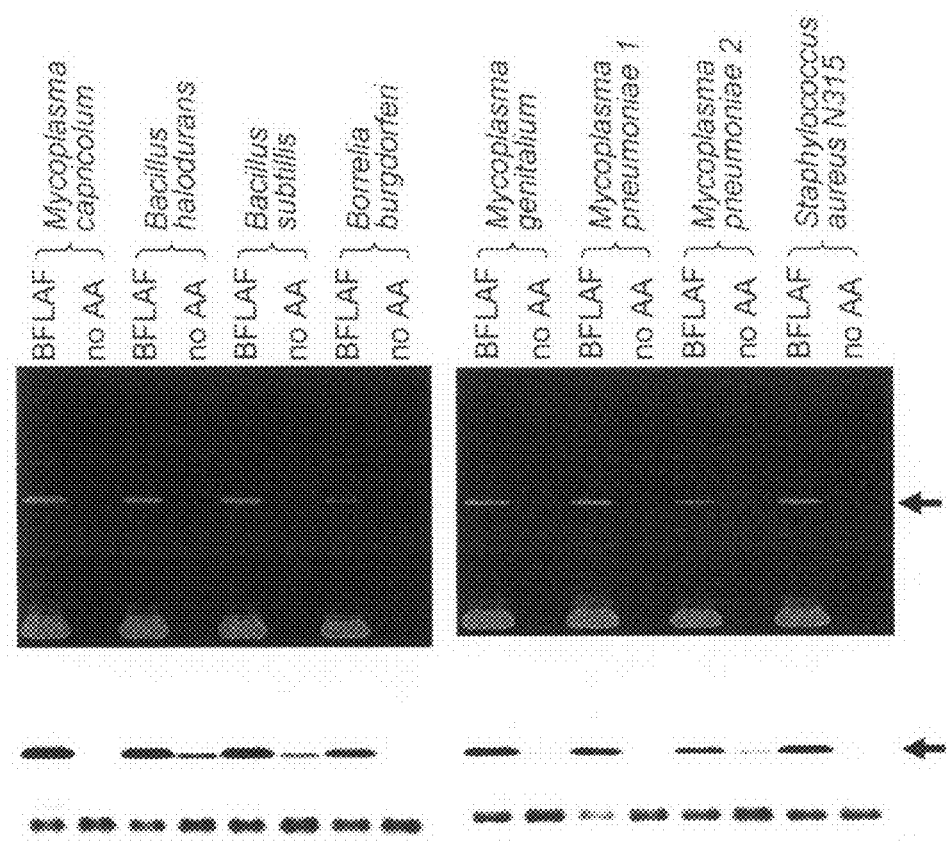

Type of codon incorporated into the 2nd base of streptavidin

CGGG      UAG tRNA for yeast Phe (anticodon: CCCG)

Mutant tRNA for *Mycoplasma capricolum* Trp (anticodon: CUA)

Fig. 17

Mutant tRNA for
Mycoplasma capricolum tryptophan
(normal)

73.1A
73.1C
73.1G
73.1U

SEQUENCE LISTING

<160> NUMBER OF SEQ ID NOS: 41

<210> SEQ ID NO 1
<211> LENGTH: 75
<212> TYPE: RNA
<213> ORGANISM: Mycoplasma capricolum

<400> SEQUENCE: 1
gggagaguag uucaauggua gaacgucggu cucuaaaacc gagcguugag gguucgauuc 60
cuuucucucc cacca 75

<210> SEQ ID NO 2
<211> LENGTH: 76
<212> TYPE: RNA
<213> ORGANISM: Escherichia coli

<400> SEQUENCE: 2
gggggcguag uucaauuggu agagcaccgg ucucuaaaac cgggguguugg gaguucgagu 60 cucuccgccc ccacca 76

<210> SEQ ID NO 3
<211> LENGTH: 76
<212> TYPE: RNA
<213> ORGANISM: Aquifex aeolicus

<400> SEQUENCE: 3
ggggcuguag cucaauuggc agagcgcggg acucuaaauc ccgugggugg ggguucgagu 60
ccucccagcc ccacca 76

<210> SEQ ID NO 4
<211> LENGTH: 74
<212> TYPE: RNA
<213> ORGANISM: Bacillus halodurans

<400> SEQUENCE: 4
gggggcauag uguaacggua gaacagaggu cucuaaaacc uccggugugg guucgauucc 60
uacugccccc acca 74

<210> SEQ ID NO 5
<211> LENGTH: 74
<212> TYPE: RNA
<213> ORGANISM: Bacillus subtilis

<400> SEQUENCE: 5
gggggcauag uuuaacggua gaacagaggu cucuaaaacc uccggugugg guucgauucc 60
uacugccccc acca 74

<210> SEQ ID NO 6
<211> LENGTH: 77
<212> TYPE: RNA
<213> ORGANISM: Borrelia burgdorferi

<400> SEQUENCE: 6 gggggguguag uucaauuugg uagagcaucg gucucuaaaa ccgaaaguug uagguucaaa 60
uccuuccacc cccacca 77

<210> SEQ ID NO 7
<211> LENGTH: 77
<212> TYPE: RNA

```
<213> ORGANISM: Buchnera sp

<400> SEQUENCE: 7
ggggguguag uucaauuugg uagagcaucg gucucuaaaa ccgaaaguug uagguucaaa      60
uccuuccacc cccacca                                                    77

<210> SEQ ID NO 8
<211> LENGTH: 76
<212> TYPE: RNA
<213> ORGANISM: Campylobacter jejuni

<400> SEQUENCE: 8
ggggcaauag cuccaacggu agagcgccgg auucuaaauc cgaugguugg ggguucgaau      60
cccucuugcc ccacca                                                     76

<210> SEQ ID NO 9
<211> LENGTH: 76
<212> TYPE: RNA
<213> ORGANISM: Caulobacter crescentus

<400> SEQUENCE: 9
gggaguguag cucagcuggu agagcaucgg ucucuaaaac cgagggccgg ggguucgagu      60
cccuccacuc ccacca                                                     76

<210> SEQ ID NO 10
<211> LENGTH: 76
<212> TYPE: RNA
<213> ORGANISM: Chlamydia pneumoniae

<400> SEQUENCE: 10
ggguguguag cuuagcuggu agagcagugg ccucuaaagc cgccggucgg ggguucgauu      60
cccuucgcac ccacca                                                     76

<210> SEQ ID NO 11
<211> LENGTH: 76
<212> TYPE: RNA
<213> ORGANISM: Chlamydia trachomatis
<220> FEATURE:
<223> OTHER INFORMATION: Chlamydia trachomatis D1

<400> SEQUENCE: 11
ggguguguag cuuagauggu agagcagugg ccucuaaagc cgccggucgg ggguucgaau      60
cccuccgcac ucacca                                                     76

<210> SEQ ID NO 12
<211> LENGTH: 75
<212> TYPE: RNA
<213> ORGANISM: Chlamydia trachomatis
<220> FEATURE:
<223> OTHER INFORMATION: Chlamydia trachomatis D2

<400> SEQUENCE: 12
ggguguguag cuuagauggu agagcagugg ccucuaaagc cgccggucgg ggguucgaau      60
cccucuucac cacca                                                      75

<210> SEQ ID NO 13
<211> LENGTH: 76
<212> TYPE: RNA
<213> ORGANISM: Deinococcus radiodurans

<400> SEQUENCE: 13
```

```
ggguucuuag cucaguuggu agagcggcgg ucucuaaaac cguaggucga ggguucaagu    60
ccuucagggc ccacca                                                   76
```

<210> SEQ ID NO 14
<211> LENGTH: 76
<212> TYPE: RNA
<213> ORGANISM: Haemophilus influenzae
<220> FEATURE:
<223> OTHER INFORMATION: Haemophilus influenzae Rd

<400> SEQUENCE: 14

```
gggggcguag uucaauuggu agagcaccgg ucucuaaaac cggguguugg gaguucgagc    60
cucuccgccc ccacca                                                   76
```

<210> SEQ ID NO 15
<211> LENGTH: 76
<212> TYPE: RNA
<213> ORGANISM: Helicobacter pylori

<400> SEQUENCE: 15

```
ggucaguag ucccaauggu agagcgucgg ucucuaaaac cgguuguugg ggguucgagu     60
cccuccuggc ccacca                                                   76
```

<210> SEQ ID NO 16
<211> LENGTH: 76
<212> TYPE: RNA
<213> ORGANISM: Mycobacterium leprae

<400> SEQUENCE: 16

```
gggggcguag cucaacuggc agagcagcgg ucucuaaaac cgcagguugc agguucaaau    60
ccugucgccc ccacca                                                   76
```

<210> SEQ ID NO 17
<211> LENGTH: 76
<212> TYPE: RNA
<213> ORGANISM: Mycobacterium tuberculosis

<400> SEQUENCE: 17

```
gggggcguag cucaacuggc agagcagcgg ucucuaaaac cgcagguugc agguucaagu    60
ccugucgccc ccacca                                                   76
```

<210> SEQ ID NO 18
<211> LENGTH: 74
<212> TYPE: RNA
<213> ORGANISM: Mycoplasma genitalium

<400> SEQUENCE: 18

```
gggggguag uuuaguggua gaacaacagu cucuaaaacu gucugugugg guucgauucc     60
uuccaccccc acca                                                     74
```

<210> SEQ ID NO 19
<211> LENGTH: 74
<212> TYPE: RNA
<213> ORGANISM: Mycoplasma pneumoniae
<220> FEATURE:
<223> OTHER INFORMATION: Mycoplasma pneumoniae 1

<400> SEQUENCE: 19

```
ggggguguag uuuaguggca gaacaacagu cucuaaaacu gucugugugg guucgauucc    60
uuccaccccc acca                                                     74
```

```
<210> SEQ ID NO 20
<211> LENGTH: 75
<212> TYPE: RNA
<213> ORGANISM: Mycoplasma pneumoniae
<220> FEATURE:
<223> OTHER INFORMATION: Mycoplasma pneumoniae 2

<400> SEQUENCE: 20
gggggauuag uucaaaggua gaacaucugu cucuaaaaua gaguguugug gguucgaguc      60
cugcuacccc cacca                                                      75

<210> SEQ ID NO 21
<211> LENGTH: 76
<212> TYPE: RNA
<213> ORGANISM: Neisseria meningitidis
<220> FEATURE:
<223> OTHER INFORMATION: Neisseria meningitidis MC58

<400> SEQUENCE: 21
gggccaauag cucaauuggu agaguaucgg ucucuaaaac cgaggguugg ggguucgaga      60
cccucuuggc ccacca                                                     76

<210> SEQ ID NO 22
<211> LENGTH: 76
<212> TYPE: RNA
<213> ORGANISM: Unknown
<220> FEATURE:
<223> OTHER INFORMATION: Procaryote Trp consensus

<400> SEQUENCE: 22
gggggcguag uucaauuggu agagcagcgg ucucuaaaac cgcagguugg ggguucgagu      60
cccuccgccc ccacca                                                     76

<210> SEQ ID NO 23
<211> LENGTH: 76
<212> TYPE: RNA
<213> ORGANISM: Pseudomonas aeruginosa

<400> SEQUENCE: 23
gggccaguag cucaauuggc agagcggcgg ucucuaaaaa agcagguugg ggguucgauu      60
cccuccuggc ccacca                                                     76

<210> SEQ ID NO 24
<211> LENGTH: 76
<212> TYPE: RNA
<213> ORGANISM: Rickettsia prowazekii

<400> SEQUENCE: 24
gggaguguag cucaauuggu agagcgccgg ucucuaaaac cggagguugc ggguucgauu      60
ccugucgcuc cacca                                                      76

<210> SEQ ID NO 25
<211> LENGTH: 74
<212> TYPE: RNA
<213> ORGANISM: Staphylococcus aureus
<220> FEATURE:
<223> OTHER INFORMATION: Staphylococcus aureus N315

<400> SEQUENCE: 25
gggggcauag uucaacggua gaauagaggu cucuaaaacc uuuggugugg guucgauucc      60 uacugcccc acca                                                        74
```

```
<210> SEQ ID NO 26
<211> LENGTH: 76
<212> TYPE: RNA
<213> ORGANISM: Synechocystis sp.

<400> SEQUENCE: 26
gcguccuuag uucaguuggu agaacgcagg ucucuaaaac cugaugucgg ggguucaagu      60
ccuccagggc gcacca                                                     76

<210> SEQ ID NO 27
<211> LENGTH: 76
<212> TYPE: RNA
<213> ORGANISM: Thermotoga maritima

<400> SEQUENCE: 27
ggggccguag cucaacuggu agagcgccgg ucucuaaaac cggugguugc ggguucgagu      60
ccugccggcc ccacca                                                     76

<210> SEQ ID NO 28
<211> LENGTH: 76
<212> TYPE: RNA
<213> ORGANISM: Treponema pallidum

<400> SEQUENCE: 28
gggucaguag cucuaauggc agagcgucgg ucucuaaaac cgaauguuga agguucgagu      60
ccuuccuggc ccacca                                                     76

<210> SEQ ID NO 29
<211> LENGTH: 76
<212> TYPE: RNA
<213> ORGANISM: Ureaplasma urealyticum

<400> SEQUENCE: 29
gagggauaug uucaauuggu agaacagcag acucuaaauc ugcguguugc ggguucgagu      60
ccuguuaccc ucacca                                                     76

<210> SEQ ID NO 30
<211> LENGTH: 77
<212> TYPE: RNA
<213> ORGANISM: Vibrio cholerae

<400> SEQUENCE: 30
ggggguguag cuccaauugg cagagcagcg gauucuaaau ccgcguguug ggaguucgaa      60
ucucuccacc cccacca                                                    77

<210> SEQ ID NO 31
<211> LENGTH: 76
<212> TYPE: RNA
<213> ORGANISM: Xylella fastidiosa

<400> SEQUENCE: 31
gcgucaguag cucaauuggc agagcagcgg ucucuaaaac cgcagguugg ggguucgagu      60
cccuccuggc gcacca                                                     76

<210> SEQ ID NO 32
<211> LENGTH: 18
<212> TYPE: DNA
<213> ORGANISM: Artificial Sequence
<220> FEATURE:
<223> OTHER INFORMATION: Primer
```

-continued

<400> SEQUENCE: 32
ctaatacgac tcactata                                                     18

<210> SEQ ID NO 33
<211> LENGTH: 546
<212> TYPE: RNA
<213> ORGANISM: Artificial Sequence
<220> FEATURE:
<223> OTHER INFORMATION: Synthetic

<400> SEQUENCE: 33
auggcuagca ugacuggugg acagcaaaug gguaccgaau ccauaugga cccguccaag         60 gacuccaaag cucagguuuc ugcagccgaa gcugguauca cuggcaccug guauaaccaa       120
cuggggucga cuuucauugu gaccgcuggu gcggacggag cucugacugg caccuacgaa       180
ucugcgguug guaacgcaga aucccgcuac guacugacug gccguuauga cucugcaccu       240
gccaccgaug cucuguac cgcucugggc uggacugugg cuuggaaaaa caacuagcgu         300
aaugcgcaca gcgccacuac guggucuggc caauacguug gcggugcuga ggcucguauc       360
aacacucagu ggcuguuaac auccggcacu accgaagcga augcauggaa aucgacacua       420
guaggucaug acaccuuuac caaaguuaag ccuucugcug cuagcauuga ugcugccaag       480
aaagcaggcg uaaacaacgg uaacccucua gacgcuguuc agcaacacca ccaccaccac       540
cacuaa                                                                 546

<210> SEQ ID NO 34
<211> LENGTH: 1190
<212> TYPE: RNA
<213> ORGANISM: Artificial Sequence
<220> FEATURE:
<223> OTHER INFORMATION: Synthetic

<400> SEQUENCE: 34
auggcuagca ugacuggugg acagcaaaug gguacucggg aguaacgaau ucaaaaucga        60
agaagguaaa cugguaaaucu gggauuaacgg cgauaaaggc uauaacgguc ucgcugaagu    120
cgguaagaaa uucgagaaag auaccggaau uaaagucacc guugagcauc cggauaaacu      180
ggaagagaaa uucccacagg uugcggcaac uggcgauggc ccugacauua ucuucgggc       240 acacgaccgc uuugguggcu acgcucaauc uggccguug gcugaaauca cccggacaa       300 agcguuccag gacaagcugu auccguuuac cugggaugcc guacguuaca acggcaagcu      360
gauugcuuac ccgaucgcug uugaagcguu aucgcugauu uauaacaaag aucgcugcc       420 gaacccgcca aaaaccuggg aagagauccc ggcgcuggau aaagaacuga agcgaaagg       480 uaagagcgcg cugauguuca accugcaaga accguacuuc accuggccgc ugauugcugc      540
ugacgggggu uaugcguuca aguaugaaaa cggcaaguac gacauuaaag acguggggcgu     600 ggauaacgcu ggcgcgaaag cgggucgac cuuccugguu gaccgauua aaacaaaca        660 caugaaugca gacaccgauu acuccaucgc agaagcugcc uuuaauaaag gcgaaacagc      720
gaugaccauc aacggcccgu gggcaugguc caacaucgac accagcaaag ugaauuaugg     780 uguaacgguua cugccgaccu ucaagggucua accauccaaa ccguucguug gcgugcugag    840
cgcagguauu aacgccgcca guccgaacaa agagcuggca aaagaguucc ucgaaaacua     900
ucugcugacu gaugaagguc uggaagcggu uaauaaagac aaaccgcugg gugccguagc    960
gcugaagucu uacgaggaag aguuggcgaa agauccacgu auugccgcca cauggaaaa   1020 cgcccagaaa ggugaaauca ugccgaacau cccgcagaug uccgcuuucu gguaugccgu    1080

| | |
|---|---:|
| gcguacugcg gugaucaacg ccgccagcgg ucgucagacu gucgaugaag cccugaaaga | 1140 |
| cgcgcagacu cguaucacca aggggauagcc accaccacca ccaccacuaa | 1190 |

```
<210> SEQ ID NO 35
<211> LENGTH: 1186
<212> TYPE: RNA
<213> ORGANISM: Artificial Sequence
<220> FEATURE:
<223> OTHER INFORMATION: Synthetic

<400> SEQUENCE: 35
```

| | |
|---|---:|
| auggcuagca ugacuggugg acagcaaaug gguacucggg aguaacgaau ucaaaaucga | 60 |
| agaagguaaa cugguaaucu ggauuaacgg cgauaaggc uauaacgguc ucgcugaagu | 120 |
| cgguaagaaa uucgagaaag auaccggaau uaaagucacc guuagcauc cggauaaacu | 180 |
| ggaagagaaa uucccacagg uugcggcaac uggcgauggc ccugacauua ucuucgggc | 240 |
| acacgaccgc uuuggugggu acgcucaauc uggccguug gcugaaauca ccccggacaa | 300 |
| agcguuccag gacaagcugu auccguuuac cugggaugcc guacguuaca acggcaagcu | 360 |
| gauugcuuac ccgaucgcug uugaagcguu aucgcugauu uauaacaaag aucugcugcc | 420 |
| gaacccgcca aaaaccuggg aagagauccc ggcgcuggau aaagaacuga agcgaaagg | 480 |
| uaagagcgcg cugauguuca accugcaaga accguacuuc accugccgc ugauugcugc | 540 |
| ugacgggggu uaugcguuca aguaugaaaa cggcaaguac gacauuaaag acgugggcgu | 600 |
| ggauaacgcu ggcgcgaaag cgggucgac cuuccgguu gaccugauua aaacaaaca | 660 |
| caugaaugca gacaccgauu acuccaucgc agaagcugcc uuuaauaaag gcgaaacagc | 720 |
| gaugaccauc aacggcccgu gggcaugguc caacaucgac accagcaaag ugaauuaugg | 780 |
| uguaacggua cugccgaccu ucaaggguca accauccaaa ccguucguug gcgugcugag | 840 |
| cgcagguauu aacgccgcca guccgaacaa agagcuggca aaagaguucc ucgaaaacua | 900 |
| ucugcugacu gaugaagguc uggaagcggu aauaaagac aaaccgcugg ugccguagc | 960 |
| gcugaagucu uacgaggaag aguuggcgaa agaccacgu auugccgcca cuauggaaaa | 1020 |
| cgcccagaaa ggguaaauca ugccgaacau cccgcagaug uccgcuuucu gguaugccgu | 1080 |
| gcguacugcg gugaucaacg ccgccagcgg ucgucagacu gucgaugaag cccugaaaga | 1140 |
| cgcgcagacu cguaucacca aguagcacca ccaccacac cacuaa | 1186 |

```
<210> SEQ ID NO 36
<211> LENGTH: 501
<212> TYPE: RNA
<213> ORGANISM: Artificial Sequence
<220> FEATURE:
<223> OTHER INFORMATION: Synthetic

<400> SEQUENCE: 36
```

| | |
|---|---:|
| auguagccgu ccaaggacuc caaagcucag guuucugcag ccgaagcugg uaucacuggc | 60 |
| accugguaua ccaacugggg ucgacuuuc auugugaccg cuggugcgga cggagcucug | 120 |
| acuggcaccu acgaaucgc gguugguaac gcagaauccc gcuacguacu gacuggccgu | 180 |
| uaugacucug caccugccac cgauggcucu gguaccgcuc uggcuggac uguggcuugg | 240 |
| aaaacaacu agcguaaugc gcacagcgcc acuacguggu cuggccaaua cguuggcggu | 300 |
| gcugaggcuc guaucaacac ucaguggcug uuaacauccg gcacuaccga agcgaaugca | 360 |
| uggaaaucga cacuaguagg ucaugacacc uuuaccaaag uuaagccuuc ugcugcuagc | 420 |
| auugaugcug ccaagaaagc aggcguaaac aacgguaacc cucuagacgc uguucagcaa | 480 |

```
caccaccacc accaccacua a                                               501
```

<210> SEQ ID NO 37
<211> LENGTH: 502
<212> TYPE: RNA
<213> ORGANISM: Artificial Sequence
<220> FEATURE:
<223> OTHER INFORMATION: Synthetic

<400> SEQUENCE: 37

```
augcgggccg uccaaggacu ccaaagcuca gguuucugca gccgaagcug guaucacugg    60
caccugguau aaccaacugg ggucgacuuu cauugugacc gcuggugcgg acggagcucu   120
gacuggcacc uacgaaucug cgguugguaa cgcagaaucc cgcuacguac ugacuggccg   180
uuaugacucu gcaccugcca ccgauggcuc ugguaccgcu cugggcugga cuguggcuug   240
gaaaaacaac uagcguaaug cgcacagcgc cacuacgugg ucuggccaau acguuggcgg   300
ugcugaggcu cguaucaaca cucaguggcu guuaacaucc ggcacuaccg aagcgaaugc   360
auggaaaucg acacuaguag gucaugacac cuuuaccaaa guuaagccuu cugcugcuag   420
cauugaugcu gccaagaaag caggcguaaa caacgguaac ccucuagacg cuguucagca   480
acaccaccac caccaccacu aa                                            502
```

<210> SEQ ID NO 38
<211> LENGTH: 76
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (73)..(73)
<223> OTHER INFORMATION: n is a, c, g, or u

<400> SEQUENCE: 38

```
gggagaguag uucaauggua gaacgucggu cucuaaaacc gagcguugag gguucgauuc    60
cuuucucucc cancca                                                    76
```

<210> SEQ ID NO 39
<211> LENGTH: 77
<212> TYPE: RNA
<213> ORGANISM: Saccharomyces cerevisiae

<400> SEQUENCE: 39

```
gcggauuuag cucaguuggg agagcgccag acucccgaau cuggaggucc uguguucgau    60
ccacagaauu cgcacca                                                   77
```

<210> SEQ ID NO 40
<211> LENGTH: 78
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (75)..(75)
<223> OTHER INFORMATION: n is a, c, g, or u

<400> SEQUENCE: 40

```
gcggauuuag cucaguuggg agagcgccag acucccgaau cuggaggucc uguguucgau    60
ccacagaauu cgcancca                                                  78
```

<210> SEQ ID NO 41

```
<211> LENGTH: 556
<212> TYPE: RNA
<213> ORGANISM: Artificial Sequence
<220> FEATURE:
<223> OTHER INFORMATION: Synthetic

<400> SEQUENCE: 41
auggcuagca ugacuggugg acagcaaaug ggucccggg aguaacgaau uccauaugga      60
cccguccaag gacuccaaag cucagguuuc ugcagccgaa gcugguauca cuggcaccug    120
guauaaccaa cuggggucga cuuucauugu gaccgcuggu gcggacggag cucugacugg    180
caccuacgaa ucugcgguug guaacgcaga aucccgcuac guacugacug gccguuauga    240
cucugcaccu gccaccgaug gcucuggguac cgcucgggc uggacugugg cuuggaaaaa    300
caacuaucgu aaugcgcaca gcgccacuac guggucuggc caauacguug gcggugcuga    360
ggcucguauc aacacucagu ggcuguuaac auccggcacu accgaagcga augcauggaa    420
aucgacacua guaggucaug acaccuuuac caaaguuaag ccuucugcug cuagcauuga    480
ugcugccaag aaagcaggcg uaaacaacgg uaacccucua gacgcuguuc agcaacacca    540
ccaccaccac cacuaa                                                    556
```

MUTANT TRNA FOR INTRODUCING UNNATURAL AMINO ACID INTO PROTEIN

CROSS-REFERENCE TO RELATED APPLICATIONS

The present application is a 35 U.S.C. §371 National Stage patent application of International patent application PCT/JP2006/323064, filed on Nov. 14, 2006, which claims priority to Japanese patent application JP 2005-329115, filed on Nov. 14, 2005.

TECHNICAL FIELD

The present invention relates to tRNA for introducing an unnatural amino acid, such as a labeled amino acid, into a protein.

BACKGROUND ART

In general, chemical modification of a specific protein residue is carried out to introduce a functional group onto the surface of a protein. Such chemical modification can be readily carried out and many specific residues can be modified at once, which is advantageous. On the other hand, excellent results are unlikely to be obtained in terms of reproducibility of the control of modified sites and/or the number of modified sites, which is problematic. Along with the recent developments in genetic engineering, it has become possible to substitute amino acid residues in proteins. Thus, it has become possible to introduce a desired unnatural amino acid having an amino skeleton into a protein by modifying a protein synthesis system, resulting in the realization of synthesis of a protein carrying functional groups with good reproducibility.

During protein synthesis, an amino acid first binds to the 3' end of tRNA and then is transferred to a ribosome, where protein synthesis takes place. In a ribosome, translation from codons to amino acids takes place. With the use of tRNA bound to an unnatural amino acid, an unnatural amino acid can be incorporated into a protein.

The following method can be used for introducing an unnatural amino acid into a protein: a method wherein a codon at a target site for introduction is first substituted with a stop codon UAG and then translation is carried out in the presence of tRNA that has CUA as an anticodon and is aminoacylated with an unnatural amino acid (see Non-Patent Documents 1 to 4). In such a method, examples of tRNA used include tRNA for yeast phenylalanine (see Non-Patent Documents 1 and 2), tRNA for *E. coli* asparagine, tRNA for tetrahymena glutamine (see Non-Patent Document 3), and tRNA for *E. coli* glycine (see Non-Patent Document 4).

However, since tRNA that has CUA as an anticodon and is aminoacylated with an unnatural amino acid competes with a termination factor upon translation of UAG, the efficiency of introduction of an unnatural amino acid is not high in such case.

Non-Patent Document 1: Science, 244, p. 182, 1989
Non-Patent Document 2: Nucleic Acids Res., 18, 83-88, 1989
Non-Patent Document 3: Chem. Biol., 3, 1033-1038, 1996
Non-Patent Document 4: J. Am. Chem. Soc., 111, p. 8013, 1989

DISCLOSURE OF THE INVENTION

It is an objective of the present invention to provide tRNA that has CUA as an anticodon and is aminoacylated with an unnatural amino acid, such tRNA being capable of efficiently introducing an unnatural amino acid into a protein without competing with a termination factor.

The present inventors searched for tRNA that can efficiently introduce an unnatural amino acid into a protein with the use of a stop codon UAG among tRNAs derived from a variety of the living species. Accordingly, they have found that a tRNA for Trp having CUA as an anticodon can introduce an unnatural amino acid with good efficiency. In addition, they have found that tRNA for Trp obtained by modifying the above tRNA can introduce an unnatural amino acid with better efficiency while the addition of a natural amino acid caused by aminoacyl tRNA synthase does not take place, such tRNA for TRp having an anticodon CUA, G at the 5' end, C as a base paring with the G at the 5' end (generally designated as the $72^{nd}$ base), and A as a base next to the C. Further, they have found that the most preferable tRNA among the above examples is *Mycoplasma capricolumn* Trp tRNA (a G1-C72, A73 mutant) having the following sequence: GGGAGAGUAG UUCAAUGGUA GAACGUCGGU CUCUAAAACC GAGCGUUGAG GGUUCGAUUC CUUUCUCUCC CACCA (SEQ ID NO: 1). Furthermore, they have found that the efficiency of introduction of an unnatural amino acid can be improved by inserting a single base just before the CCA sequence at the 3' end of tRNA. According to the present invention, the above objective has been achieved in a manner such that efficient introduction of an unnatural amino acid can be realized with the use of the above tRNAs even when such tRNA competes with a termination factor.

Specifically, the present invention is described as follows.

[1] A mutant tRNA for tryptophan which pairs with a stop codon and has CUA an anticodon.
[2] The mutant tRNA which pairs with a stop codon according to [1], which has G at the 5' end, C as a base pairing with the G at the 5' end, and A as a base next to the C on the 3' side.
[3] The mutant tRNA which pairs with a stop codon according to [2], in which C pairing with the G at the 5' end is the $72^{nd}$ base from the 5' end and A next to the C on the 3' side is the $73^{rd}$ base from the 5' end.
[4] The mutant tRNA which pairs with a stop codon according to any one of [1] to [3], which is a prokaryotic-cell-derived tRNA.
[5] The mutant tRNA which pairs with a stop codon according to [4], which is an *E. coli* or *Mycoplasma capricolum*-derived tRNA.
[6] A mutant tRNA which pairs with a stop codon, which is a *Mycoplasma capricolum*-derived mutant tRNA comprising the base sequence represented by SEQ ID NO: 1.
[7] The mutant tRNA which pairs with a stop codon according to any one of [1] to [6], into which a single base A, C, G, or U has been inserted just before the CCA sequence at the 3' end.
[8] The mutant tRNA which pairs with a stop codon according to [7], in which C pairing with the G at the 5' end is the $72^{nd}$ base from the 5' end, A next to the C on the 3' side is the $73^{rd}$ base from the 5' end, and a single base A, C, G, or U has been further inserted so as to serve as the $74^{th}$ base from the 5' end.
[9] The mutant tRNA which pairs with a stop codon according to any one of [1] to [8], which is aminoacylated with an amino acid.
[10] The mutant tRNA which pairs with a stop codon according to [9], wherein the amino acid is an unnatural amino acid or a derivative thereof.

[11] The mutant tRNA which pairs with a stop codon according to [10], wherein the amino acid derivative is selected from the group consisting of hydroxy acid, mercapto acid, and carboxylic acid.

[12] The mutant tRNA which pairs with a stop codon according to any one of [9] to [11], wherein the amino acid is fluorescent-labeled.

[13] A method for introducing a desired amino acid into a protein, wherein an amino acid is introduced into a protein in which mRNA of the protein into which an amino acid is introduced, the mRNA having a stop codon that is corresponding to a site at which the amino acid is introduced, and the mutant tRNA which pairs with a stop codon according to any one of [1] to [12] are used and the mutant tRNA is allowed to pair with the stop codon.

[14] A mutant tRNA which pairs with a 4-base codon and has a sequence consisting of 4 bases as an anticodon, in which a single base A, G, C, or U has been inserted just before the CCA sequence at the 3' end.

[15] The mutant tRNA which pairs with a 4-base codon according to [14], which has CCCG as an anticodon and pairs with a 4-base codon CGCG.

[16] The mutant tRNA which pairs with a 4-base codon according to [14] or [15], which is a mutant tRNA for phenylalanine.

[17] The mutant tRNA which pairs with a 4-base codon according to any one of [14] to [16], which is a yeast-derived tRNA.

[18] A mutant tRNA which pairs with a 4-base codon, which is a yeast-derived mutant tRNA comprising the base sequence represented by SEQ ID NO: 40.

[19] The mutant tRNA which pairs with a 4-base codon according to any one of [14] to [18], which is aminoacy-lated with an amino acid.

[20] The mutant tRNA which pairs with a 4-base codon according to [19], wherein the amino acid is an unnatural amino acid, a modified amino acid, or a derivative of either thereof.

[21] The mutant tRNA which pairs with a 4-base codon according to [20], wherein the amino acid derivative is selected from the group consisting of hydroxy acid, mercapto acid, and carboxylic acid.

[22] The mutant tRNA which pairs with a 4-base codon according to any one of [19] to [21], wherein the amino acid is fluorescent-labeled.

[23] A method for introducing a desired amino acid into a protein, wherein an amino acid is introduced into a protein in which mRNA of the protein into which an amino acid is introduced, the mRNA having a 4-base codon that is corresponding to a site at which the amino acid is introduced) and the mutant tRNA which pairs with a stop codon according to any one of [14] to [22] are used and the mutant tRNA is allowed to pair with the 4-base codon.

[24] A method for producing a protein comprising a fluorescent-labeled amino acid labeled with a fluorescent substance that serves as an energy donor for fluorescence resonance energy transfer and a fluorescent-labeled amino acid labeled with a fluorescent substance that serves as an energy acceptor for fluorescence resonance energy transfer, such protein comprising the two different fluorescent-labeled amino acids located at positions on the protein at which the distance between the fluorescent substance that serves as an energy donor and the fluorescent substance that serves as an energy acceptor and their orientation relative to each other are changed due to changes in the protein conformation caused by the binding between the protein and a molecule capable of binding to a protein, resulting in changes in the efficiency of fluorescence resonance energy transfer, such method comprising the steps of:

preparing mRNA of the protein into which a single 4-base codon and a single stop codon have been inserted, in which the positions on the mRNA at which a 4-base codon and the stop codon are inserted correspond to the positions on the protein such that the distance and the orientation of the fluorescent substances are changed due to interaction between the protein and other molecules, resulting in changes in the efficiency of fluorescence resonance energy transfer;

preparing two different amino acids separately labeled with two types of fluorescent substances that can cause fluorescence resonance energy transfer, which are an amino acid bound to the tRNA having an anticodon that pairs with a 4-base codon and an amino acid bound to the tRNA according to any one of [1] to [12], respectively; and synthesizing the protein with the use of the mRNA and the amino-acid-binding tRNA.

[25] The method for producing a protein according to [24], wherein the tRNA comprising an anticodon corresponding to a 4-base codon is the mutant tRNA which pairs with a 4-base codon according to any one of [14] to [22].

[26] The method according to [13], wherein protein synthesis is carried out in a cell-free translation system.

[27] The method according to [23], wherein protein synthesis is carried out in a cell-free translation system.

[28] The method according to [24], wherein protein synthesis is carried out in a cell-free translation system.

[29] The method according to [25], wherein protein synthesis is carried out in a cell-free translation system.

This description includes part or all of the contents as disclosed in the description of Japanese Patent Application No. 2005-329115, which is a priority document of the present application.

BRIEF DESCRIPTION OF THE DRAWINGS

Figure 3A:
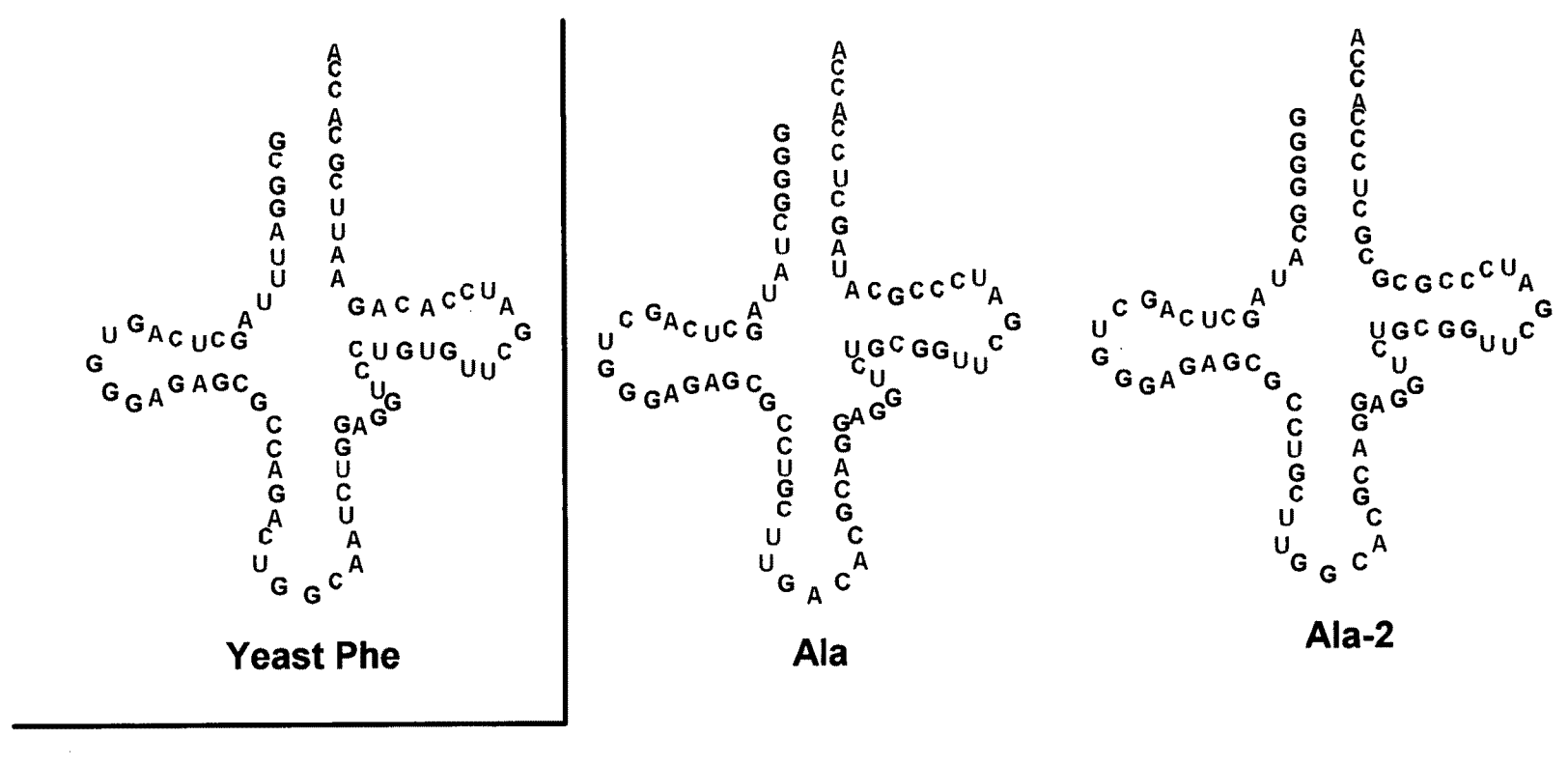

FIG. 3A shows the structures of *E. coli*-derived tRNAs.

FIG. 6C is a graph showing fluorescence band intensities of proteins subjected to introduction with the use of the individual mutants. The graph indicates the results of introduction of fluorescent-labeled amino acid into UAG with the use of a mutant tRNA for *E. coli*-derived tryptophan.

Figure 1:
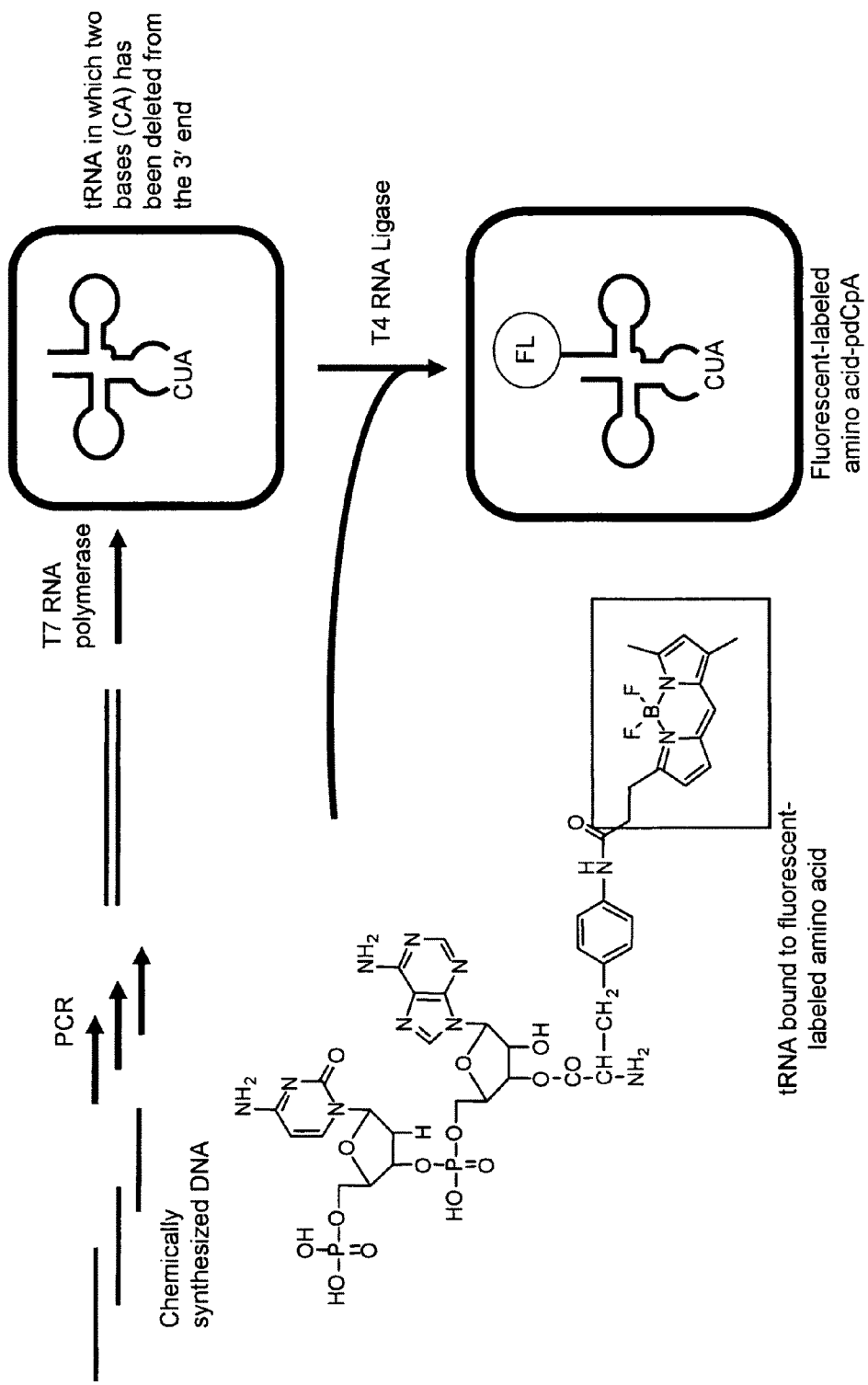
FIG. 1 shows the outline of a method for producing fluorescent-labeled amino acid-tRNA.
Figure 2:
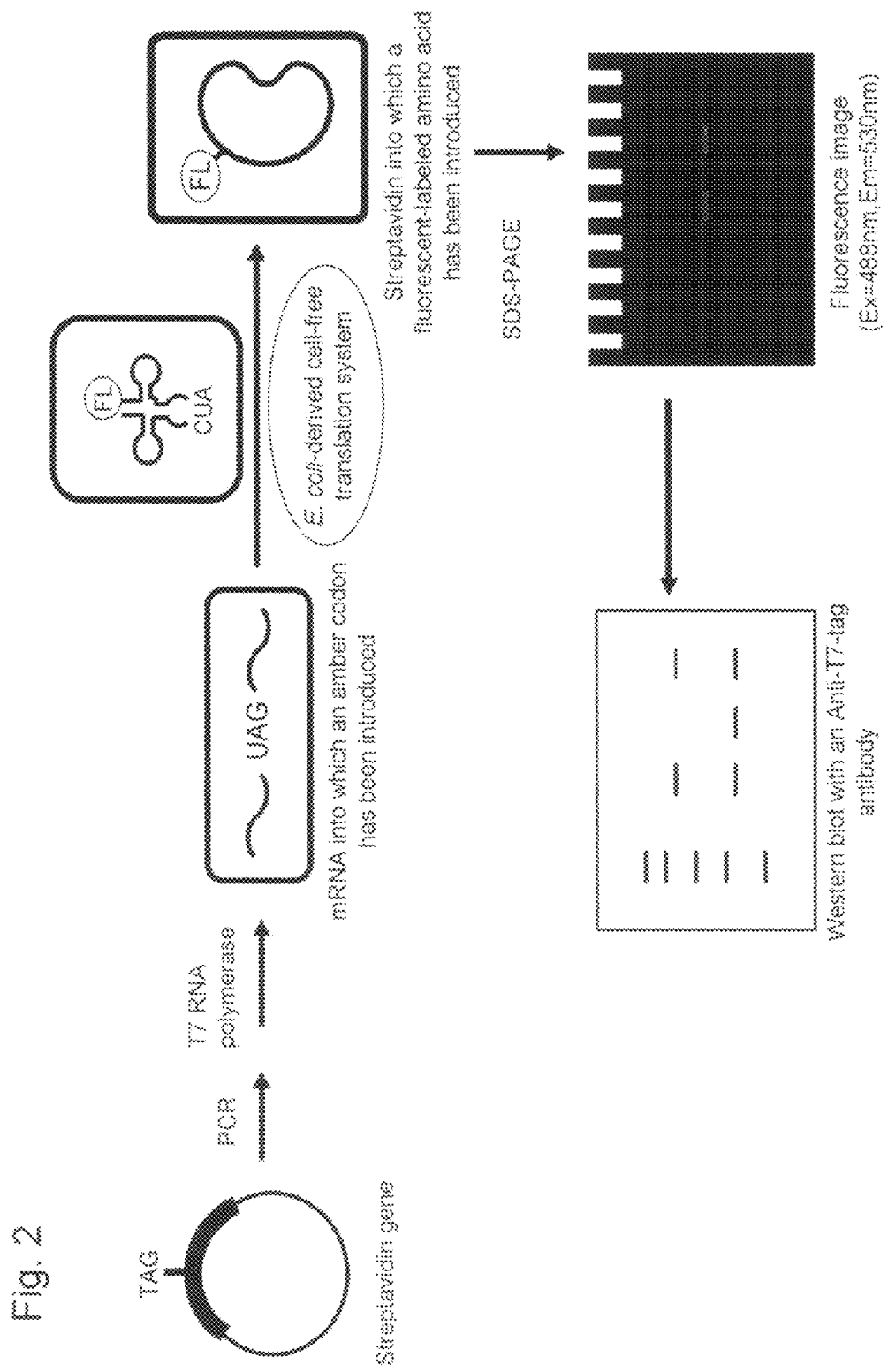
FIG. 2 shows the outline of a method for evaluating the introduction of fluorescent-labeled amino acid.
Figure 3B:
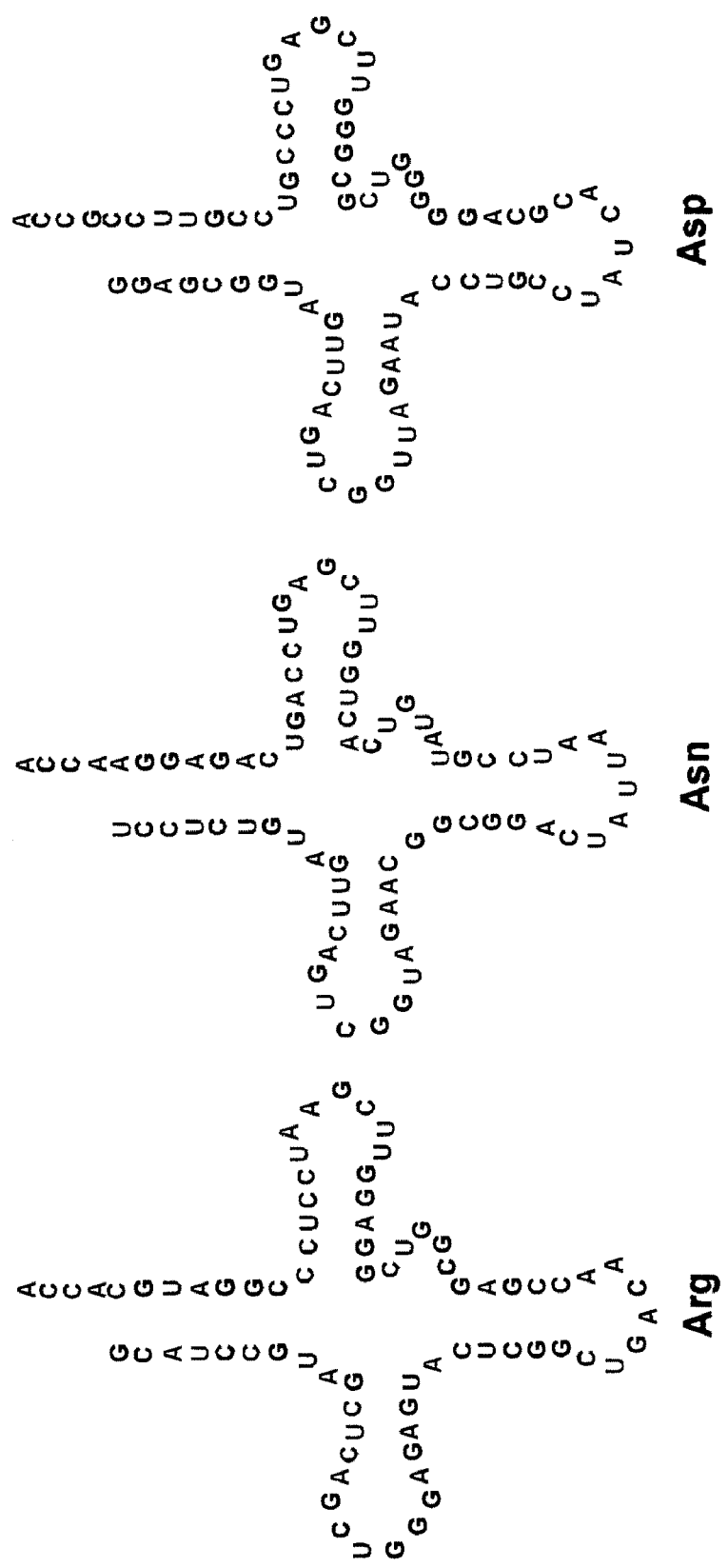
FIG. 3B shows the structures of *E. coli*-derived tRNAs.
Figure 3C:
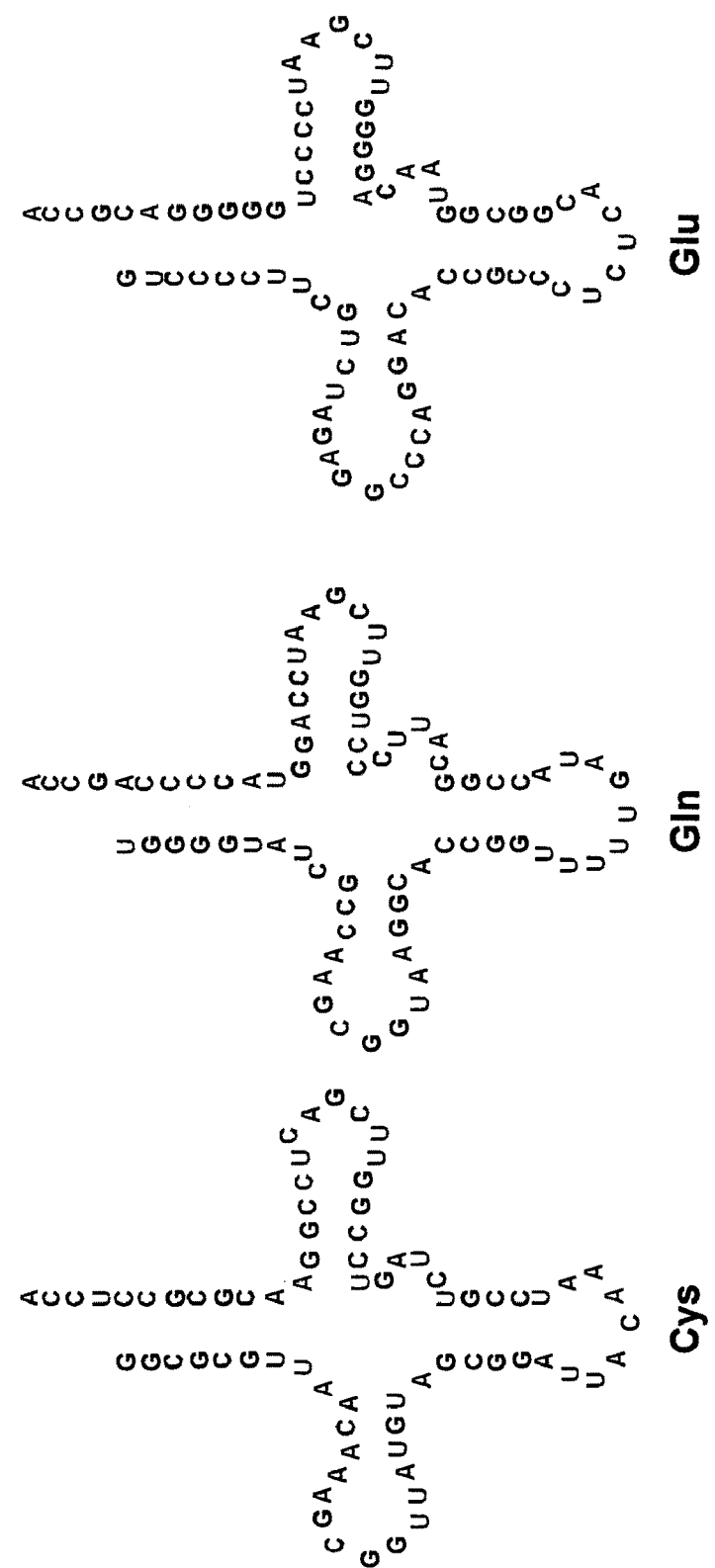
FIG. 3C shows the structures of *E. coli*-derived tRNAs.
Figure 3D:
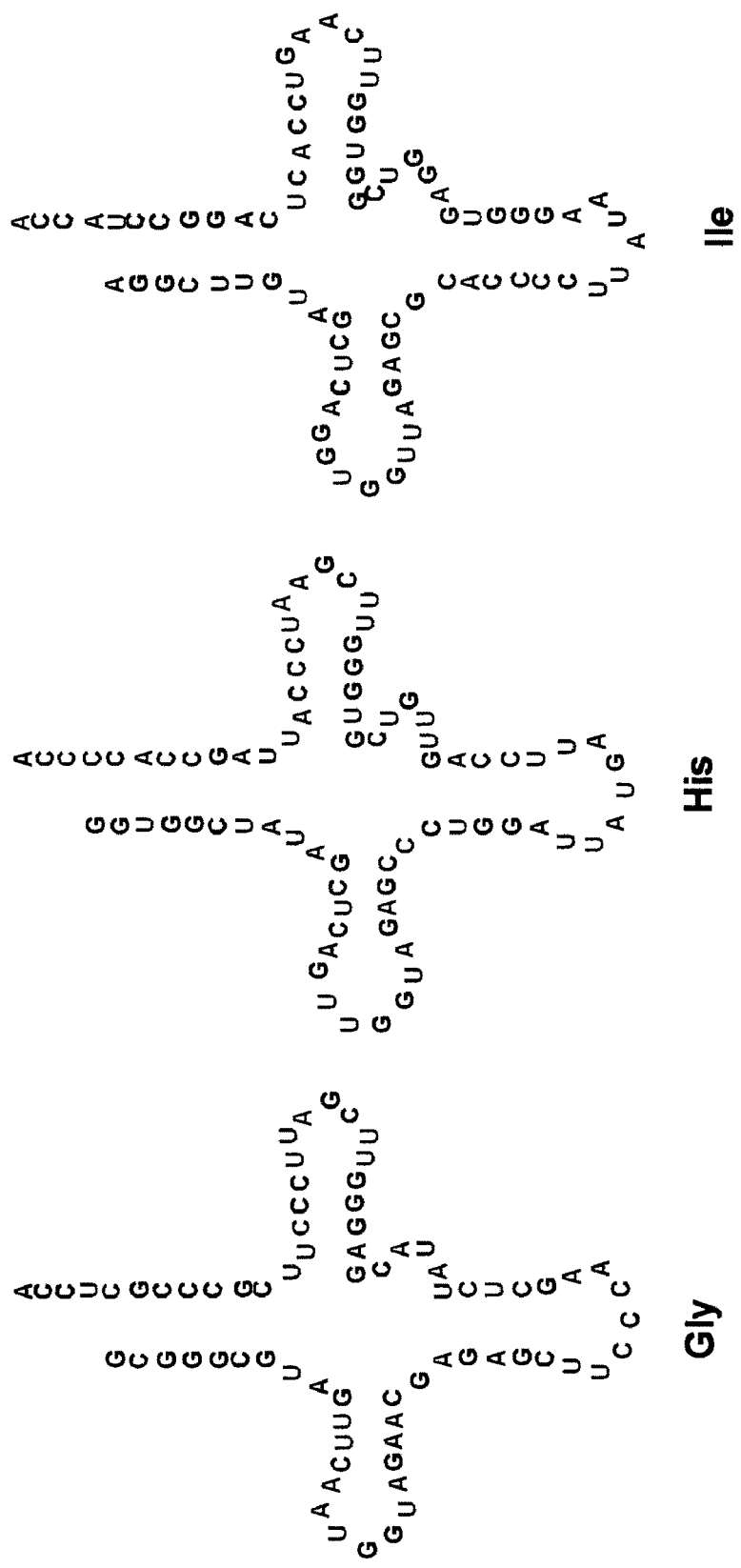
FIG. 3D shows the structures of *E. coli*-derived tRNAs.
Figure 3E:
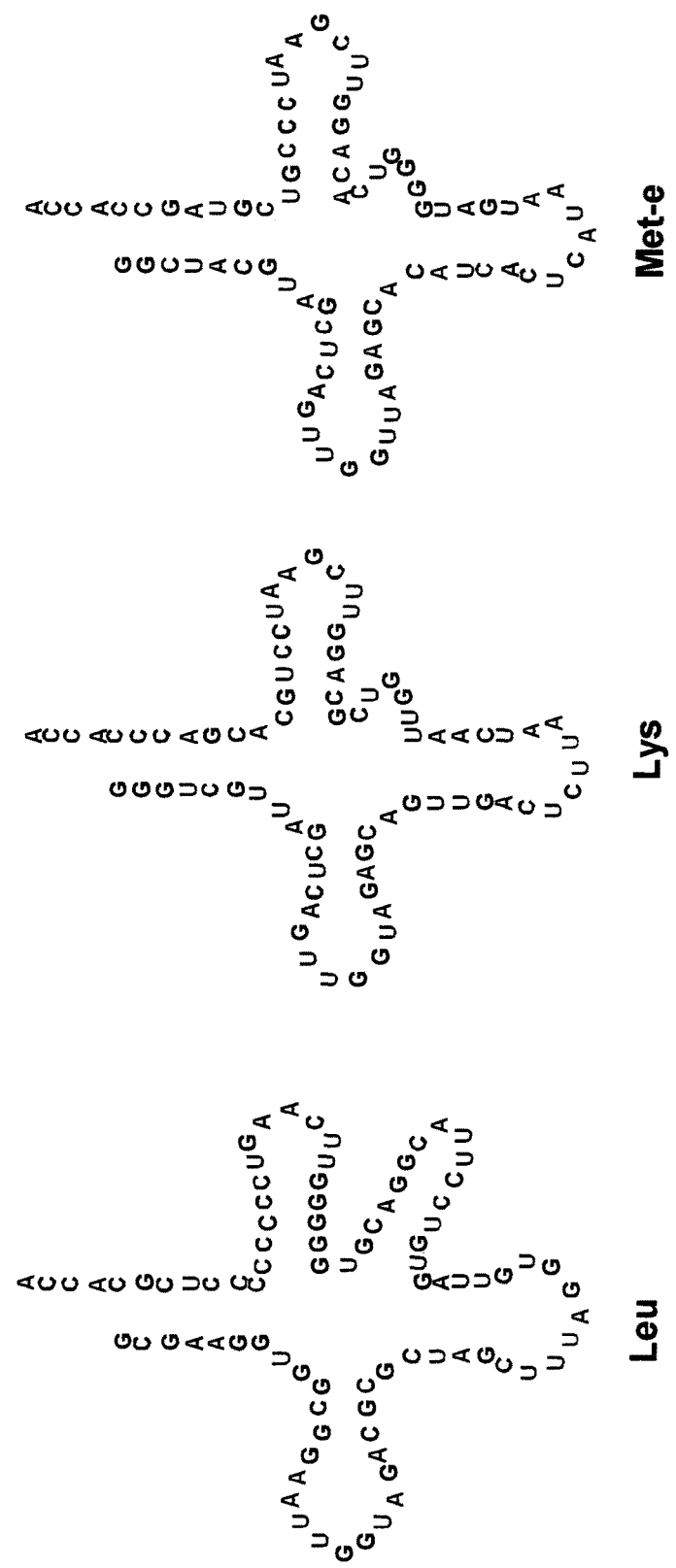
FIG. 3E shows the structures of *E. coli*-derived tRNAs.
Figure 3F:
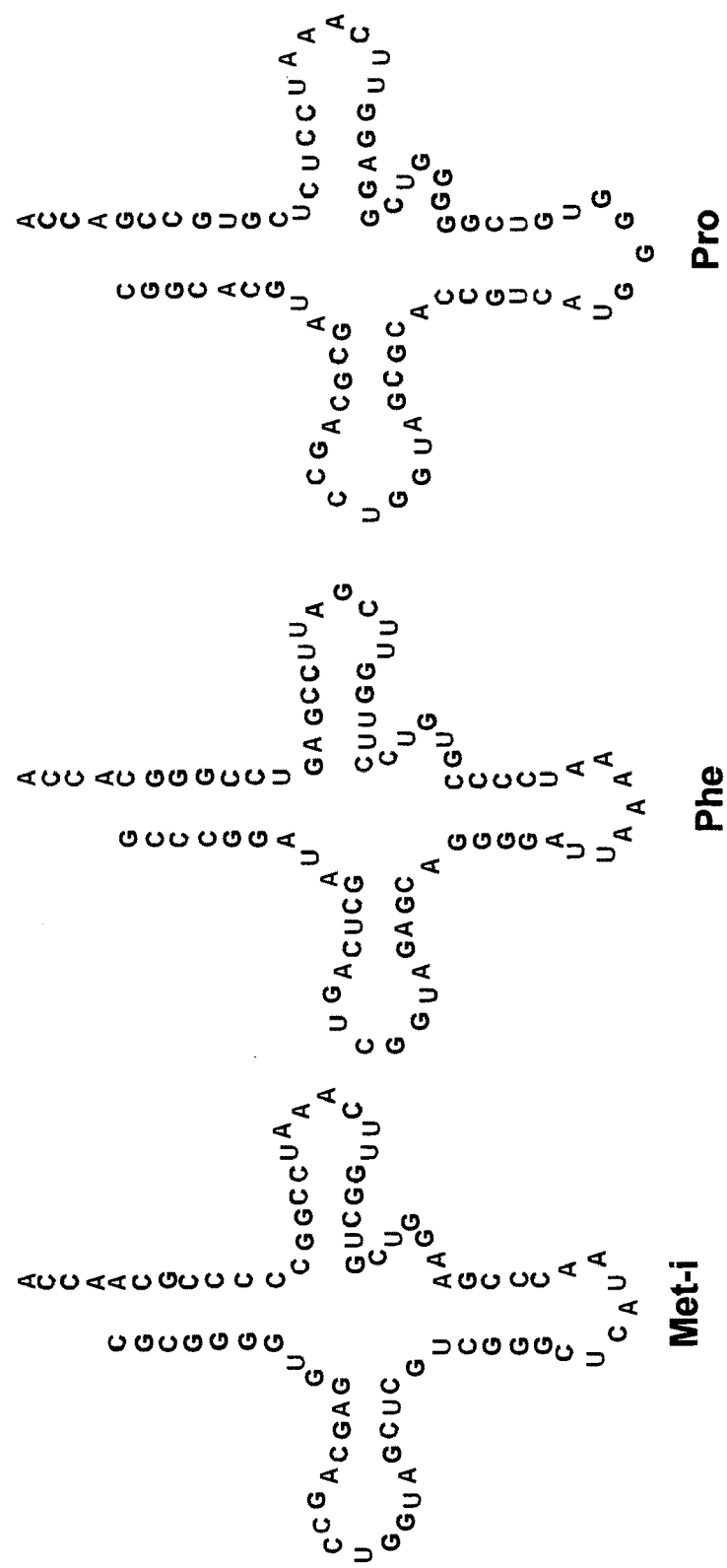
FIG. 3F shows the structures of *E. coli*-derived tRNAs.
Figure 3G:
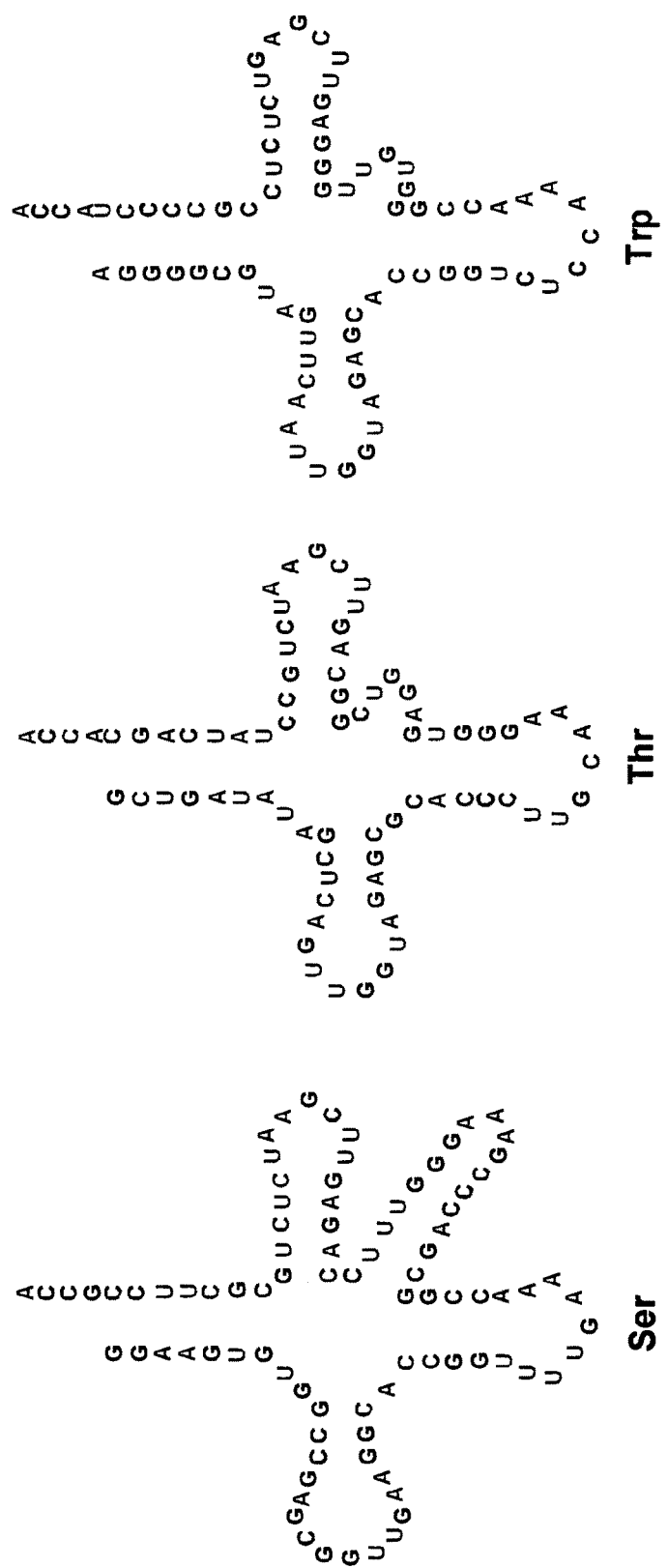
FIG. 3G shows the structures of *E. coli*-derived tRNAs.
Figure 3H:
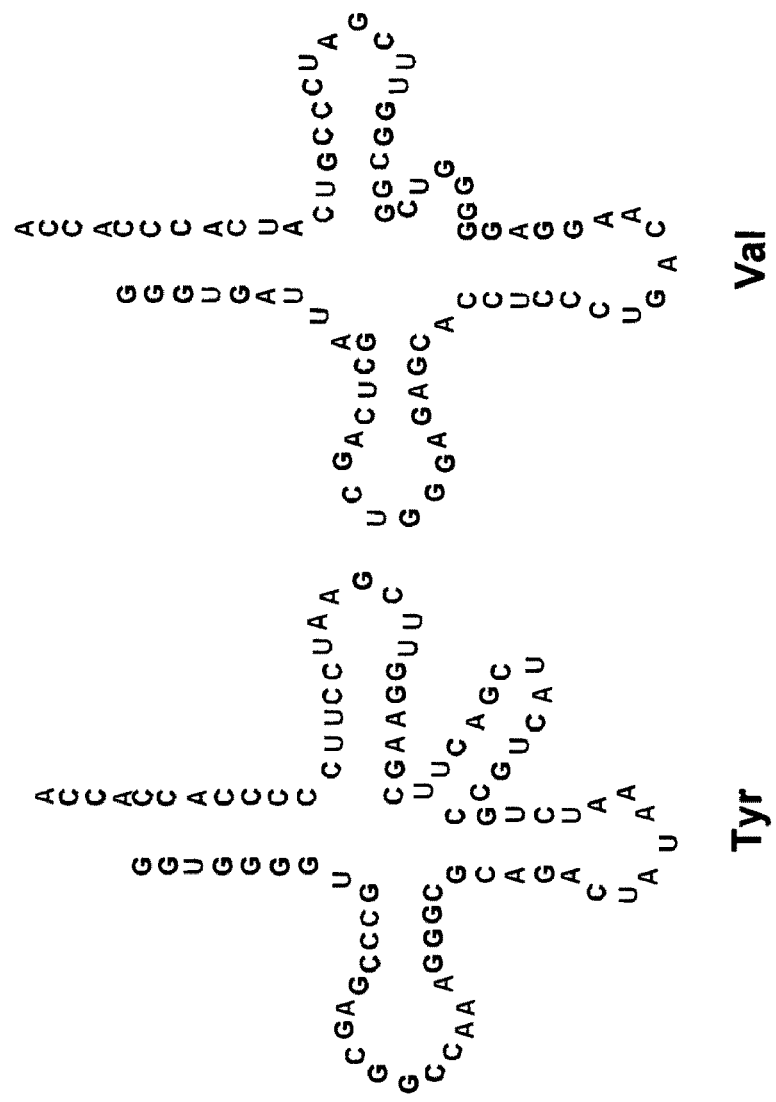
FIG. 3H shows the structures of *E. coli*-derived tRNAs.

In addition to the above, the tRNA of the present invention includes a mutant into which a single base (A, G, C, or U) has been inserted just before the CCA sequence at the 3' end. The above tRNA of the present invention has a single base positioned just before the CCA sequence at the 3' end (i.e., the $73^{rd}$ base in general), which does not pair with a base at the 5' end. A mutant tRNA into which a single base (A, G, C, or U) has been inserted just before the CCA sequence at the 3' end includes tRNA in which the $72^{nd}$ base, in general, is substituted with C, the $73^{rd}$ base, in general, is substituted with A or G, and A, G, C, or U is inserted as the $74^{th}$ base. The number of bases at a loop portion or a step portion differs depending on types of tRNA. In some cases, a base pairing with the base at the 5' end is not the $72^{nd}$ base. Specifically, the base numbers of the above $72^{nd}$, $73^{rd}$, and $74^{th}$ bases (at the substituted sites) from the 5' end may differ by 1, 2, 3, 4, or 5 bases, for example. The mutant tRNA of the present invention includes any tRNA having a conformation in which the base at the 5' end and a base paring with the base at the 5' end are substituted and a base next to either one of the bases on the 3' side is substituted, as long as the efficiency of introduction of unnatural amino acid is increased. In other words, the mutant tRNA of the present invention is a mutant tRNA that is generally a typical tRNA such as tRNA for *E. coli*- or *Mycoplasma capricolum*-derived tryptophan, in which a base corresponding to the $72^{nd}$ base from the 5' end is substituted and a base next to the base on the 3' side (i.e., a base corresponding to the $73^{rd}$ base at the 5' end of tRNA for *E. coli*- or *Mycoplasma capricolum*-derived tryptophan) is substituted. Herein, a base corresponding to the $72^{nd}$ base indicates a base at a position at which it pairs with the base at the 5' end. Also, a base corresponding to the $73^{rd}$ base indicates a base next to the $72^{nd}$ on the 3' side.

According to the present invention, a mutant tRNA into which a single base has been inserted just before the CCA sequence is designated as 73.1A, 73.1C, 73.1G, or 73.1U (provided that A, C, G, or U represents the type of inserted base). When an unnatural amino acid such as a labeled amino acid is allowed to bind to a mutant tRNA so as to be introduced into a protein, the efficiency of introduction of unnatural amino acid becomes high.

An example of the mutant tRNA of the present invention is a mutant tRNA for *Mycoplasma capricolum*-derived tryptophan into which a single base has been inserted just before the CCA sequence.

In addition, the mutant tRNA of the present invention includes a mutant tRNA paring with a 4-base codon, which is used for introduction of an unnatural amino acid with the use of a 4-base codon CGGG. For instance, such mutant tRNA is a mutant tRNA for yeast-derived phenylalanine having an anticodon comprising 4 bases (CCCG) into which a single base (A, C, G, or U) has been inserted just before the CCA sequence at the 3' end.

The above mutant tRNA can be synthesized based on sequence information. In addition, the above mutant tRNA can be produced by introducing a mutation into a tRNA such as the aforementioned tRNA for microorganism-derived tryptophan. A mutant can be produced using a conventional genetic engineering technique.

For instance, a mutation can be introduced into a gene with the use of a mutagenesis kit utilizing site-directed mutagenesis (such as Mutant-K (TAKARA) or Mutant-G (TAKARA)), an LA PCR in vitro Mutagenesis series kit (TAKARA), or the like according to a conventional method such as the Kunkel method or the Gapped duplex method, or according to a method based on such a method.

The tRNA of the present invention further includes an aminoacyl tRNA obtained by aminoacylating the above tRNA with an amino acid or an analog thereof. Examples of an amino acid or an analog thereof used for aminoacylation include, but are not limited to, natural amino acids, unnatural amino acids, and derivatives thereof. In addition, modified amino acids generated through post-translational modification such as fluorescent substanceylation, methylation, or acetylation are also included.

The term "unnatural amino acid" refers to any artificial compound having an amino skeleton in a single molecule thereof, which does not naturally exist. Such a compound can be prepared by allowing a different labeled compound to bind to an amino acid skeleton. Such an "amino acid skeleton" comprises a carboxyl group, an amino group, and a portion binding therebetween in an amino acid.

An example of an unnatural amino acid is a "labeled amino acid," which is an amino acid bound to a labeled compound. For instance, such unnatural amino acid is an amino acid obtained by allowing a labeled compound to bind to an amino acid having an amino acid skeleton comprising an aromatic ring such as a benzene ring on a side chain. In view of functions, photoresponsive amino acids, photoswitch amino acids, fluorescent probe amino acids, fluorescent-labeled amino acids, and the like can be used.

Examples of derivatives of such amino acids include hydroxy acid, mercapto acid, and carboxylic acid.

Labeled compounds used in the present invention are dye compounds, fluorescent substances, chemiluminescent/bioluminescent substances, enzyme substrates, coenzymes, antigenic substances, and protein binding substances, which are known to persons skilled in the art.

Preferably, fluorescent-labeled compounds have an excitation wavelength in the visible light range (approximately 400 to 700 nm). Further preferably, such compounds have a luminescence wavelength in the visible light range. Particularly preferably, such compounds have a strong luminescence intensity in a water solution.

A chemiluminescent or bioluminescent substance such as luciferin or Lumigen or a derivative thereof can be used as a labeled compound in the present invention.

Further, a compound can be adequately selected from among coenzymes, antigenic substances, substances known to bind to specific proteins, and the like depending on desired functions to be imparted to a target protein so that such compound can be used as a labeled compound in the present invention. For instance, when a substrate for a specific enzyme (e.g., a substrate for alkaline phosphatase, β-galactosidase, or the like) is introduced, detection can be carried out with the use of a color reaction of the enzyme. In addition, a protein labeled with an antigenic protein or a substance that is known to bind to a specific protein can be used for an indirect detection method using an antibody or a protein that binds thereto, which is advantageous in terms of the ease of purification. For instance, a functional protein labeled with biotin by the method of the present invention has a function of binding to avidin streptavidin via biotin. With the use of such function, it becomes possible to establish a system for detection of a specific substance with the use of the binding to avidin or streptavidin labeled by the method of the present invention or with a chemiluminescent compound or the like. In addition to the above examples, persons skilled in the art would be able to understand that it is possible to use, as a labeled compound, a substance that can be detected with the use of a variety of dyes and different biochemical, chemical, and immunochemical detection methods.

An amino acid is allowed to bind to a labeled compound directly or via a spacer. The term "spacer" indicates a portion that binds between an amino acid portion of a labeled amino acid molecule and a labeled compound. Specifically, an amino acid side chain of a labeled amino acid molecule does not directly bind to a labeled compound. It is thought that when at least one atom exists between an amino acid side chain and a labeled compound, an amino acid portion of the labeled amino acid binds to the labeled compound via a spacer. A spacer may comprise at least one atom of at least one of C, O, N, and S on the main chain thereof. In addition, the main chain structure of a spacer comprises 2 to 10 atoms, preferably 3 to 8 atoms, and more preferably 5, 6, or 7 atoms, which are the above atoms bound to each other in a linear chain. Such linear chain structure contains at least one double bond. Further, a spacer may have 1 to several, preferably 1 to 5, and more preferably 1 to 3 rings such as a benzene ring and/or a cyclohexyl ring. In addition, a spacer may have a ring structure comprising a benzene ring or a cyclohexyl ring or a structure obtained by combining a ring structure and the above linear chain structure. Specific examples of a spacer include: polyolefins such as polyethylene, polypropylene, polyisoprene, polystyrene, polyvinyl, and polyvinyl chloride; polyethers such as polyoxyethylene, polyethylene glycol, and polyvinyl alcohol; polyamide; polyester; polyimide; polyurethane; and polycarbonate.

Depending on types of labeled compound, it is advantageous to allow an amino acid to bind to a labeled compound via a spacer such that the functions of the labeled compound can be more effectively exhibited in the protein into which the labeled compound has been introduced. For instance, it is considered that, depending on types of labeled compound, steric hindrance in the protein into which the labeled compound has been introduced is more attenuated in the case of binding via a spacer.

Further, it is preferable that the labeled amino acid of the present invention have an aromatic ring on a side chain of an amino acid portion and that a labeled compound bind to the aromatic ring directly or via a spacer.

The term "aromatic ring" used herein generally refers to any unsaturated ring compound. Thus, such compound includes 5- or 6-membered heterocyclic aromatic rings and polycyclic compounds having a structure comprising at least 2 rings, preferably 2 to 5 rings, and more preferably 2 to 3 rings. Particularly preferably, an aromatic ring is a benzene ring. Among natural amino acids, phenylalanine, tryptophan, and tyrosine are natural aromatic amino acids having an aromatic ring on a side chain. An unnatural amino acid derived from such natural aromatic amino acid in which a labeled compound binds to the aromatic ring (directly or via a spacer) is a preferred example of the unnatural amino acid of the present invention.

The binding between an amino acid having an aromatic ring and a labeled compound (directly or via a spacer) may be binding between adequate functional groups. A labeled compound is allowed to bind directly or via a spacer to a different functional group of a natural or unnatural amino acid that is not involved in a peptide elongation reaction upon protein synthesis, such functional group being selected from the group consisting of an amino group, a thiol group, a carboxyl group, a hydroxyl group, an aldehyde group, an allyl group, and a halogenated alkyl group. Examples of a probe used for labeling of an amino group that can be used include compounds such as succinimide ester, isothiocyanate, sulfonylchloride, NBD-halide, and dichlorotriazine. Examples of a probe used for labeling of a thiol group that can be used include compounds such as alkyl halide, maleimide, and aziridine. Examples of a probe used for labeling of a carboxyl group that can be used include a diazomethane compound, aliphatic bromide, and carbodiimide. For instance, succinimide ester is introduced into a labeled compound directly or via a spacer and an amino group is introduced into an aromatic ring of an amino acid. In such a case, the labeled compound and the amino acid can be bound via an amide bond. Examples of an amino acid having an amino group that has been introduced into an aromatic ring include aminophenylalanine. A functional group used in the above case can be adequately selected and introduced. Also, the binding method can be adequately selected. In such a case, it is possible to allow an amino group on a side chain of aminophenylalanine to selectively react by carrying out an amide bond formation reaction at approximately pH 5 even in the presence of another amino group. Alternatively, the other amino groups are protected by butyloxycarbonylation (Boc: butyloxycarbonyl) or the like. In such a case, de-butyloxycarbonylation (Boc: butyloxycarbonyl) can be carried out, followed by a reaction. For such technique, for example, descriptions in "New Biochemistry Experimentation Course (Shin Seikagaku Jikken Koza) 1, protein VI, Structure-Function Correlation (Kozo-Kino Sokan)" and the like can be referred to.

An aromatic ring may bind to an atom forming an amino acid skeleton directly or indirectly via 1, 2, or 3 atoms of at least one of C, O, N, and S. When an aromatic ring is a benzene ring, the position on a benzene ring at which a spacer or a labeled compound binds to an amino acid is a para position or a meta position in the amino acid skeleton such that the efficiency of incorporation into a ribosome becomes higher, which is preferable. Particularly preferably, the position is a para position.

As described above, a labeled compound is allowed to bind to a functional group of an aromatic ring directly or via a spacer. In the case of aminophenylalanine, paraminophenylalanine and meta-aminophenylalanine are preferably used.

In order to allow an amino acid to bind to tRNA so as to produce aminoacyl tRNA, it is necessary to allow a specific group to first bind to an amino acid. For instance, when dinucleotide (pdCpA) is allowed to first bind to a carboxyl group of an amino acid, it is possible to produce an artificial aminoacyl tRNA by allowing tRNA (tRNA(-CA)) lacking a CA dinucleotide at the 3' end to bind thereto. Such artificial aminoacyl tRNA can be produced in accordance with descriptions in WO2004/009709 and the like. For instance, it is possible to produce aminoacyl pdCpA by a method comprising protecting an amino acid α amino group with a Boc group and an amino acid side chain functional group with Boc or OtBoc, allowing Boc-amino acid to be subjected to cyanomethyl esterification, and carrying out a reaction with pdCpA, or by a method comprising carrying out a reaction between Boc-amino acid and pdCpA with the use of the condensing agent carbonyldiimidazole (CDI). Binding with tRNA(-CA) may be carried out with the use of T4 RNA ligase.

It is possible to introduce an amino acid or a derivative thereof into a protein with the use of the tRNA of the present invention by synthesizing a protein in an intracellular or cell-free translation system with the use of DNA encoding the protein into which an amino acid or a derivative thereof is introduced, such DNA having a stop codon TAG that has been introduced at a codon position corresponding to a position for introduction of an amino acid or a derivative thereof, and the aminoacyl tRNA of the present invention to which an amino acid or a derivative has been bound.

Synthesis in a cell-free translation system can be carried out by mixing in vitro an expression vector containing a gene to be expressed with a necessary reagent so as to allow the gene to be expressed without introducing the expression vector into a host cell (Spirin, A. S. et al., (1988) "A continuous cell-free translation system capable of producing polypeptides in high yield" Science 242, 1162; Kim, D. M. et al., (1996) "A highly efficient cell-free protein synthesis system from E. coli" Eur. J. Biochem. 239, 881-886). In some cases, the term "cell-free protein synthesis system" merely indicates a cell-free translation system in which genetic information contained in mRNA is decoded such that protein synthesis is carried out in a ribosome. Also, in some cases, the term indicates both a cell-free transcription system in which RNA synthesis is carried out using DNA as a template and the above cell-free translation system. In a cell-free translation system, an organism extract is used. An organism extract contains components necessary for protein synthesis. Examples of such components include ribosomes, 20 types of aminoacyl tRNA synthases, methionyl-tRNA transformylase, three types of translation initiation factors (IF1, IF2, and IF3), three types of translation elongation factors (EF-G, EF-Tu, and EF-Ts), three types of translation termination factors (RF1, RF2, and RF3), a ribosome recycling factor (RRF), and RNA polymerase. In addition to the above examples, another protein may be added for efficient translation. Persons skilled in the art can determine a protein that can be added for further efficient translation. Examples of an organism extract that can be used include E. coli-derived organism extracts, wheat germ-derived organism extracts, rabbit reticulocyte-derived organism extracts, animal cell-derived organism extracts, and insect cell-derived organism extracts. An organism extract can be obtained by, for example, disruption using a French press or glass beads. An example of E. coli-derived microorganism extract is an S30 extract, which can be obtained by, for example, the method of Pratt et al. (Pratt, Transcription and Translation—a practical approach, Henes, B. D. and Higgins, S. J. ed., IRL Press, Oxford, 179-209 [1984]). An S30 extract contains ribosome, 20 types of aminoacyl tRNA synthases, methionyl-tRNA transformylase, three types of translation initiation factors (IF1, IF2, and IF3), three types of translation elongation factors (EF-G, EF-Tu, and EF-Ts), three types of translation termination factors (RF1, RF2, and RF3), a ribosome recycling factor (RRF), and the like. In addition to the above organism extract, a cell-free protein synthesis system may contain an ATP regenerating system, a plasmid containing a promoter and a nucleic acid encoding a protein to be expressed (or mRNA encoding a protein to be expressed), tRNA, RNA polymerase, an RNase inhibitor, an energy source such as ATP, GTP, CTP, or UTP, a buffer, amino acids, salts, antimicrobial agents, and the like. The concentration of each component can be adequately determined.

An ATP regenerating system is not limited, and thus a combination of a known phosphate donor and a known kinase can be used. Examples of such a combination include a combination of phosphoenolpyruvate (PEP) and pyruvate kinase (PK), a combination of creatine phosphate (CP) and creatine kinase (CK), and a combination of acetyl phosphate (AP) and acetate kinase (AK). An ATP regenerating system produced based on such a combination may be added to a cell-free protein synthesis system.

It is necessary for a cell-free protein synthesis system to contain mRNA encoding a protein to be produced. For such mRNA, the cell-free protein synthesis system may contain a system that transcribes a nucleic acid into a cell-free protein synthesis system; that is to say, a system that produces mRNA encoding the protein. In such case, DNA is added. In addition, it is also possible to separately synthesizing mRNA via transcription or the like from template DNA with the use of T7 DNA polymerase or the like so as to add the obtained mRNA to the cell-free protein synthesis system of the present invention. mRNA can be produced with the use of a plasmid containing an adequate promoter and DNA encoding a protein to be produced, such DNA being located downstream of the promoter, and RNA polymerase that acts on the promoter. The plasmid used herein is not limited. A known plasmid can be used by introducing an adequate promoter, a ribosome binding site, and the like thereinto by a known gene engineering technique. Persons skilled in the art can adequately select a plasmid used in the present invention or design and construct such plasmid by themselves. A promoter that can be used may be an endogenous promoter contained in a microorganism used in a cell-free protein synthesis system or an exogenous promoter. Examples of a promoter that can be preferably used include the above Trc promoter, T7 promoter, and Tac promoter, which are superior in terms of efficiency.

A protein can be expressed with the use of a commercially available cell-free expression kit. Examples of such kit include the Rapid Translation System (RTS) (Roche) and the Expressway In Vitro Protein Synthesis System (Invitrogen). In such case, an expression vector to be used is not limited, and thus a vector available for a cell-free translation system can be used. An example of an expression vector for the former kit is pIVEX2.2bNde. Examples of an expression vector for the latter kit are pEXP1 and pEXP2.

With the use of the tRNA of the present invention, it is possible to introduce an unnatural amino acid such as fluorescent substance-labeled amino acid into an arbitrary site on a protein such that a fluorescent-labeled protein can be produced. For instance, PDIPY FL-aminophenylalanine is introduced into the Tyr84 site of streptavidin, such that fluorescent-labeled streptavidin can be produced.

In addition, interaction between a protein and other molecules can be detected by introducing fluorescent-labeled amino acids that can serve as a donor and an acceptor for fluorescence resonance energy transfer into two arbitrary sites on a protein. In such case, either one of fluorescent-labeled amino acids may be introduced by the 4-base codon method. The 4-base codon method can be carried out in accordance with descriptions in Hohsaka T., et al., J. Am. Chem. Soc., 118, 9778-9779, 1996 and Hohsaka T., et al., J. Am. Chem. Soc., 121, 34-40, 1999. Examples of such protein include any protein that interacts molecules so as to cause changes in conformation. Examples of such protein include calmodulin, cGMP-dependent protein kinase, a steroid hormone acceptor, a ligand binding domain of a steroid hormone acceptor, protein kinase C, an inositol-1,4,5-triosephosphate acceptor, recoverin, maltose binding protein, and DNA binding protein. A molecule that interacts with a protein is specified for each protein. Examples of such molecules include organic or inorganic low-molecular-weight molecules such as proteins, nucleic acids, sugars, and ions. In a case in which a protein is calmodulin, examples of such molecule include a calmodulin binding protein and a calcium ion. In addition, an example of a cGMP-dependent protein kinase is cGMP and an example of a maltose binding protein is maltose. Further, in the case of a steroid hormone acceptor or a DNA binding protein, a steroid hormone or DNA specific to the relevant protein is used. Examples of a substance that can serve as an energy donor and a substance that can serve as an energy acceptor for fluorescence resonance energy transfer include any known fluorescent substances such as BODIPY compounds, rhodamine (TAMRA), fluorescein (FITC), Texas Red, acridine orange, Cyber Green, Cy3, Cy5, and derivatives thereof. Fluorescent substances that can serve as an energy donor and a fluorescent substance that can serve as an energy acceptor for fluorescence resonance energy transfer may be selected in a manner such that the excitation spectrum of a substance that serves as an energy acceptor overlaps the radiation spectrum of a substance that serves as an energy donor. For instance, BODIPY (registered trademark) FL and BODIPY (registered trademark) 558/568 can be selected as an energy donor and an energy acceptor, respectively. Alternatively, a combination of an energy donor and an energy acceptor can be BODIPY FL and BODIPY 576/586, BODIPY FL and TAMRA, BODIPY FL and Cy3, Fluorescein and BODIPY 558/568, Alexa488 and BODIPY 558/568, BODIPY 558/568 and Cy5, or the like.

In the case of the protein of the present invention, it is necessary for the protein to contain an energy donor and an energy acceptor, which are located at positions relative to each other such that an orientation appropriate for induction of fluorescence resonance energy transfer can be maintained when the protein conformation is changed.

For such purpose, a fluorescent-labeled amino acid that is labeled with a fluorescent substance is introduced into a specific site in a protein. The position at which a fluorescent-labeled amino acid is introduced differs depending on the protein into which the fluorescent-labeled amino acid is introduced. The protein conformation is analyzed based on the amino acid sequence of a natural protein and then fluorescent-labeled amino acids are introduced into amino acid sites that are located at positions in the vicinity of each other in the protein conformation. The protein conformation can be predicted with the use of, for example, commercially available protein conformation analysis software. Alternatively, either an energy donor or an energy acceptor is first introduced at the N or C terminal of a protein and the other is introduced into several to several tens of sites in the protein. Then, an introduction position appropriate for the present invention can be selected from among the above sites.

For instance, when a protein is calmodulin, an amino acid labeled with 4,4-difluoro-5,7-dimethyl-4-bora-3a,4a-diaza-s-indacene-3-propionic acid (BODIPY FL) and an amino acid labeled with 4-difluoro-5-(2-thienyl)-4-bora-3a,4a-diaza-s-indacene-3-propionic acid (BODIPY 558/568) can be introduced into the $40^{th}$ base and the N terminal or the $99^{th}$ base and the N terminal of a calmodulin amino acid sequence, respectively. Meanwhile, when an amino acid labeled with 4,4-difluoro-5,7-dimethyl-4-bora-3a,4a-diaza-s-indacene-3-propionic acid and an amino acid labeled with 4-difluoro-5-(2-thienyl)-4-bora-3a,4a-diaza-s-indacene-3-propionic acid are introduced into the $113^{th}$ base and the N terminal or the $148^{th}$ base and the N terminal of a calmodulin amino acid sequence, respectively, the efficiency of sufficient fluorescence resonance energy transfer is not changed even when a protein interacts with other molecules. With the use of the thus obtained protein of the present invention, interaction between the protein and other molecules can be detected. By allowing the protein of the present invention to interact with other molecules, the conformation of the protein of the present invention is changed such that the distance between an energy acceptor and an energy donor and their orientation relative to each other are changed. When the protein in the above state is irradiated with the excitation light of the energy donor, fluorescence resonance energy transfer (FRET) takes place between the energy donor and the energy acceptor. At such time, the distance between the energy acceptor and the energy donor and their orientation relative to each other are changed so that FRET efficiency is also changed. Changes in the protein conformation can be detected by measuring such changes.

As a light source for excitation light, a light source obtained by allowing broad-wavelength-range ultraviolet light or visible light to have a desired wavelength range with the use of a filter or a spectrometer can be used. Alternatively, a monochromatic light source such as a laser can be used. When a laser light source is used, a helium-cadmium laser (442 nm) is generally used. However, a blue diode laser (405 nm), an argon ion laser (457 nm), an LD excitation solid laser (diode-pumped solid-state laser) (430 nm), and the like may be used. In the case of the two-photon excitation method, a pulse laser (approximately 800 nm) may be used.

The above proteins correspond to the following proteins:

1. A protein comprising a fluorescent-labeled amino acid labeled with a fluorescent substance that serves as a energy donor for fluorescence resonance energy transfer and a fluorescent-labeled amino acid labeled with a fluorescent substance that serves as an energy acceptor for fluorescence resonance energy transfer, such protein comprising the two different fluorescent-labeled amino acids located at positions on the protein at which the distance between the fluorescent substance that serves as a energy donor and the fluorescent substance that serves as an energy acceptor and their orientation relative to each other are changed due to changes in the protein conformation caused by the binding between the protein and a molecule capable of binding to a protein, resulting in changes in the efficiency of fluorescence resonance energy transfer;

2. The protein according to 1 above, wherein either the fluorescent-labeled amino acid labeled with a fluorescent substance that serves as a energy donor for fluorescence resonance energy transfer or the fluorescent-labeled amino acid labeled with a fluorescent substance that serves as an energy acceptor for fluorescence resonance energy transfer protein exists at the N or C terminal and the other exists at a non-N- or non-C-terminal site;

3. The protein according to 1 or 2 above, wherein the amino acids each labeled with a fluorescent substance have been introduced by the 4-base codon method;

4. The protein according to any one of 1 to 3 above, wherein the molecule capable of binding to a protein is selected from the group consisting of proteins, nucleic acids, sugars, and low-molecular-weight molecules;

5. The protein according to any one of 1 to 4 above, wherein the fluorescent substance that serves as an energy donor and the fluorescent substance that serves as an energy acceptor are fluorescent substances which have an excitation wavelength and an emission wavelength, respectively, in the visual light range;

6. The protein according to 5 above, wherein the fluorescent substance that serves as an energy donor and the fluorescent substance that serves as an energy acceptor each are a molecule having a chemical structure comprising 4,4-difluoro-4-bora-3a,4a-diaza-s-indacene as a base structure or a salt or derivative thereof;

7. The protein according to 6 above, wherein the fluorescent substance that serves as an energy donor is 4,4-difluoro-5,7-dimethyl-4-bora-3a,4a-diaza-s-indacene-3-propionic acid or a salt thereof and the fluorescent substance that serves as an energy acceptor is 4,4-difluoro-5-(2-thienyl)-4-bora-3a,4a-diaza-s-indacene-3-propionic acid or a salt thereof;

8. The protein according to 1 to 7 above, wherein the fluorescent substance that serves as an energy donor and the fluorescent substance that serves as an energy acceptor bind to an amino group located at the para position of p-aminophenylalanine;

9. The protein according to 1 to 8 above, which is calmodulin;

10. The calmodulin according to 9 above, wherein the amino acids labeled with a fluorescent substance that serves as an energy donor and a fluorescent substance that serves as an energy acceptor are located at positions on the calmodulin in a manner such that the distance therebetween and their orientation relative to each other are changed when the calmodulin interacts with a calmodulin-binding protein and a calcium ion, resulting in changes in the efficiency of fluorescence resonance energy transfer;

11. The calmodulin according to 10 above, wherein the fluorescent substance that serves as an energy donor is 4,4-difluoro-5,7-dimethyl-4-bora-3a,4a-diaza-s-indacene-3-propionic acid or a salt thereof, the fluorescent substance that serves as an energy acceptor is 4-difluoro-5-(2-thienyl)-4-bora-3a,4a-diaza-s-indacene-3-propionic acid or a salt thereof, and the amino acids labeled with such fluorescent substances are located at positions on the calmodulin in a manner such that the distance therebetween and their orientation relative to each other are changed when the calmodulin interacts with a calmodulin-binding protein and a calcium ion, resulting in changes in the efficiency of fluorescence resonance energy transfer; and 12. A calmodulin containing 4,4-difluoro-5,7-dimethyl-4-bora-3a,4a-diaza-s-indacene-3-propionic acid or a salt thereof and 4-difluoro-5-(2-thienyl)-4-bora-3a,4a-diaza-s-indacene-3-propionic acid or a salt thereof at the $40^{th}$ base and the N terminal or at the $99^{th}$ base and the N terminal, respectively, of the calmodulin amino acid sequence.

The present invention is hereafter described in greater detail with reference to the following examples, although the technical scope of the present invention is not limited thereto.

EXAMPLE 1

A Method for Producing Fluorescent-Labeled Amino Acid-tRNA

Three oligonucleotides were chemically synthesized based on individual tRNA base sequences. PCR was carried out using a primer comprising a T7 promoter and a base sequence corresponding to the $1^{st}$ to $31^{st}$ bases of tRNA and a primer comprising a base sequence corresponding to the $24^{th}$ to $46^{th}$ bases of tRNA (provided that KOD Dash buffer, 0.2 mM dNTP, 1.25 units of KOD Dash, and 50 nmol primers are contained in 50 µl). Thus, a double-strand DNA was obtained. The reaction solution (1 µL) was designated as a template and then PCR was carried out under the same conditions as above with the use of a primer having a T7 promoter sequence (CTAATACGACTCACTATA) (SEQ ID NO: 32) and a primer having a base sequence corresponding to the $39^{th}$ to $74^{th}$ bases of tRNA, such that the tRNA(-CA) gene was produced. Purification was carried out using a MinElute PCR Purification kit (QIAGEN).

Next, tRNA(-CA) was synthesized by a transcription reaction. A reaction solution (100 µL) contained 40 mM Tris-HCl (pH 8.0), 20 mM $MgCl_2$, 5 mM DTT, 4 mM NTP, 20 mM GMP, 2 mM spermidine, 10 µg/mL BSA, a ribonuclease inhibitor (40 units), inorganic pyrophosphatase (1 unit), T7 RNA polymerase (400 units), and the tRNA(-CA) gene (10 µg). The reaction solution was subjected to a reaction at 37° C. for 18 hours. tRNA(-CA) was purified by a DEAE-cellulose column (Whatman).

Subsequently, 5× Ligation Buffer (275 mM Hepes-Na pH 7.5, 75 mM $MgCl_2$, 16.5 mM DTT, and 5 mM ATP) (4 µL), 200 µM tRNA(-CA) (2.5 µL), a DMSO solution containing BODIPY FL-aminophenylalanine-pdCpA (2 µL), 0.1% BSA (0.4 µL), T4 RNA Ligase (25 units/µL) (1.2 µL), and water (9.9 µL) were mixed and subjected to a reaction at 4° C. for 2 hours. 3M AcOK (pH 4.5, 10 µL) and water (70 µL) were added thereto. Phenol/chloroform (=1/1) (saturated with 0.3 M AcOK, pH 4.5) was added in a volume equal to that of the resultant, followed by agitation and centrifugation. The upper layer was recovered therefrom and chloroform was added in a volume equal to that of the resultant, followed by agitation and centrifugation. The upper layer was recovered therefrom and ethanol (300 µL) was added thereto. The resultant was lightly mixed and allowed to stand at −20° C. for 1 hour, followed by centrifugation at 15000 rpm and 4° C. for 30 minutes. The supernatant was removed therefrom and 70% EtOH (200 µL) preserved at −20° C. was added thereto, followed by centrifugation at 15000 rpm and 4° C. for 5 seconds. The supernatant was removed therefrom, followed by drying under reduced pressure. The resultant was dissolved in 1 mM potassium acetate (pH 4.5, 2 µL).

EXAMPLE 2

Evaluation of Introduction of Fluorescent-Labeled Amino Acid

A reaction solution (10 µL) was mixed with 55 mM Hepes-KOH (pH 7.5), 210 mM potassium glutamate, 6.9 mM ammonium acetate, 1.7 mM dithiothreitol, 1.2 mM ATP, 0.28 mM GTP, 26 mM phosphoenolpyruvate, 1 mM spermidine, 1.9% polyethylene glycol-8000, 35 µg/mL folic acid, 12 mM magnesium acetate, 20 types of 0.1 mM amino acids, streptavidin mRNA (in which a stop codon UAG had been introduced into the Tyr83 site) (8 µg/µL, an *E. coli* extract (2 µL) (Promega), and a fluorescent-labeled amino acid-tRNA solution (1 µL). A translation reaction was carried out at 37° C. for 1 hour.

Water (9 µL) and 2× sample buffer (10 µL) were added to a translation reaction solution (1 µL), followed by heating at 95° C. for 5 minutes. The resultant was collected in an amount of 5 µL so as to be subjected to 15% SDS-PAGE. The obtained electrophoresis gel was observed with a fluorescence scanner (FMBIO-III, Hitachi Software Engineering Co., Ltd.). The introduction of fluorescent-labeled amino acid was observed (488 nm excitation/520 nm detection). The introduction efficiency was quantified. In addition, with the use of the same electrophoresis gel, Western blot analysis was carried out using an anti-T7tag antibody (Novagen).

The mRNA sequence of streptavidin obtained by substituting the Tyr83 site with UAG (SEQ ID NO: 33) is shown below. The sequence ranges from a start codon to the original stop codon. The underlined part corresponds to the inserted stop codon.

AUGGCUAGCAUGACUGGUGGACAGCAAAUGGGUACCGAAUUCCAUAUG

GACCCGUCCAAGGACUCCAAAGCUCAGGUUUCUGCAGCCGAAGCUGGU

AUCACUGGCACCUGGUAUAACCAACUGGGGUCGACUUUCAUUGUGACC

GCUGGUGCGGACGGAGCUCUGACUGGCACCUACGAAUCUGCGGUUGGU

AACGCAGAAUCCCGCUACGUACUGACUGGCCGUUAUGACUCUGCACCU

GCCACCGAUGGCUCUGGUACCGCUCUGGGCUGGACUGUGGCUUGGAAA

```
-continued
AACAACUAGCGUAAUGCGCACAGCGCCACUACGUGGUCUGGCCAAUAC

GUUGGCGGUGCUGAGGCUCGUAUCAACACUCAGUGGCUGUUAACAUCC

GGCACUACCGAAGCGAAUGCAUGGAAAUCGACACUAGUAGGUCAUGAC

ACCUUUACCAAAGUUAAGCCUUCUGCUGCUAGCAUUGAUGCUGCCAAG

AAAGCAGGCGUAAACAACGGUAACCCUCUAGACGCUGUUCAGCAACAC

CACCACCACCACCACUAA
```

EXAMPLE 3

Introduction of Fluorescent-Labeled Amino Acid into UAG with the Use of an *E. coli*-Derived Mutant tRNA 22 types of tRNAs each having an *E. coli*-derived tRNA sequence and comprising CUA as an anticodon as a result of substitution were produced according to the method described in Example 1. Subsequently, the introduction of fluorescent-labeled amino acid was evaluated by the method described in Example 2.

Figure 4:
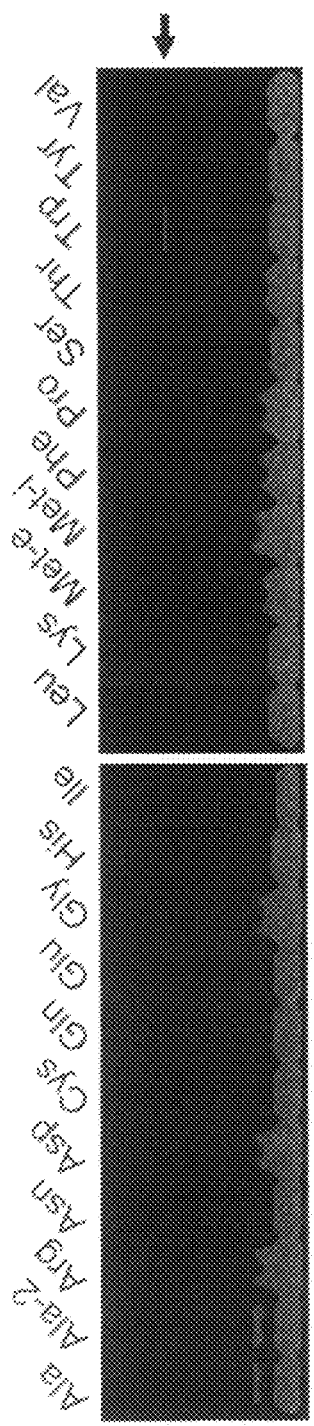
FIG. 4 shows a fluorescence image of SDS-PAGE in the case involving the addition of tRNA having a fluorescent-labeled amino acid. The image indicates the results of introduction of fluorescent-labeled amino acid into UAG with the use of an *E. coli*-derived mutant tRNA.
Figure 5:
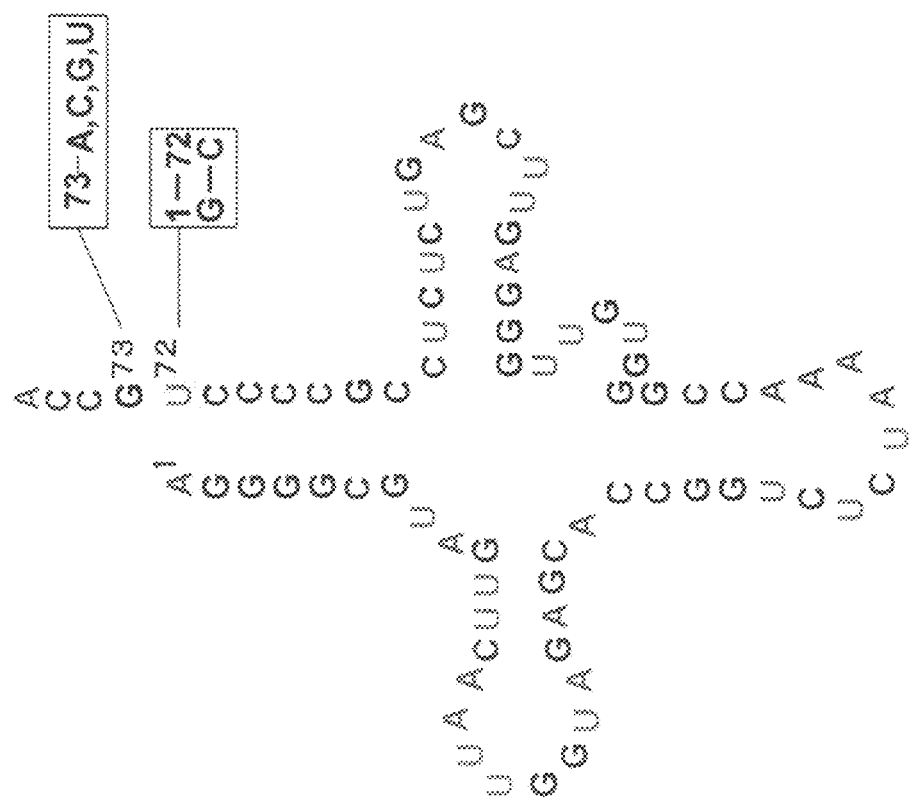
FIG. 5 shows the structure of a mutant tRNA for *E. coli*-derived tryptophan.

FIG. 4 is a fluorescence image of SDS-PAGE in the case involving the addition of tRNA to which fluorescent-labeled amino acid was added. As shown in FIG. 4, it was found that tRNA for tryptophan is appropriately selected from among *E. coli* tRNAs for the introduction of an unnatural amino acid.

Figure 6A:
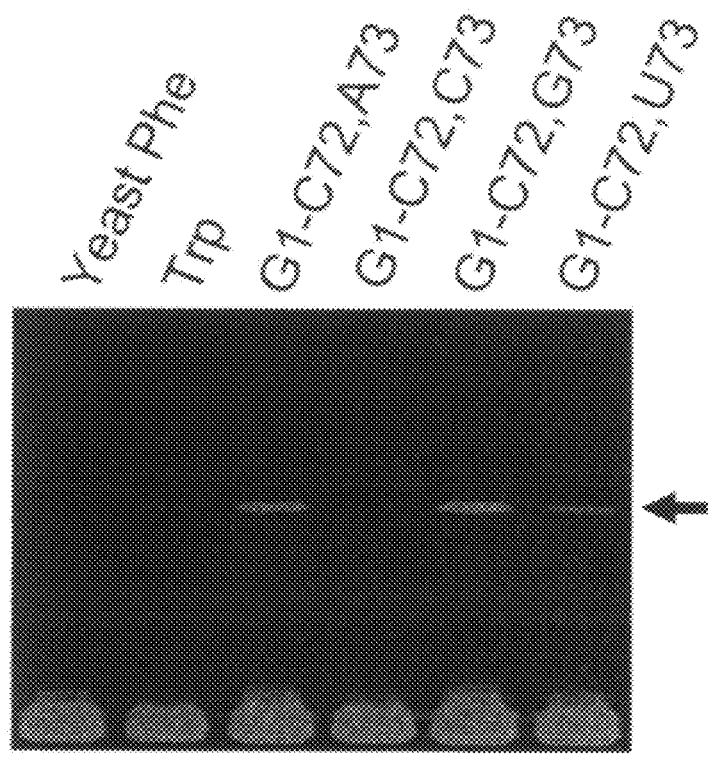
FIG. 6A is an image showing the results of fluorescence imaging of SDS-PAGE in the case involving the use of tRNA to which no fluorescent-labeled amino acid was added. The image indicates the results of introduction of fluorescent-labeled amino acid into UAG with the use of a mutant tRNA for *E. coli*-derived tryptophan.
Figure 6B:
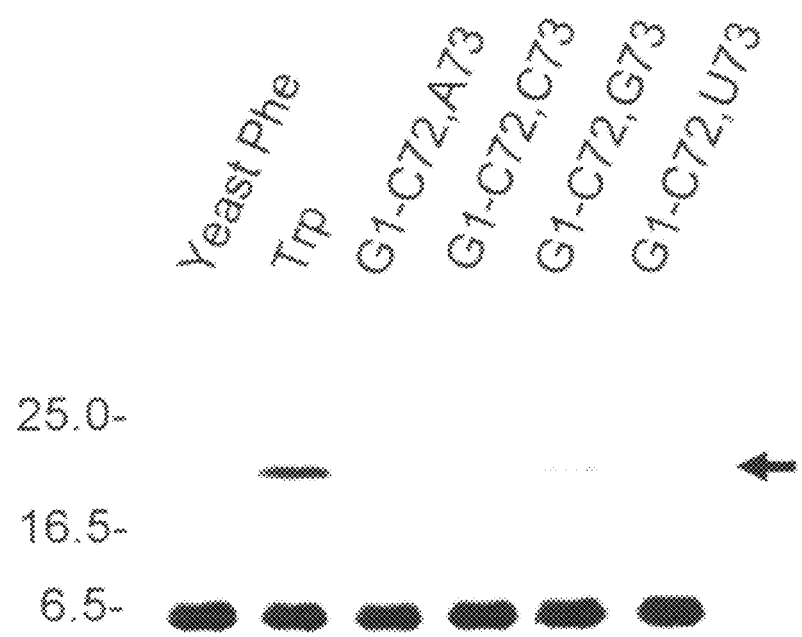
FIG. 6B is an image showing the results of Western blotting in the case involving the use of tRNA having a fluorescent-labeled amino acid. The image indicates the results of introduction of fluorescent-labeled amino acid into UAG with the use of a mutant tRNA for *E. coli*-derived tryptophan.
Figure 7A:
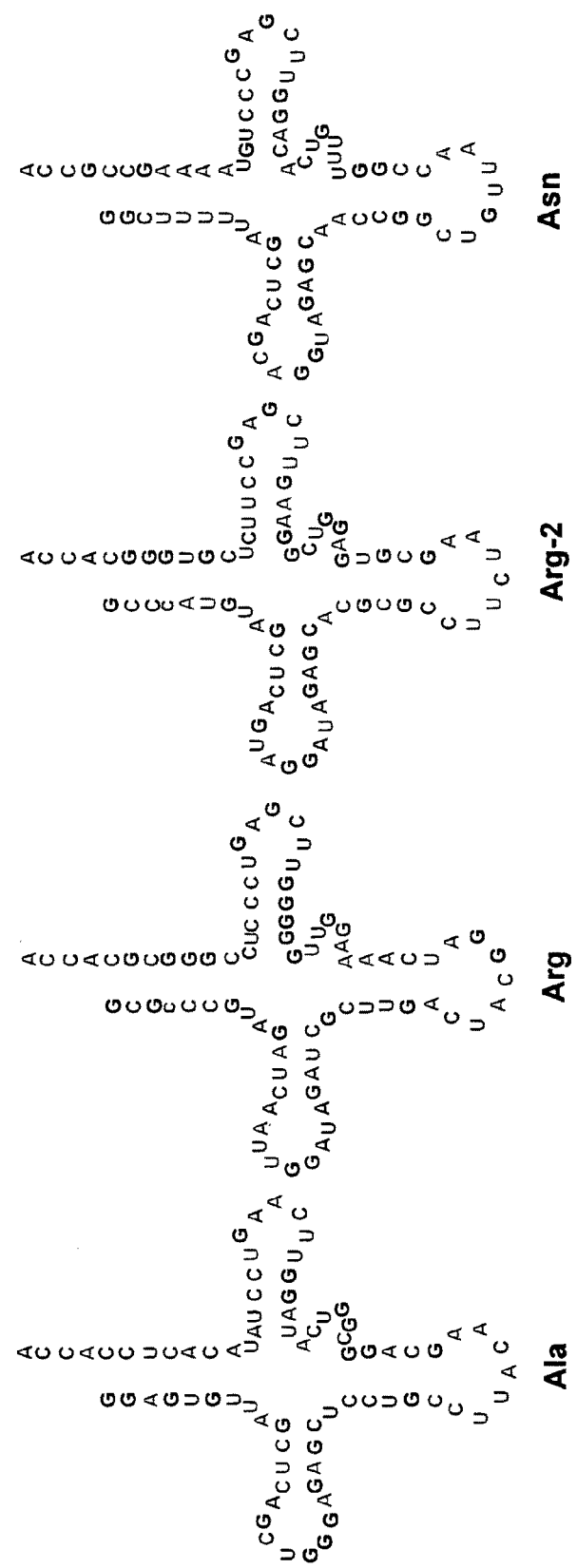
FIG. 7A shows the structures of *Mycoplasma capricolum*-derived tRNAs.
Figure 7B:
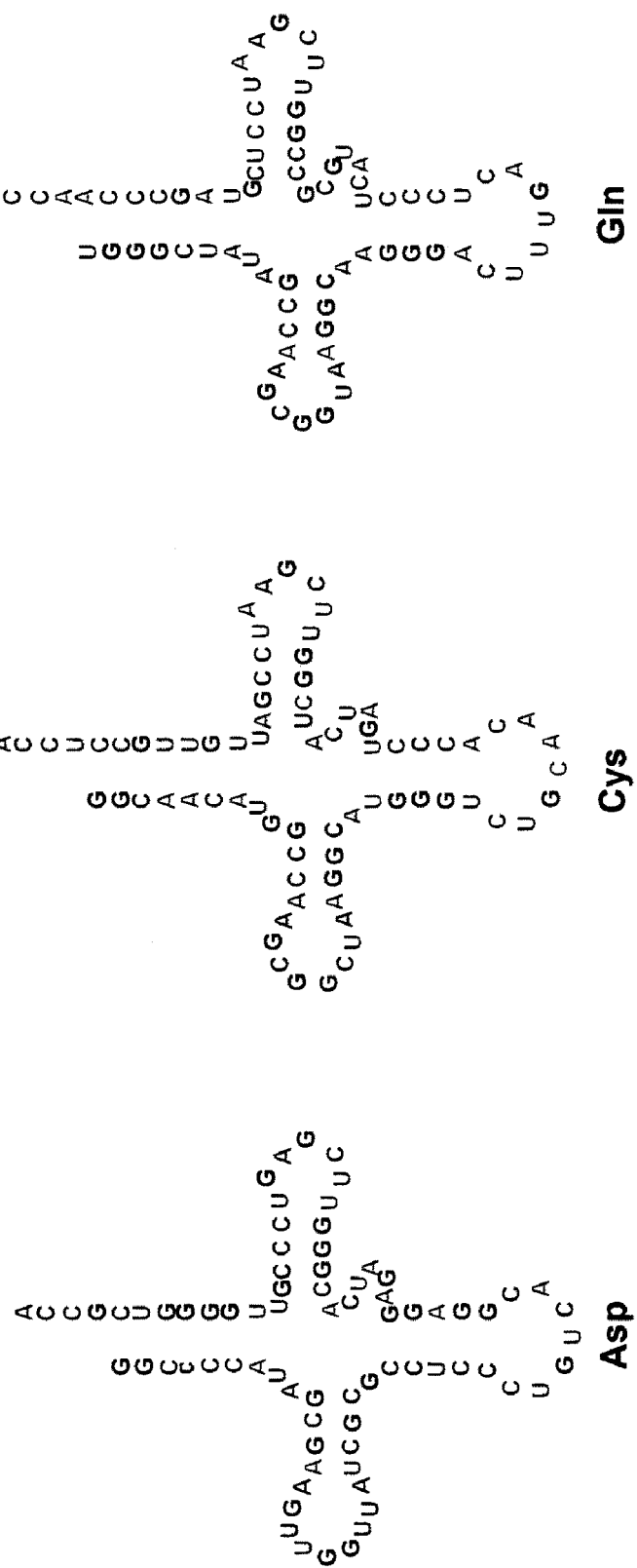
FIG. 7B shows the structures of *Mycoplasma capricolum*-derived tRNAs.
Figure 7C:
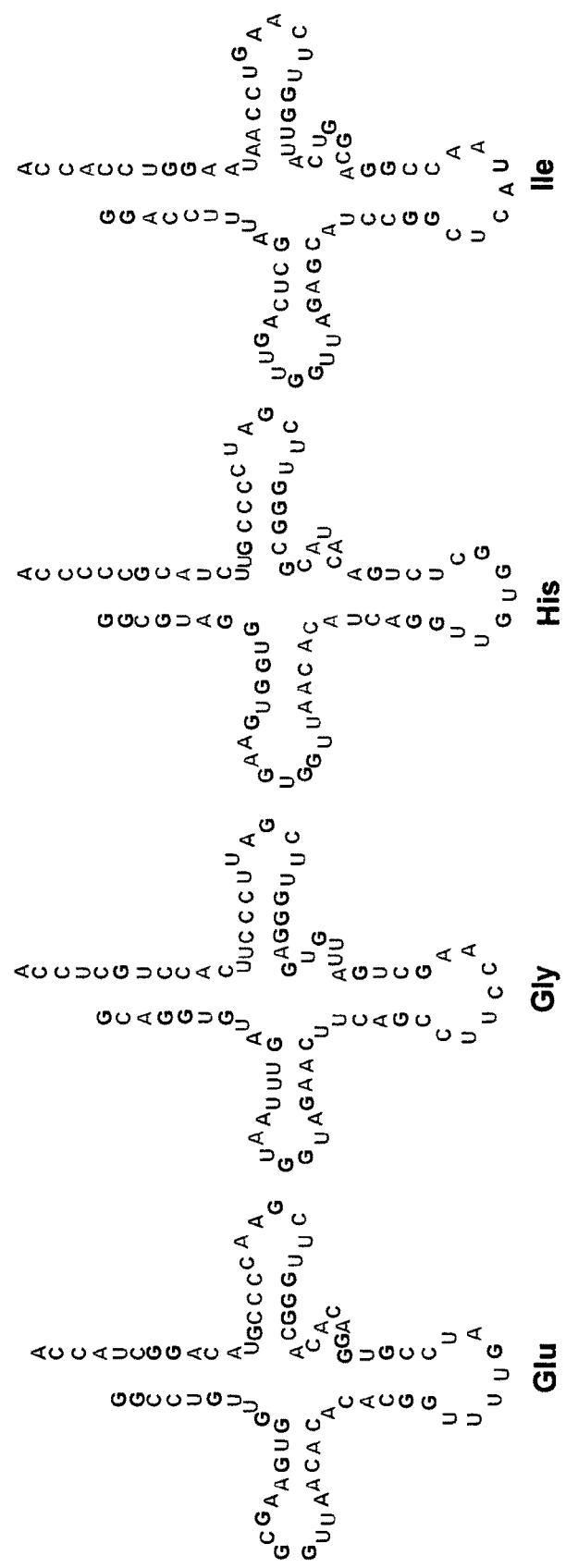
FIG. 7C shows the structures of *Mycoplasma capricolum*-derived tRNAs.
Figure 7D:
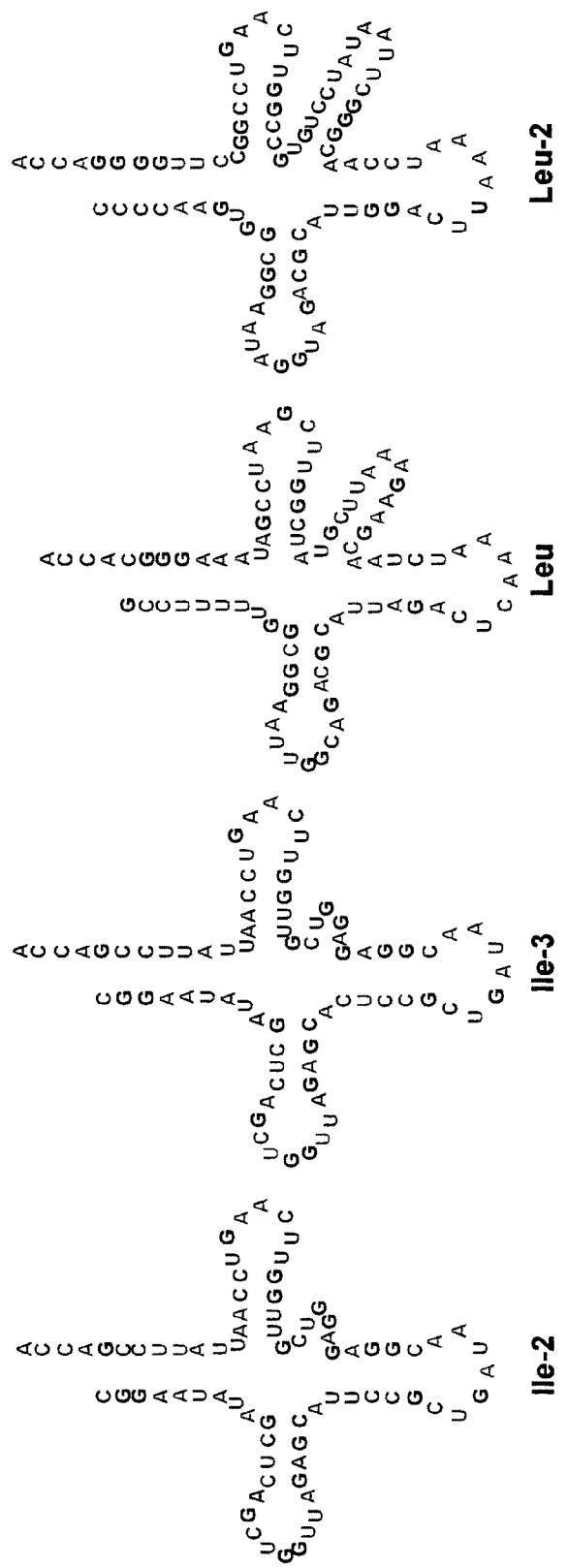
FIG. 7D shows the structures of *Mycoplasma capricolum*-derived tRNAs.
Figure 7E:
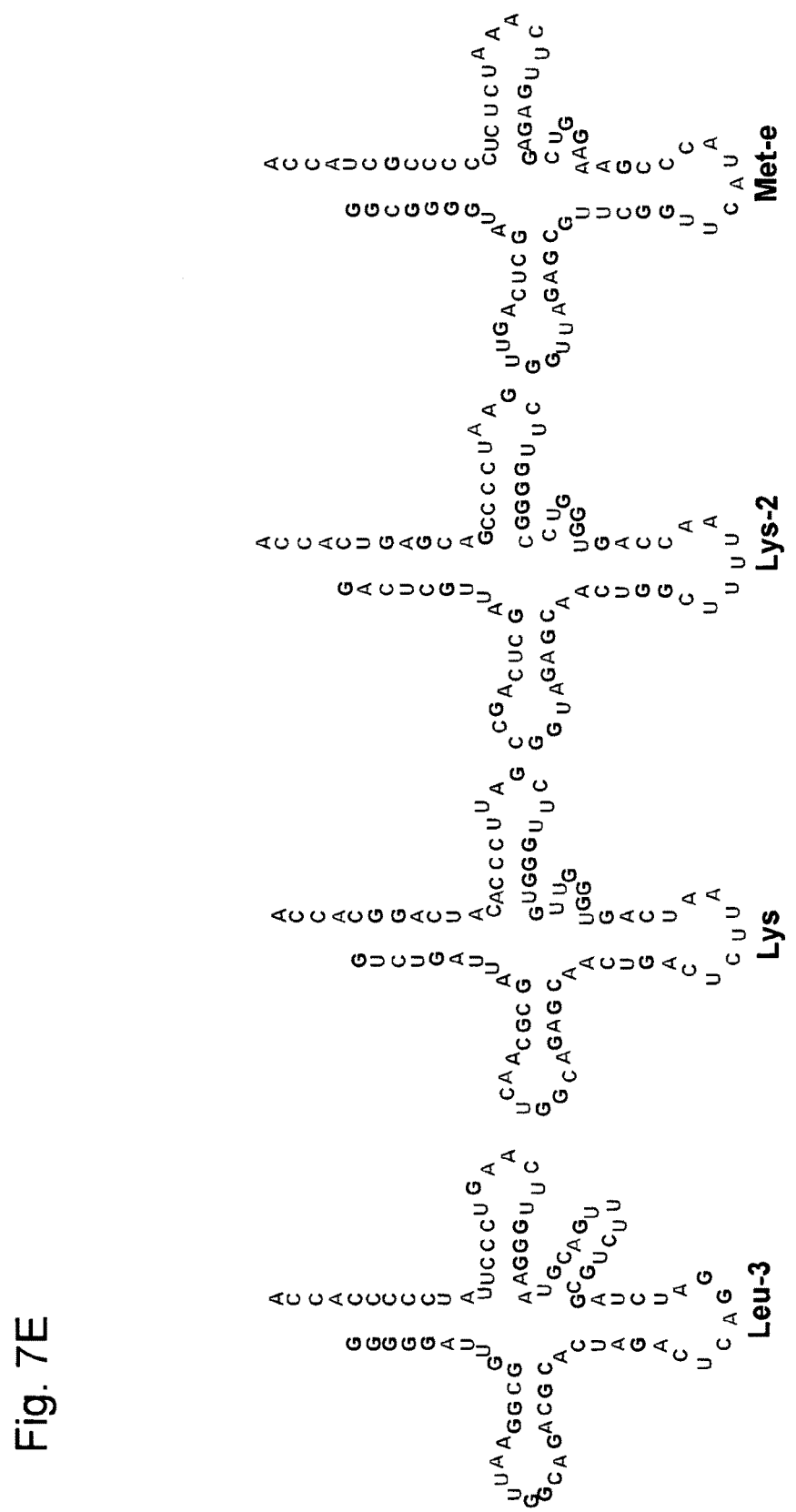
FIG. 7E shows the structures of *Mycoplasma capricolum*-derived tRNAs.
Figure 7F:
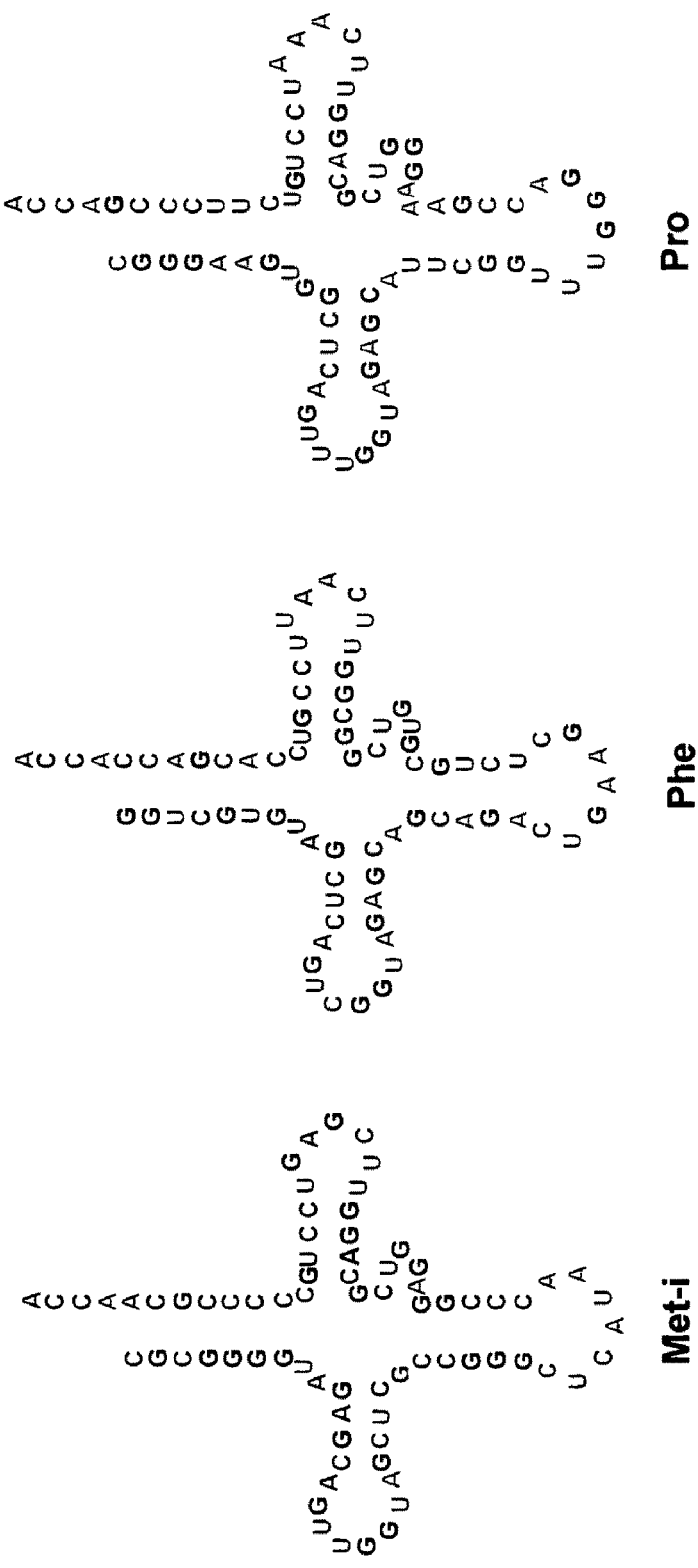
FIG. 7F shows the structures of *Mycoplasma capricolum*-derived tRNAs.
Figure 7G:
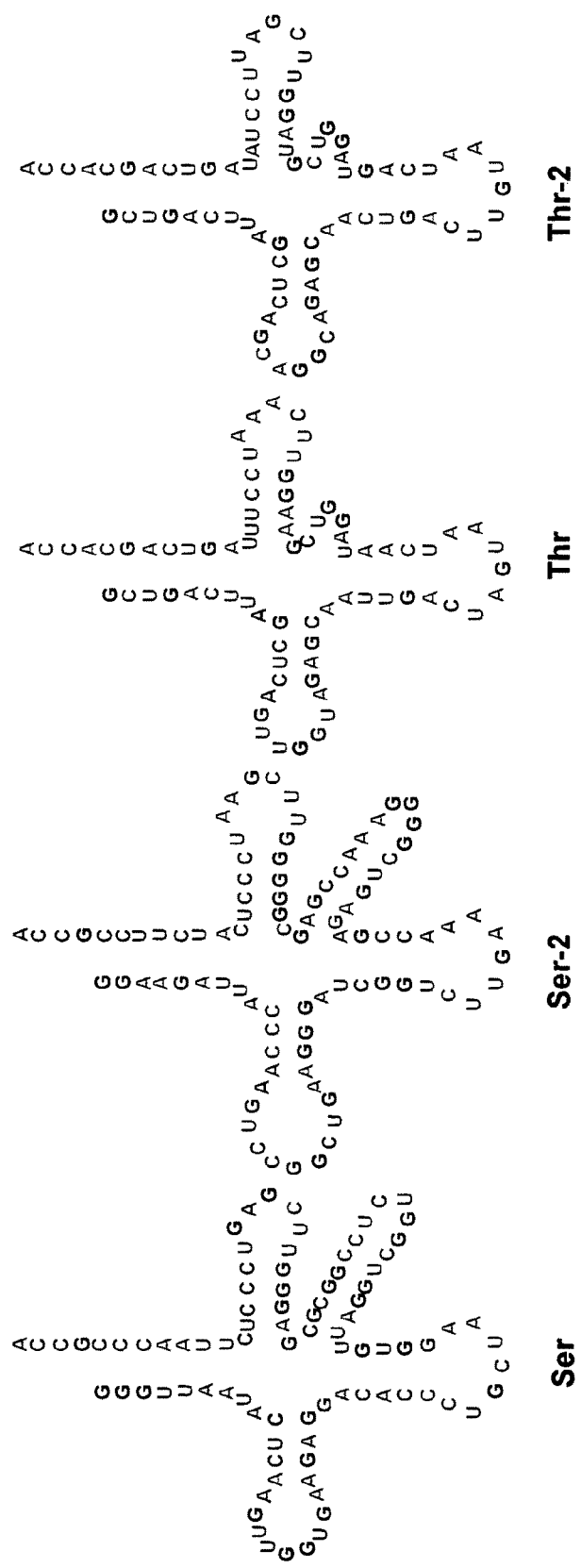
FIG. 7G shows the structures of *Mycoplasma capricolum*-derived tRNAs.
Figure 7H:
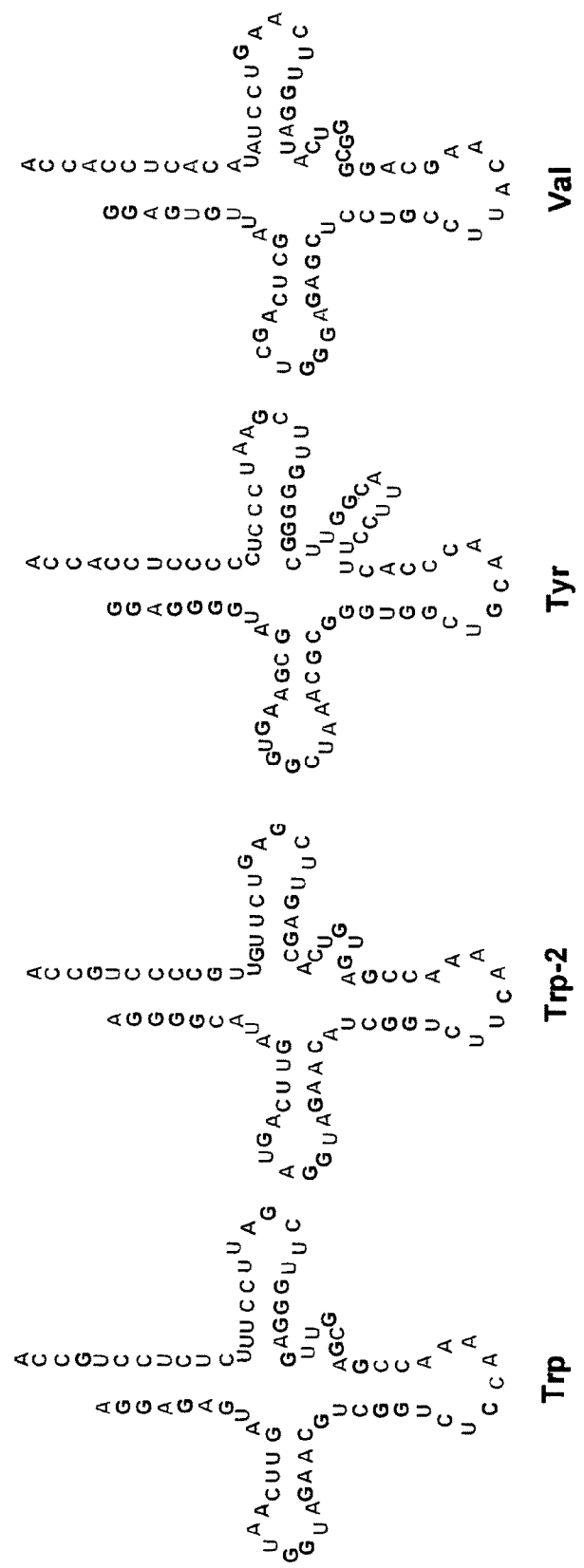
FIG. 7H shows the structures of *Mycoplasma capricolum*-derived tRNAs.

FIG. 6A shows the results of Western blotting in the case involving the use of tRNA to which no amino acid was added. FIG. 6B is a fluorescence image of SDS-PAGE in the case involving the use of tRNA to which fluorescent-labeled amino acid was added. FIG. 6C shows fluorescence band intensities of proteins subjected to introduction with the use of the individual mutants. As shown in FIGS. 6A to 6C, G1-C72, A73 and G1-C72, G73 had high introduction activity. Note that a full-length protein was produced in the case of G1-C72, G73 even without addition of a fluorescent-labeled unnatural amino acid. Thus, it is considered that a natural amino acid is added in a translation system in such case. Accordingly, G1-C72, A73 to which no natural amino acid is introduced is the most preferable.

EXAMPLE 4

Introduction of Fluorescent-Labeled Amino Acid into UAG with the Use of a *Mycoplasma capricolum*-Derived Mutant tRNA 30 types of tRNAs each having a *Mycoplasma capricolum*-derived tRNA sequence and comprising CUA as an anticodon as a result of substitution were produced by the method described in Example 1. Subsequently, the introduction of fluorescent-labeled amino acid was evaluated by the method described in Example 2.

Figure 8:
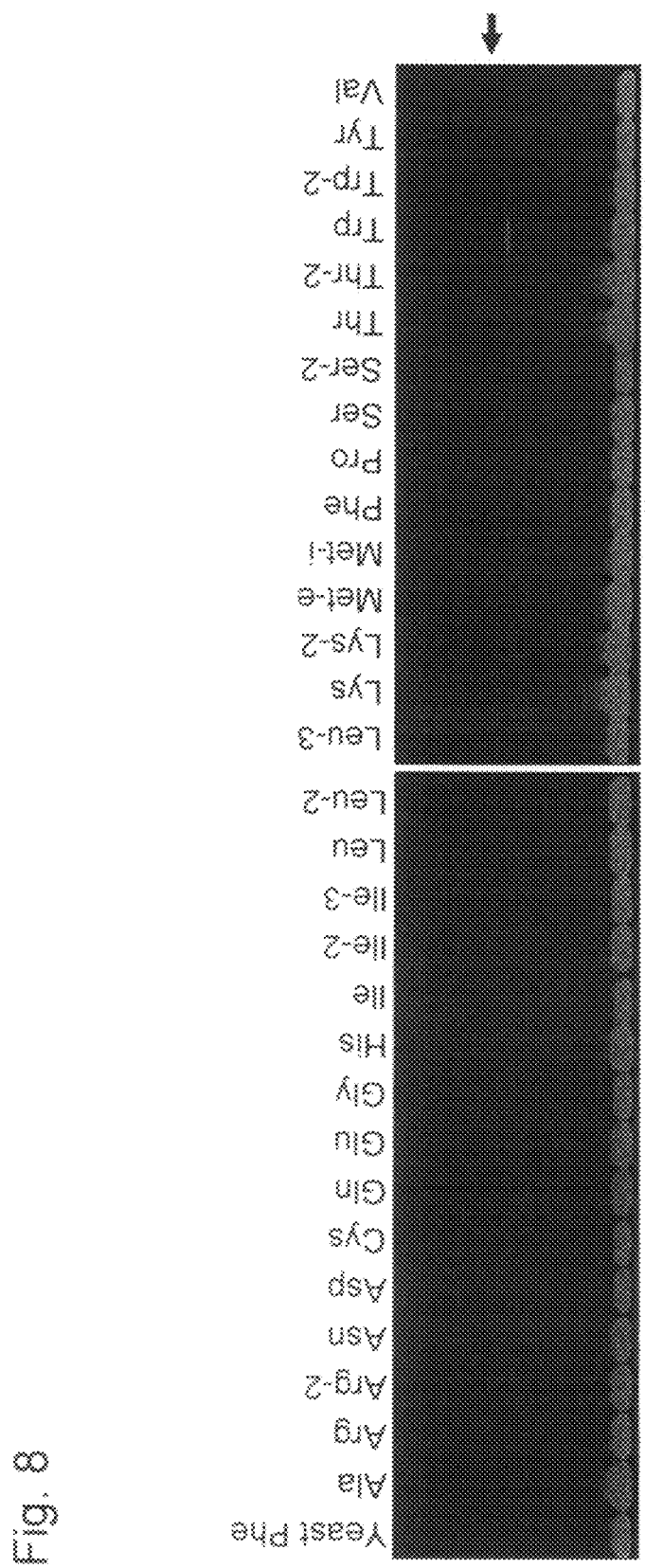
FIG. 8 is an image showing the results of introduction of fluorescent-labeled amino acid into UAG with the use of a *Mycoplasma capricolum*-derived mutant tRNA.
Figure 9:
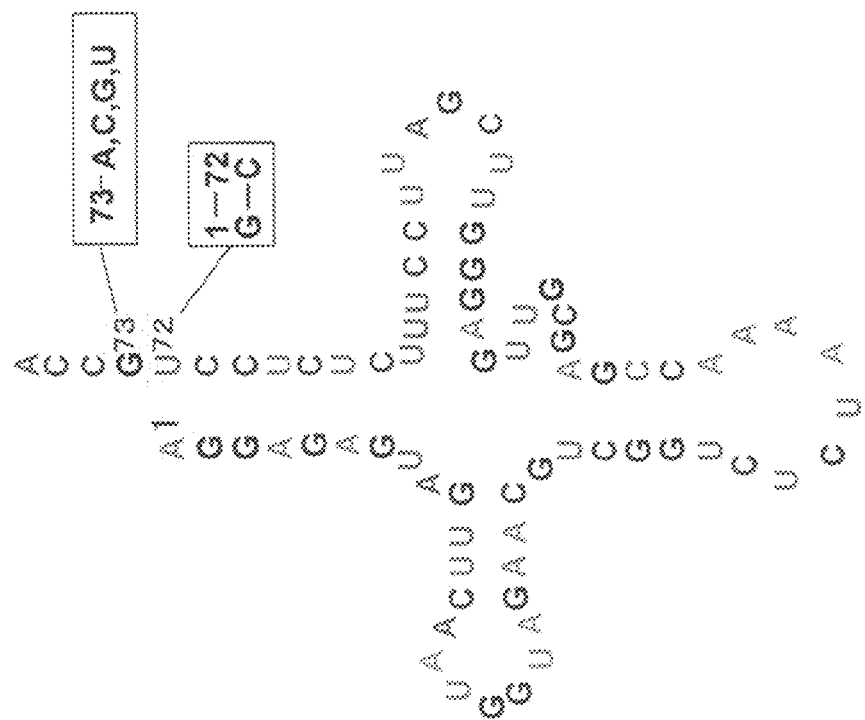
FIG. 9 shows the structure of a m

FIG. 8 shows the results of introduction of fluorescent-labeled amino acid into UAG with the use of a *Mycoplasma capricolum*-derived mutant tRNA. As shown in FIG. 8, it was found that tRNA for tryptophan is appropriately selected from among *Mycoplasma capricolum*-derived mutant tRNAs for the introduction of unnatural amino acid.

Figure 10A:
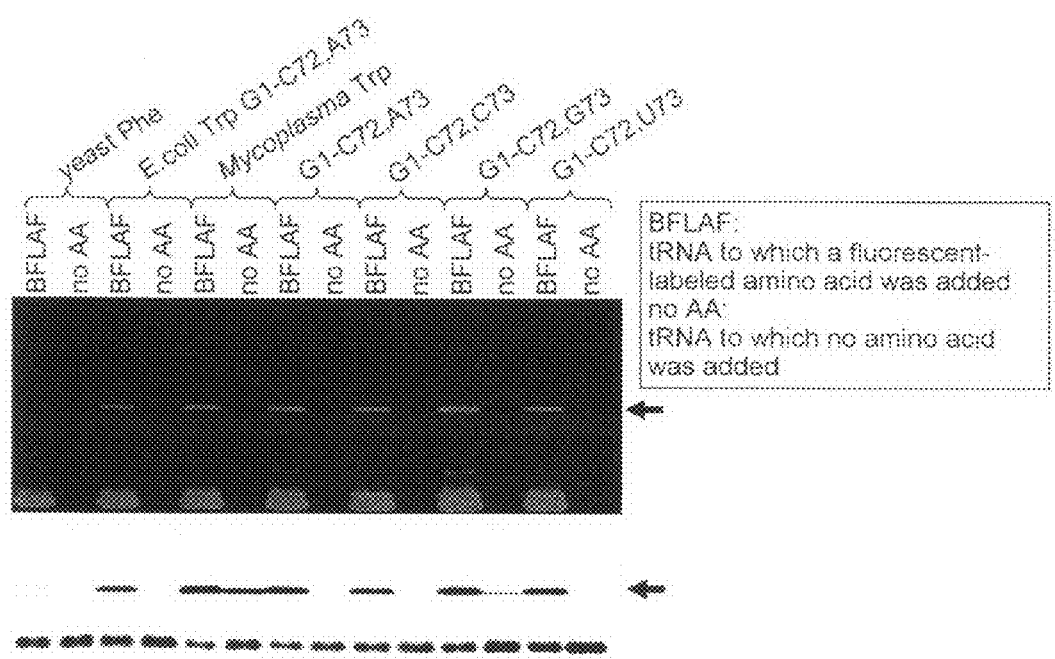
Figure 10B:
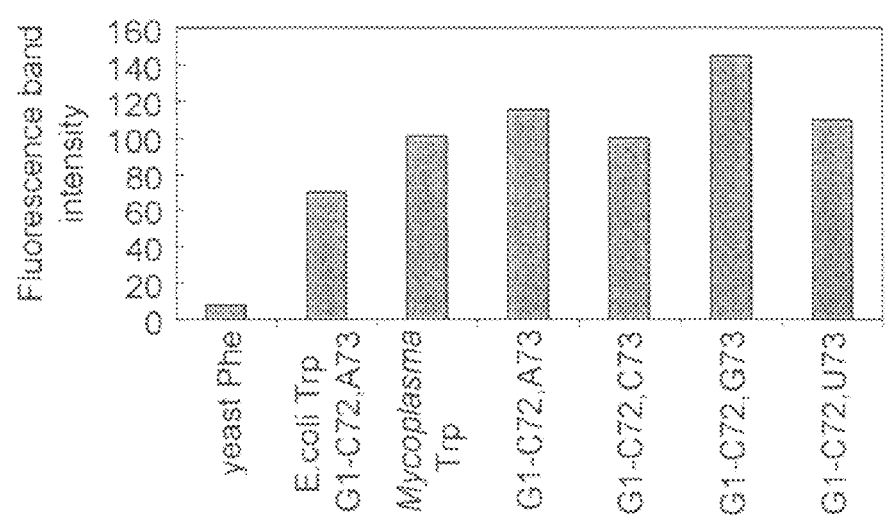

FIG. 10A shows a fluorescence image in the case involving the use of tRNAs to which no amino acid was added and tRNAs to which fluorescent-labeled amino acid was added. FIG. 10B shows fluorescence band intensities of proteins subjected to introduction with the use of individual mutants. As shown in FIGS. 10A and 10B, all *Mycoplasma capricolum*-derived mutant tRNAs showed introduction activity at higher levels than that of a mutant tRNA (a mutant G1-C72, A73) for *E. coli* tryptophan. G1-C72, A73 from which substantially no full-length protein is generated without the addition of fluorescent-labeled amino acid is particularly preferable.

EXAMPLE 5

Figure 11A:
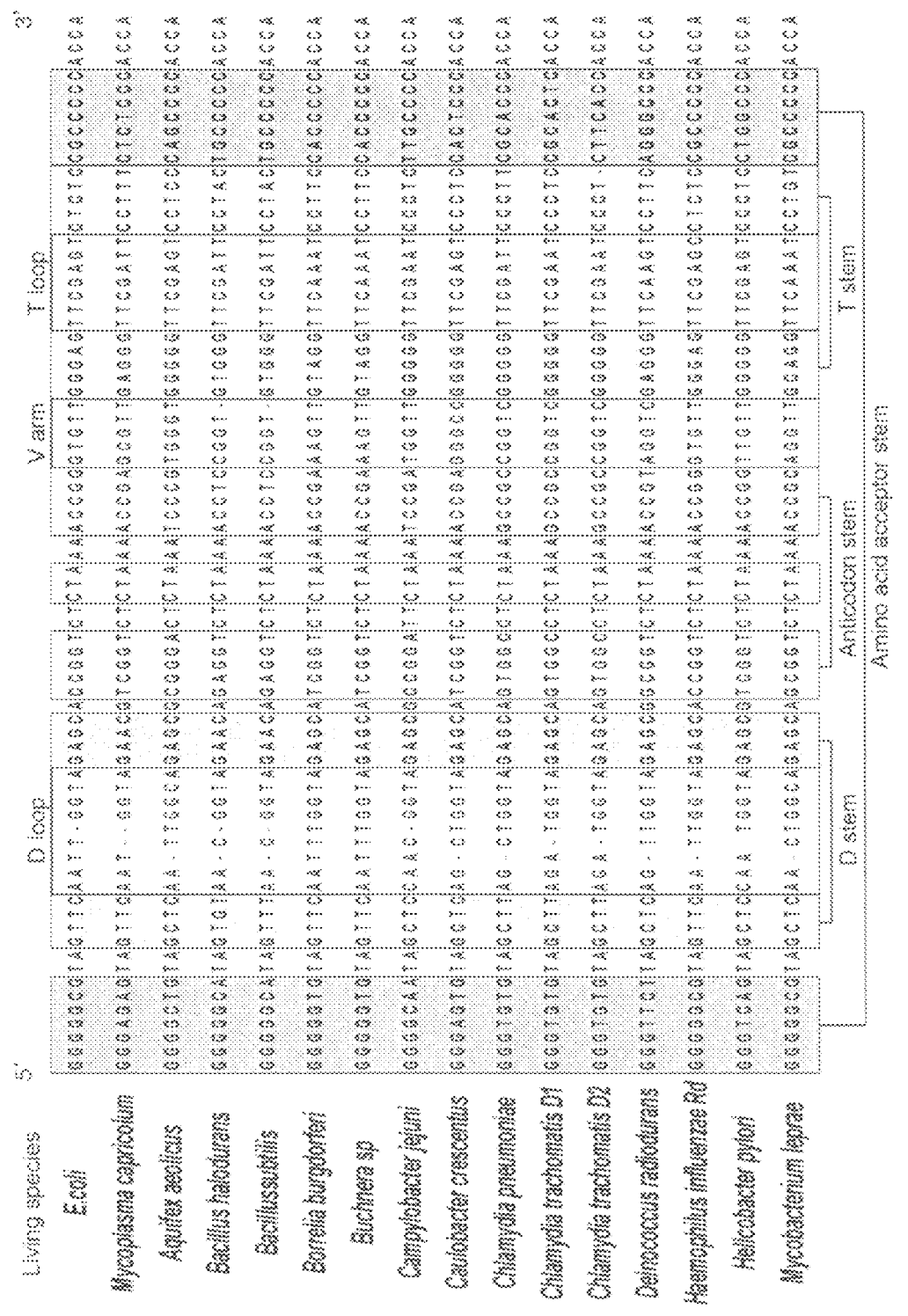
Figure 11B:
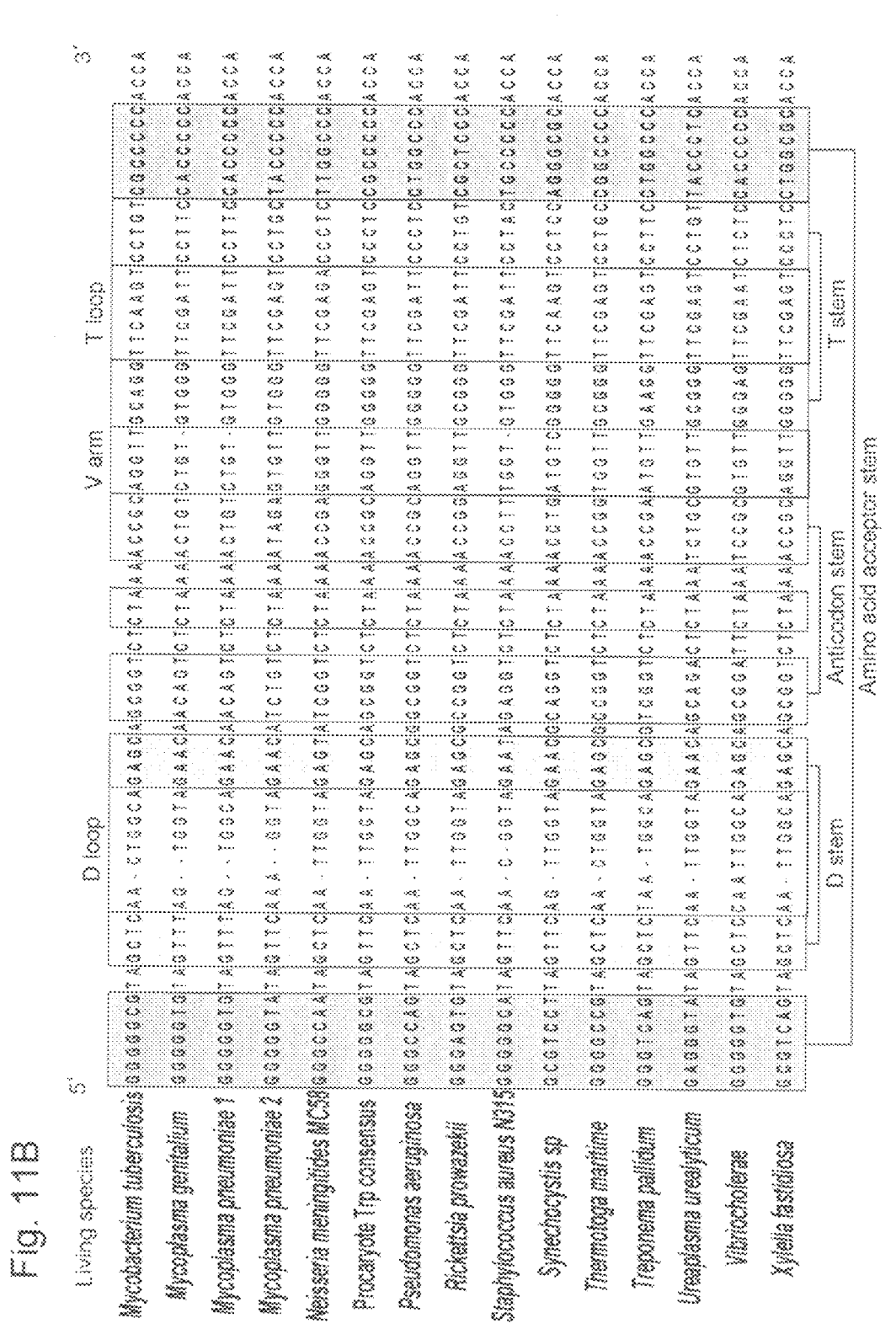

Introduction of Fluorescent-Labeled Amino Acid into UAG with the Use of a Mutant tRNA (a Mutant G1-C72, A73) for Tryptophan Derived from a Different Organism 31 types of tRNAs each having a sequence of tRNA for tryptophan derived from a different organism and comprising CUA as an anticodon as a result of substitution caused by introduction of a mutant G1-C72, A73 were produced by the method described in Example 1. Subsequently, the introduction of fluorescent-labeled amino acid was evaluated by the method described in Example 2. FIGS. 11A and 11B show sequences of 31 types of mutant tRNAs (SEQ ID NOS: 1 to 31) each having CUA as an anticodon as a result of substitution caused by introduction of tRNA (G1-C72, A73) for tryptophan derived from a different organism. In FIGS. 11A and 11B, "U" is expressed as "T." In addition, the $73^{rd}$ base is "A" in SEQ ID NOS: 1 to 31. Alternatively, the effects of the present invention can be obtained when "G" replaces "A" (G1-C72, G73).

Figure 12A:
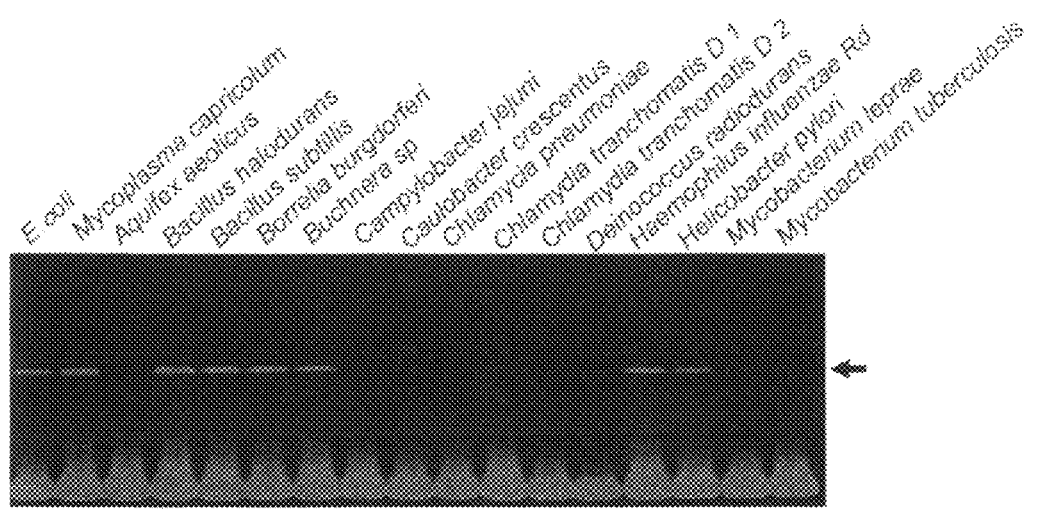
Figure 12B:
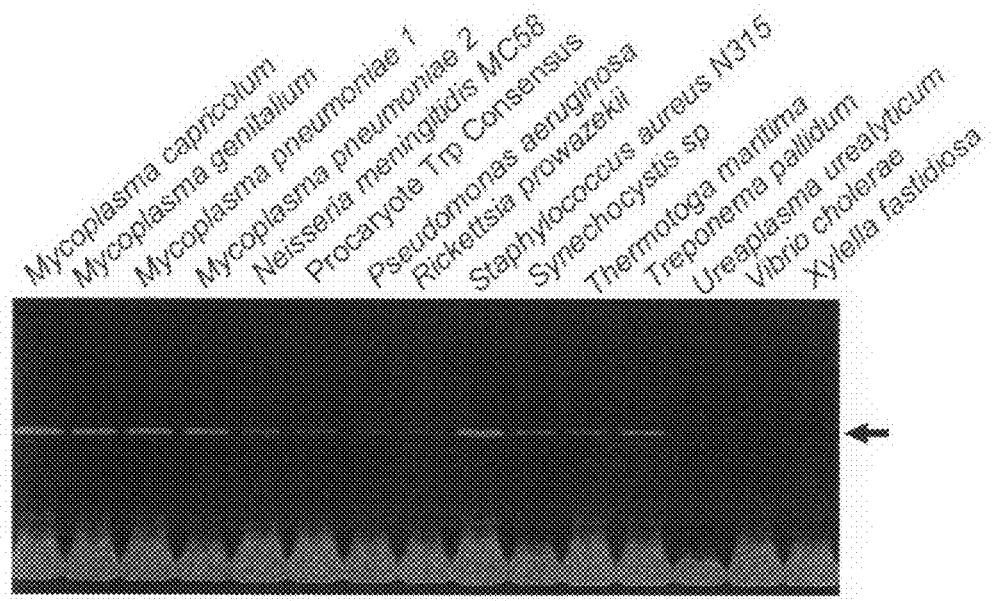

FIGS. 12A and 12B show the results of introduction of fluorescent-labeled amino acid into UAG with the use of a mutant tRNA (G1-C72, A73) for tryptophan derived from a different organism.

Figure 13B:
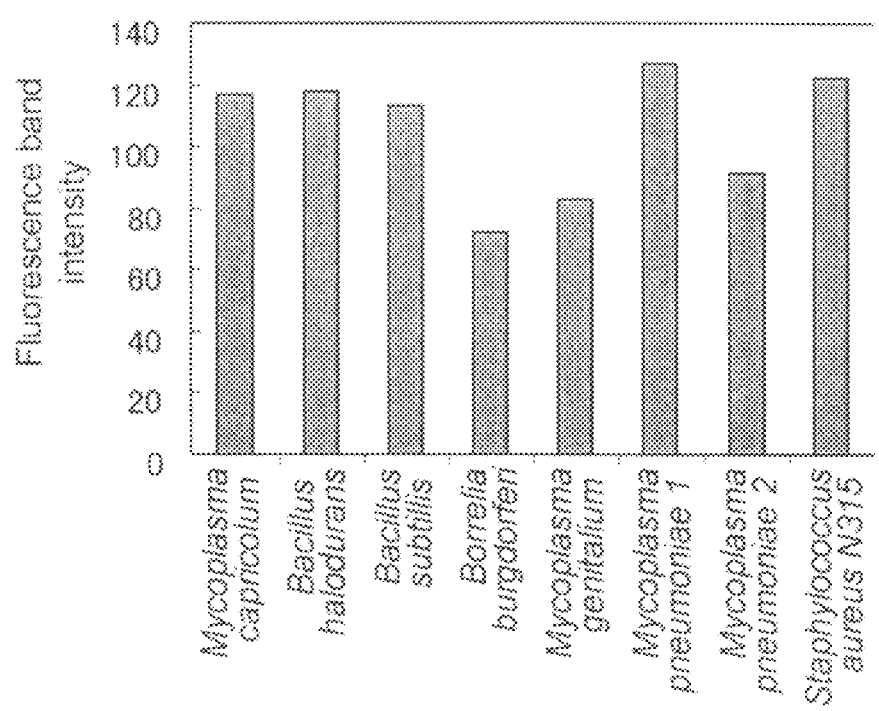

FIG. 13A shows the results of fluorescence imaging in the case involving the use of tRNA to which no amino acid was added and tRNA to which fluorescent-labeled amino acid was added. FIG. 13B shows fluorescence band intensities of proteins subjected to introduction of individual mutants. As shown in FIGS. 13A and 13B, 8 types of tRNAs for tryptophan, including tRNA for *Mycoplasma capricolum*-derived tryptophan, exhibited high levels of introduction activity. Among them, a *Mycoplasma capricolum*-derived mutant tRNA (a G1-C72, A73 mutant), which is unlikely to cause generation of a full-length protein to which no fluorescent-labeled amino acid is added, is the most preferable.

EXAMPLE 6

Double Introduction of Fluorescent-Labeled Amino Acids into Maltose Binding Protein (MBP)

(1) Introduction Only by the 4-Base Codon Method

With the use of tRNA for yeast phenylalanine, BODIPY FL-aminophenylalanine-tRNA (having ACCC as an anticodon) and BODIPY 558/568-aminophenylalanine-tRNA (having CCCG as an anticodon) were produced by the method described in Example 1. Subsequently, with the use of mRNA of maltose binding protein (such mRNA having CGGG at the N terminal and GGGU at the C terminal), double introduction of fluorescent-labeled amino acids was carried out by the method described in Example 2. Note that detection of fluorescence in electrophoresis gel was carried out at 488 nm excitation/520 nm detection and, in addition, at 532 nm excitation/605 nm detection.

Figure 14A:
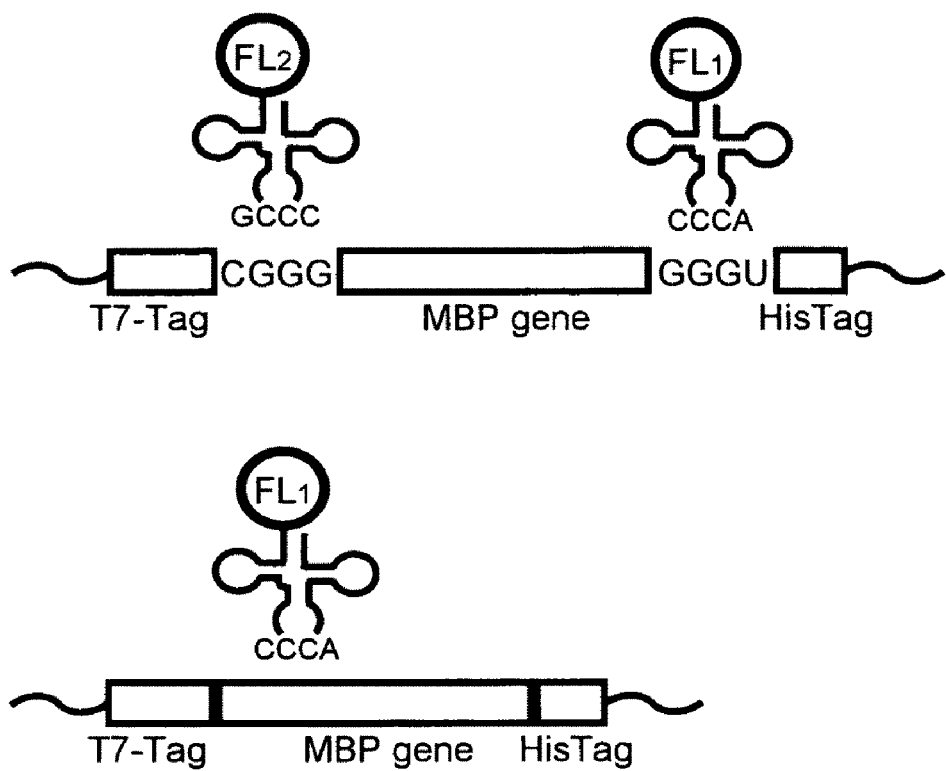
Figure 14B:
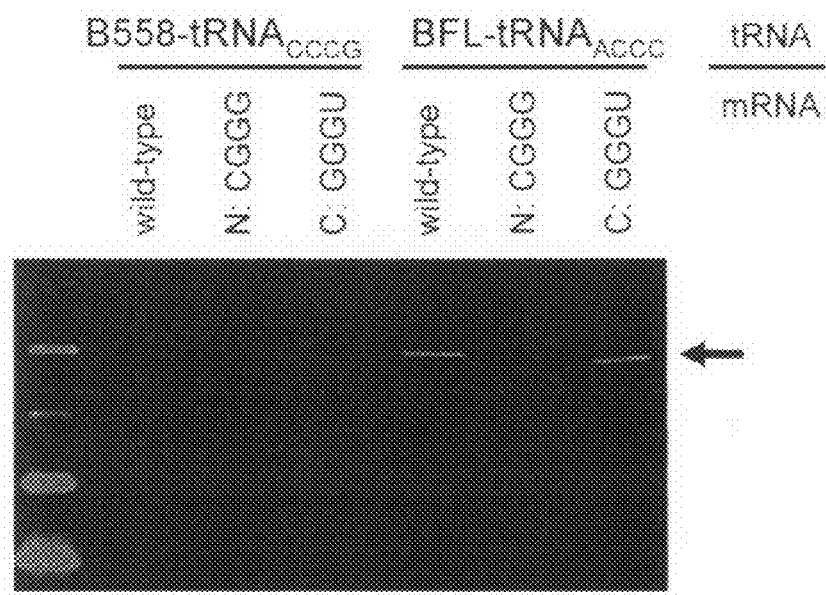

FIG. 14A shows an outline of a method for double introduction of fluorescent-labeled amino acids into maltose binding protein (MBP) based on the 4-base codon method. FIG.

14B shows the results of double introduction of fluorescent-labeled amino acids into maltose binding protein (MBP) based on the 4-base codon method. tRNA having CCCG introduced fluorescent-labeled amino acids exclusively into the gene having CGGG. Meanwhile, tRNA having ACCC also introduced fluorescent-labeled amino acids into the gene having no GGGU. That is, in the case of this gene, fluorescence-labeled amino acid was introduced into a site other than a 4-base codon GGGU. Thus, it was attempted to use a stop codon UAG instead of a 4-base codon.

The mRNA sequence of a maltose binding protein having CGGG at the N terminal and GGGU at the C terminal is shown below (SEQ ID NO: 34). The sequence ranges from a start codon to the original stop codon. The underlined part corresponds to the inserted codon.

AUGGCUAGCAUGACUGGUGGACAGCAAAUGGGUACUCGGGAGUAACGA

AUUCAAAAUCGAAGAAGGUAAACUGGUAAUCUGGAUUAACGGCGAUAA

AGGCUAUAACGGUCUCGCUGAAGUCGGUAAGAAAUUCGAGAAAGAUAC

CGGAAUUAAAGUCACCGUUGAGCAUCCGGAUAAACUGGAAGAGAAAUU

CCCACAGGUUGCGGCAACUGGCGAUGGCCCUGACAUUAUCUUCUGGGC

ACACGACCGCUUUGGUGGCUACGCUCAAUCUGGCCUGUUGGCUGAAAU

CACCCCGGACAAAGCGUUCCAGGACAAGCUGUAUCCGUUUACCUGGGA

UGCCGUACGUUACAACGGCAAGCUGAUUGCUUACCCGAUCGCUGUUGA

AGCGUUAUCGCUGAUUUAUAACAAAGAUCUGCUGCCGAACCCGCCAAA

AACCUGGGAAGAGAUCCCGGCGCUGGAUAAAGAACUGAAAGCGAAAGG

UAAGAGCGCGCUGAUGUUCAACCUGCAAGAACCGUACUUCACCUGGCC

GCUGAUUGCUGCUGACGGGGGUUAUGCGUUCAAGUAUGAAAACGGCAA

GUACGACAUUAAAGACGUGGGCGUGGAUAACGCUGGCGCGAAAGCGGG

UCUGACCUUCCUGGUUGACCUGAUUAAAAACAAACACAUGAAUGCAGA

CACCGAUUACUCCAUCGCAGAAGCUGCCUUUAAUAAAGGCGAAACAGC

GAUGACCAUCAACGGCCCGUGGGCAUGGUCCAACAUCGACACCAGCAA

AGUGAAUUAUGGUGUAACGGUACUGCCGACCUUCAAGGGUCAACCAUC

CAAACCGUUCGUUGGCGUGCUGAGCGCAGGUAUUAACGCCGCCAGUCC

GAACAAAGAGCUGGCAAAAGAGUUCCUCGAAAACUAUCUGCUGACUGA

UGAAGGUCUGGAAGCGGUUAAUAAAGACAAACCGCUGGGUGCCGUAGC

GCUGAAGUCUUACGAGGAAGAGUUGGCGAAAGAUCCACGUAUUGCCGC

CACUAUGGAAAACGCCCAGAAAGGUGAAAUCAUGCCGAACAUCCCGCA

GAUGUCCGCUUUCUGGUAUGCCGUGCGUACUGCGGUGAUCAACGCCGC

CAGCGGUCGUCAGACUGUCGAUGAAGCCCUGAAAGACGCGCAGACUCG

UAUCACCAAGGGGUAGCCACCACCACCACCACUAA (2) Introduction with the Combined Use of the 4-Base Codon Method and the Mutant tRNA of the Present Invention With the use of tRNA for yeast phenylalanine, BODIPY 558/568-aminophenylalanine-tRNA (having CCCG as an anticodon) was produced by the method described in Example 1. Meanwhile, with the use of a mutant tRNA for *Mycoplasma capricolum*-derived tryptophan (a G1-C72, A73 mutant), BODIPY FL-aminophenylalanine-tRNA (having CUA as an anticodon) was produced by the method described in Example 1. Subsequently, with the use of mRNA (having CGGG at the N terminal portion and UAG at the C terminal portion) of a maltose binding protein, double introduction of fluorescent-labeled amino acids was carried out by the method described in Example 2. Note that detection of fluorescence in electrophoresis gel was carried out at 488 nm excitation/520 nm detection and, in addition, at 532 nm excitation/605 nm detection.

Figure 15A:
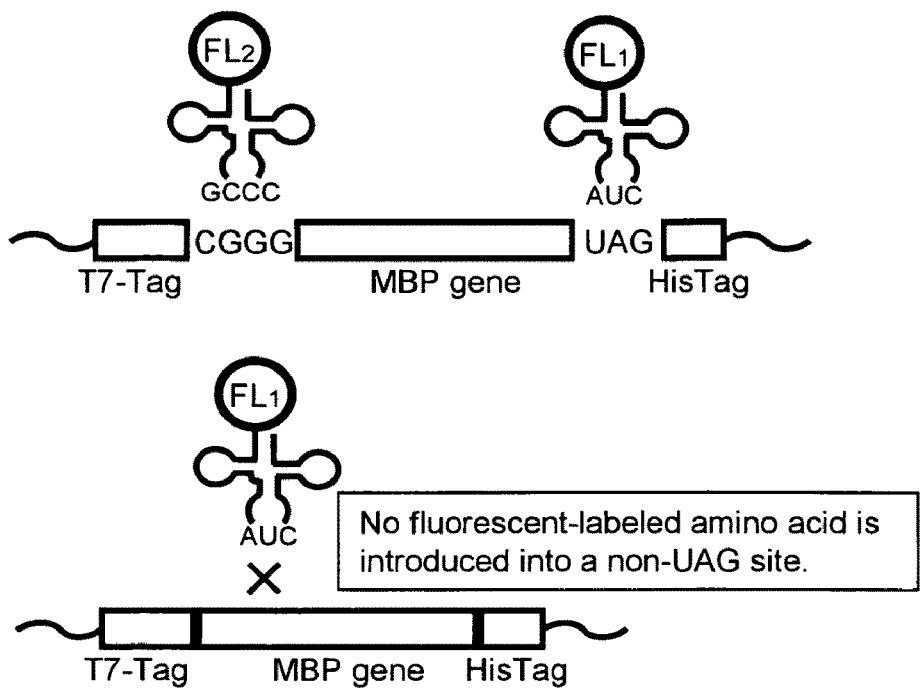
Figure 15B:
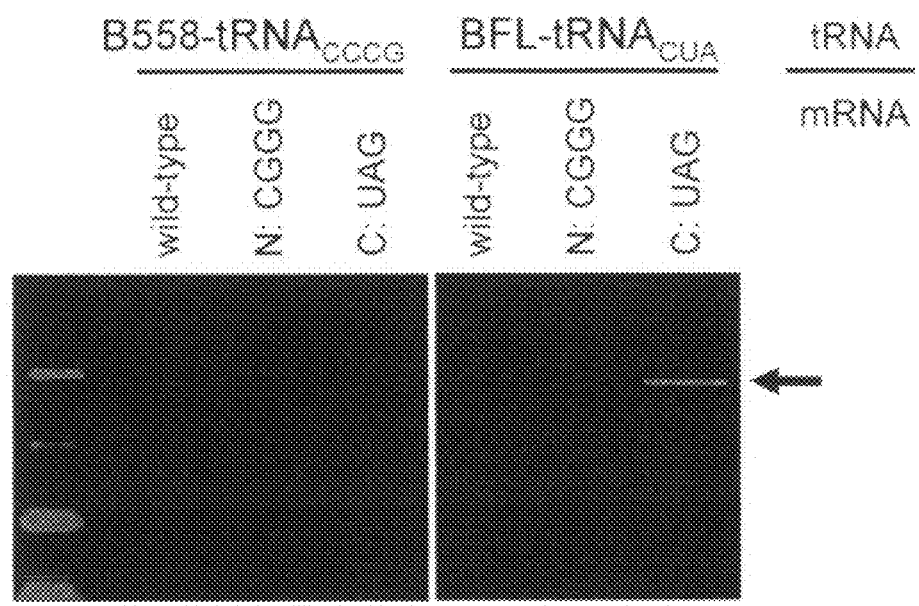
Figure 16A:
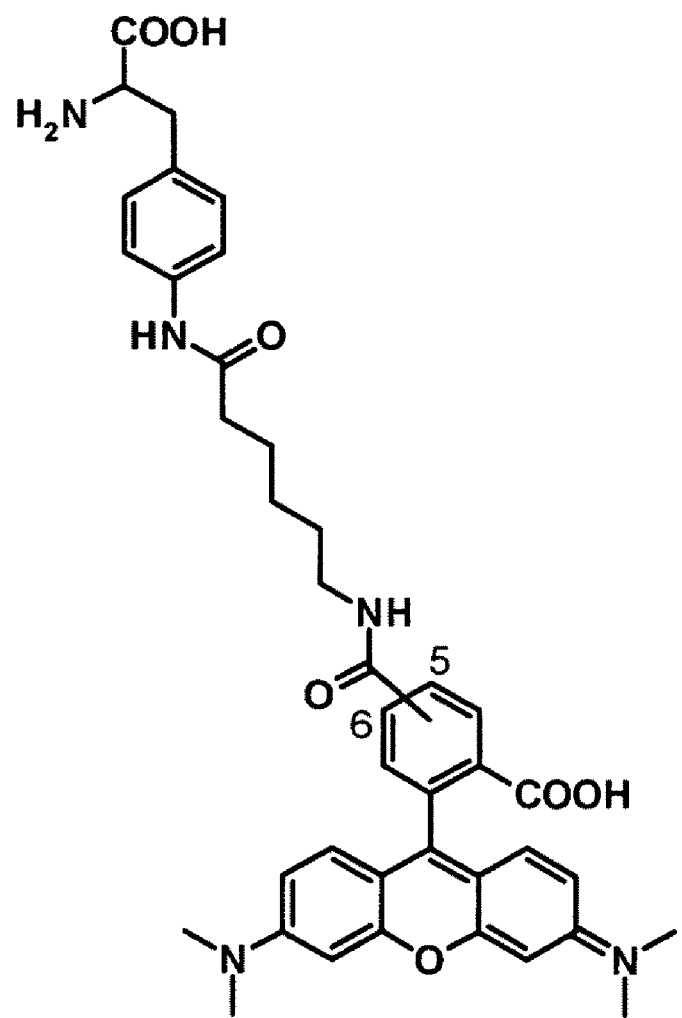
Figure 16B:
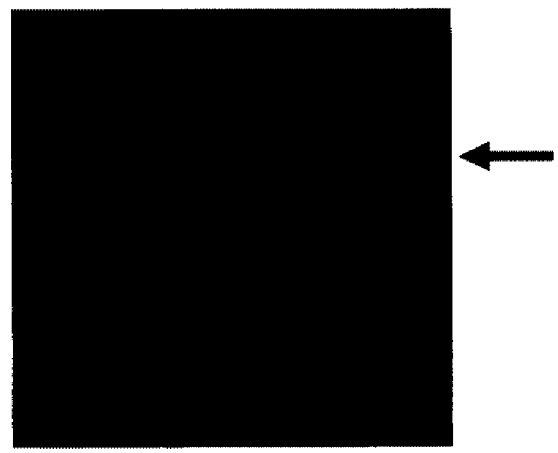
Figure 16C:
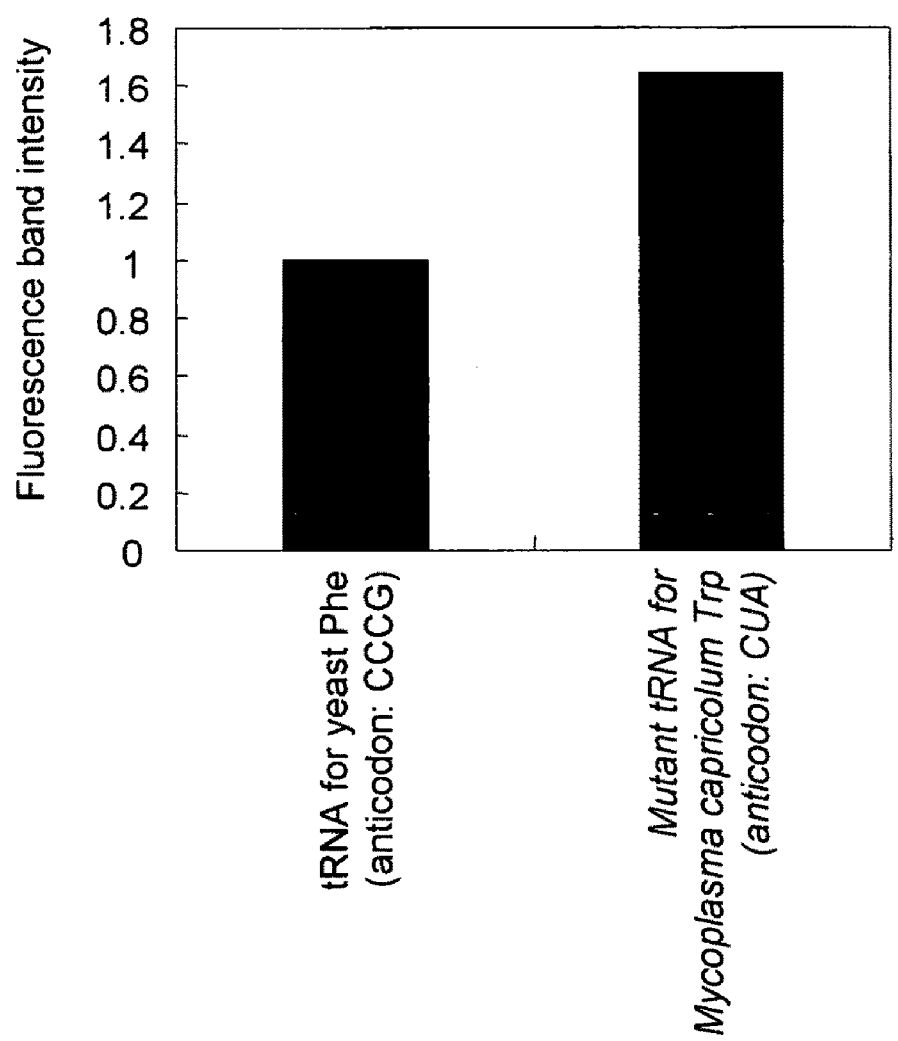
Figure 18A:
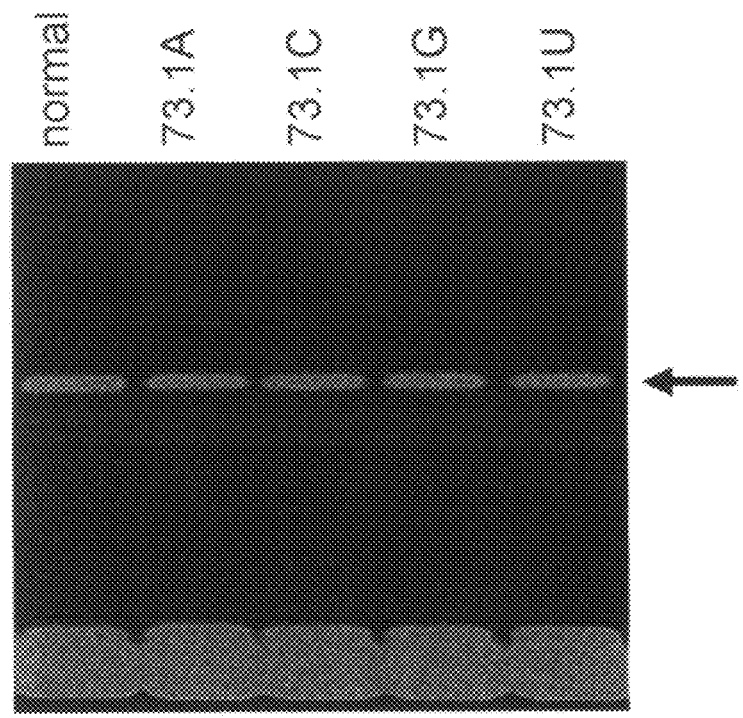
Figure 18B:
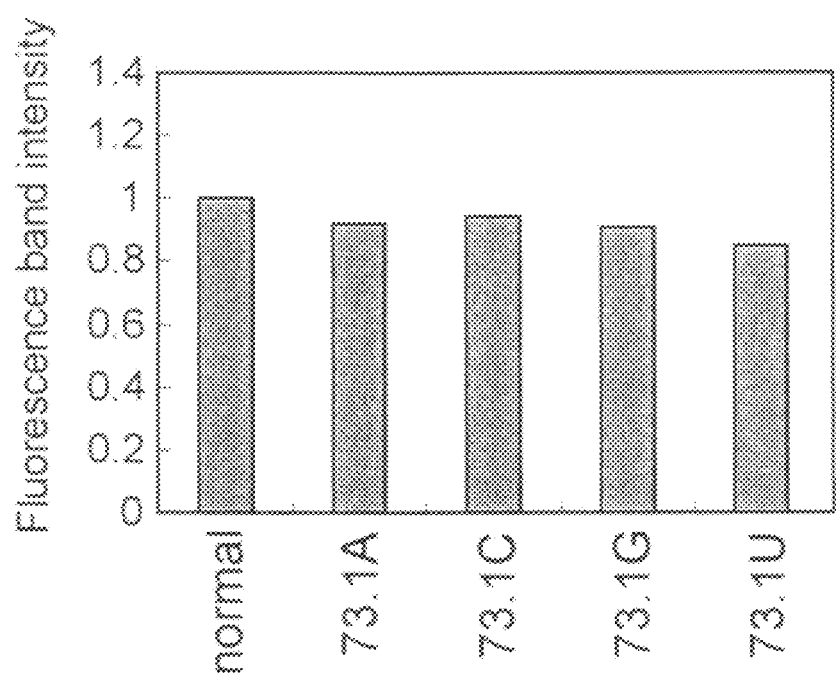

FIG. 15B shows an outline of a method for double introduction of fluorescent-labeled amino acids into maltose binding protein (MBP) based on the 4-base codon method and a stop codon method with the use of the mutant tRNA of the present invention. FIG. 15B shows the results of double introduction of fluorescent-labeled amino acids into maltose binding protein (MBP) based on the 4-base codon method and a stop codon method with the use of the mutant tRNA of the present invention. A *Mycoplasma capricolum*-derived mutant tRNA (a G1-C72, A73 mutant) was able to introduce fluorescent-labeled amino acids exclusively into the gene having UAG. In addition, the introduction efficiency was also equivalent to that in the case of 4-base codon GGGU. Accordingly, it was found that a combination of CGGG and UAG is also effective for introduction of two types of fluorescent-labeled amino acids.

The mRNA sequence of a maltose binding protein having CGGG at the N terminal portion and UAG at the C terminal portion is shown below (SEQ ID NO: 35). The sequence ranges from a start codon to the original stop codon. The underlined portion corresponds to the inserted codon.

AUGGCUAGCAUGACUGGUGGACAGCAAAUGGGUACUCGGGAGUAACGA

AUUCAAAAUCGAAGAAGGUAAACUGGUAAUCUGGAUUAACGGCGAUAA

AGGCUAUAACGGUCUCGCUGAAGUCGGUAAGAAAUUCGAGAAAGAUAC

CGGAAUUAAAGUCACCGUUGAGCAUCCGGAUAAACUGGAAGAGAAAUU

CCCACAGGUUGCGGCAACUGGCGAUGGCCCUGACAUUAUCUUCUGGGC

ACACGACCGCUUUGGUGGCUACGCUCAAUCUGGCCUGUUGGCUGAAAU

CACCCCGGACAAAGCGUUCCAGGACAAGCUGUAUCCGUUUACCUGGGA

UGCCGUACGUUACAACGGCAAGCUGAUUGCUUACCCGAUCGCUGUUGA

AGCGUUAUCGCUGAUUUAUAACAAAGAUCUGCUGCCGAACCCGCCAAA

AACCUGGGAAGAGAUCCCGGCGCUGGAUAAAGAACUGAAAGCGAAAGG

UAAGAGCGCGCUGAUGUUCAACCUGCAAGAACCGUACUUCACCUGGCC

GCUGAUUGCUGCUGACGGGGGUUAUGCGUUCAAGUAUGAAAACGGCAA

GUACGACAUUAAAGACGUGGGCGUGGAUAACGCUGGCGCGAAAGCGGG

UCUGACCUUCCUGGUUGACCUGAUUAAAAACAAACACAUGAAUGCAGA

CACCGAUUACUCCAUCGCAGAAGCUGCCUUUAAUAAAGGCGAAACAGC

GAUGACCAUCAACGGCCCGUGGGCAUGGUCCAACAUCGACACCAGCAA

AGUGAAUUAUGGUGUAACGGUACUGCCGACCUUCAAGGGUCAACCAUC

CAAACCGUUCGUUGGCGUGCUGAGCGCAGGUAUUAACGCCGCCAGUCC

GAACAAAGAGCUGGCAAAAGAGUUCCUCGAAAACUAUCUGCUGACUGA

UGAAGGUCUGGAAGCGGUUAAUAAAGACAAACCGCUGGGUGCCGUAGC

GCUGAAGUCUUACGAGGAAGAGUUGGCGAAAGAUCCACGUAUUGCCGC

CACUAUGGAAAACGCCCAGAAAGGUGAAAUCAUGCCGAACAUCCCGCA

GAUGUCCGCUUUCUGGUAUGCCGUGCGUACUGCGGUGAUCAACGCCGC

CAGCGGUCGUCAGACUGUCGAUGAAGCCCUGAAAGACGCGCAGACUCG

UAUCACCAAGUAGCACCACCACCACCACCACUAA

EXAMPLE 7

Introduction of Fluorescent-Labeled Amino Acid Having TAMRA

Figure 19A:
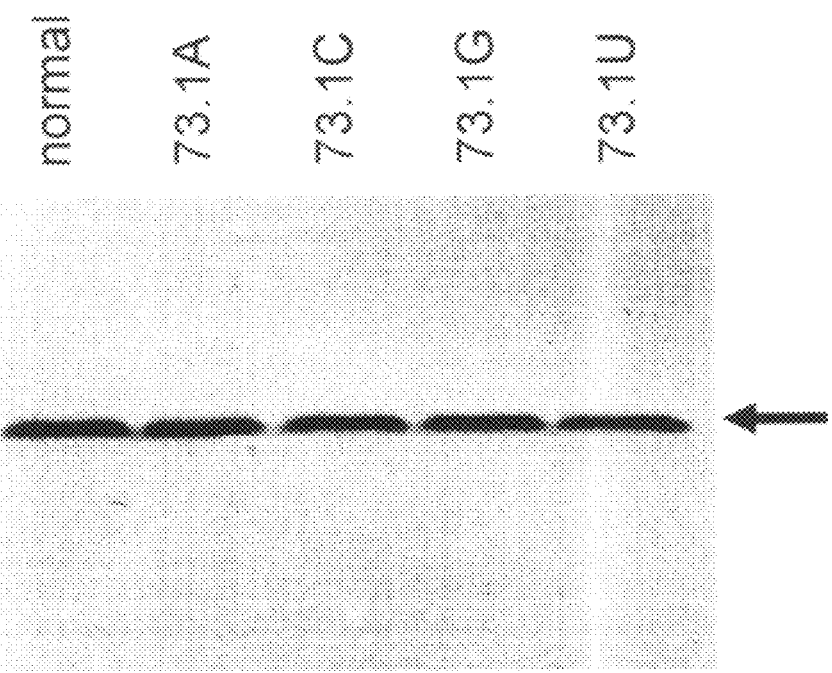
FIG. 19B is a graph showing Western blot band intensities of proteins subjected to introduction with the use of the individual mutants. The graph indicates the results of introduction of fluorescent substanceylated tyrosine with the use of a mutant tRNA for *Mycoplasma capricolum*-derived tryptophan into which a single base was inserted just before the CCA sequence at 5' end is substituted with C, and the base on the 3' side of the base substituted with C is substituted with a different base.
Figure 19B:
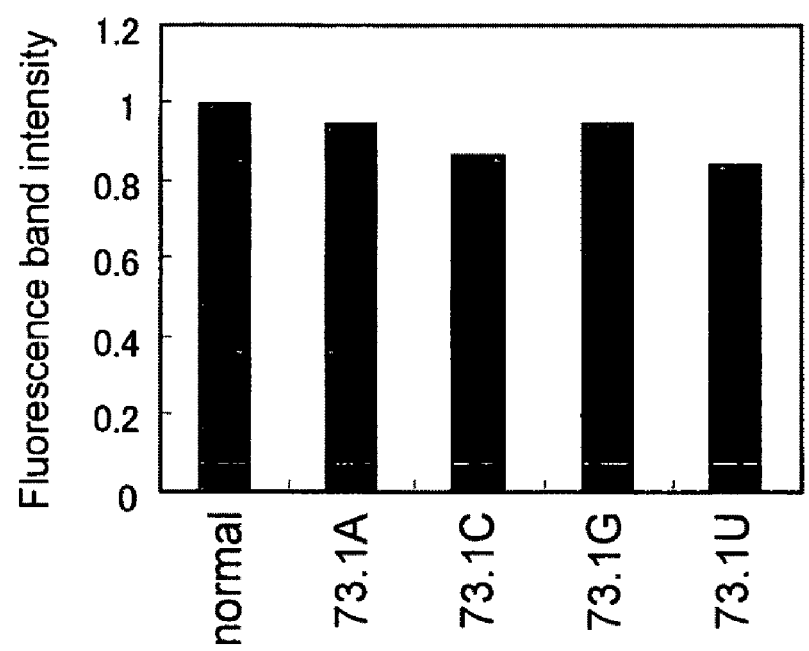

With the use of a *Mycoplasma capricolum*-derived mutant tRNA (a G1-C72, A73 mutant), TAMRA-X-aminophenylalanine-tRNA was produced by the method described in Example 1. Subsequently, streptavidin mRNA (SA2UAG) in which the 2$^{nd}$ site had been substituted with UAG was used for introduction of TAMRA-labeled amino acid by the method described in Example 2. Note that detection of fluorescence in electrophoresis gel was carried out at 532 nm excitation/605 nm detection. For comparison, introduction was carried out in a similar manner with the use of streptavidin mRNA in which the 2" site had been substituted with CGGG with the use of tRNA for yeast phenylalanine having an anticodon comprising 4 bases (CCCG). FIG. 16A shows the chemical structure of fluorescent-labeled amino acid having TAMRA (TAMRAXAF). In FIG. 16A, the portion indicated with 5 and 6 corresponds to a mixture of a substance binding to the site 5 and a substance binding to the side 6. In addition, FIG. 16B shows the results of fluorescence imaging in the case involving the use of tRNA to which fluorescent-labeled amino acid was added. Further, FIG. 16C shows fluorescence band intensities of proteins subjected to introduction. As shown in FIGS. 16B and 16C, a *Mycoplasma capricolum*-derived mutant tRNA (a G1-C72, A73 mutant) caused introduction of fluorescent-labeled amino acid having TAMRA with good efficiency, as with the case of fluorescent-labeled amino acid having BODIPY FL described in Example 4. In addition, higher levels of introduction activity were exhibited compared with the case in which introduction into a 4-base codon CGGG was carried out with the use of tRNA for yeast phenylalanine having an anticodon comprising 4 bases (CCCG).

The sequence of streptavidin mRNA in which the 2" site was substituted with UAG is shown below (SEQ ID NO: 36). The sequence ranges from a start codon to the original stop codon. The underlined part corresponds to introduced UAG.

```
AUGUAGCCGUCCAAGGACUCCAAAGCUCAGGUUUCUGCAGCCGAAGCU
GGUAUCACUGGCACCUGGUAUAACCAACUGGGGUCGACUUUCAUUGUG
ACCGCUGGUGCGGACGGAGCUCUGACUGGCACCUACGAAUCUGCGGUU
GGUAACGCAGAAUCCCGCUACGUACUGACUGGCCGUUAUGACUCUGCA
CCUGCCACCGAUGGCUCUGGUACCGCUCUGGGCUGGACUGUGGCUUGG
AAAAACAACUAGCGUAAUGCGCACAGCGCCACUACGUGGUCUGGCCAA
UACGUUGGCGGUGCUGAGGCUCGUAUCAACACUCAGUGGCUGUUAACA
UCCGGCACUACCGAAGCGAAUGCAUGGAAAUCGACACUAGUAGGUCAU
GACACCUUUACCAAAGUUAAGCCUUCUGCUGCUAGCAUUGAUGCUGCC
AAGAAAGCAGGCGUAAACAACGGUAACCCUCUAGACGCUGUUCAGCAA
CACCACCACCACCACCACUAA
```

In addition, the sequence of streptavidin mRNA sequence in which the 2$^{nd}$ site was substituted with CGGG is shown below (SEQ ID NO: 37). The sequence ranges from a start codon to a stop codon. The underlined part corresponds to introduced CGGG.

```
AUGCGGGCCGUCCAAGGACUCCAAAGCUCAGGUUUCUGCAGCCGAAGC
UGGUAUCACUGGCACCUGGUAUAACCAACUGGGGUCGACUUUCAUUGU
GACCGCUGGUGCGGACGGAGCUCUGACUGGCACCUACGAAUCUGCGGU
UGGUAACGCAGAAUCCCGCUACGUACUGACUGGCCGUUAUGACUCUGC
ACCUGCCACCGAUGGCUCUGGUACCGCUCUGGGCUGGACUGUGGCUUG
GAAAAACAACUAGCGUAAUGCGCACAGCGCCACUACGUGGUCUGGCCA
AUACGUUGGCGGUGCUGAGGCUCGUAUCAACACUCAGUGGCUGUUAAC
AUCCGGCACUACCGAAGCGAAUGCAUGGAAAUCGACACUAGUAGGUCA
UGACACCUUUACCAAAGUUAAGCCUUCUGCUGCUAGCAUUGAUGCUGC
CAAGAAAGCAGGCGUAAACAACGGUAACCCUCUAGACGCUGUUCAGCA
ACACCACCACCACCACCACUAA
```

EXAMPLE 8

Introduction of Unnatural Amino Acid with the Use of a Mutant tRNA into which a Single Base has been Inserted Just Before the CCA Sequence at the 3' End (1) Mutant tRNA for *Mycoplasma capricolum*-Derived Tryptophan A mutant tRNA (G1-C72, A73) for *Mycoplasma capricolum*-derived tryptophan into which a single base (A, C, G, or U) had been inserted just before the CCA sequence at the 3' end was produced by the method described in Example 1. In the present invention, such mutant tRNA is referred to as single-base-extended tRNA in some cases. For instance, a mutant tRNA (G1-C72, A73) for *Mycoplasma capricolum*-derived tryptophan into which A, C, G, or U has been inserted just before the CCA sequence at the 3' end is referred to as single-base-extended MycW tRNA in some cases. Subsequently, the introduction of fluorescent-labeled amino acid was evaluated by the method described in Example 2. FIG. 17 shows the structures of the mutant tRNAs used (SEQ ID NOS: 1 and 38). FIG. 17 (right) shows a mutant tRNA for *Mycoplasma capricolum*-derived tryptophan into which A, C, G, or U has been inserted just before the CCA sequence at the 3' end (SEQ ID NO: 38). FIG. 18 shows the results of introduction of BFLAF into SA83UAG with the use of single-base-extended MycW. FIG. 18A shows the results of fluorescence imaging in the case involving the use of tRNA to which fluorescent-labeled amino acid was added. FIG. 18B shows fluorescence band intensities of proteins subjected to introduction with the use of the individual mutants. As shown in FIGS. 18A and 18B, tRNA into which A, C, G, or U had been inserted just before the CCA sequence at the 3' end exhibited a high level of introduction activity comparable to that of the original tRNA. In addition, this result indicates that a mutant tRNA (G1-C72, A73) for *Mycoplasma capricolum*-derived tryptophan can introduce fluorescent substanceylated tyrosine in addition to fluorescent-labeled amino acid with good efficiency.

Further, tRNA was produced by the method described in Example 1 with the use of fluorescent substanceylated tyrosine instead of fluorescent-labeled amino acid. Subsequently, the introduction of fluorescent substanceylated tyrosine was evaluated by the method described in Example 2. Note that fluorescence imaging was not carried out and Western blot using an anti-fluorescent substanceylated tyrosine antibody or an anti-T7tag antibody was exclusively carried out. FIG. 19 shows the results of introduction of fluorescent substanceylated tyrosine (pTyr) into SA2UAG with the use of single-base-extended MycW. FIG. 19A shows the results of Western blot with the use of streptavidin mRNA in which the 2" site was substituted with UAG and tRNA to which fluorescent substanceylated tyrosine was added. FIG. 19B shows Western blot band intensities of proteins subjected to introduction. As shown in FIGS. 19A and 19B, tRNA into which A, C, G, or U had been introduced just before the CCA sequence at the 3' end exhibited a high level of introduction activity comparable to that of the original tRNA.

Figure 20A:
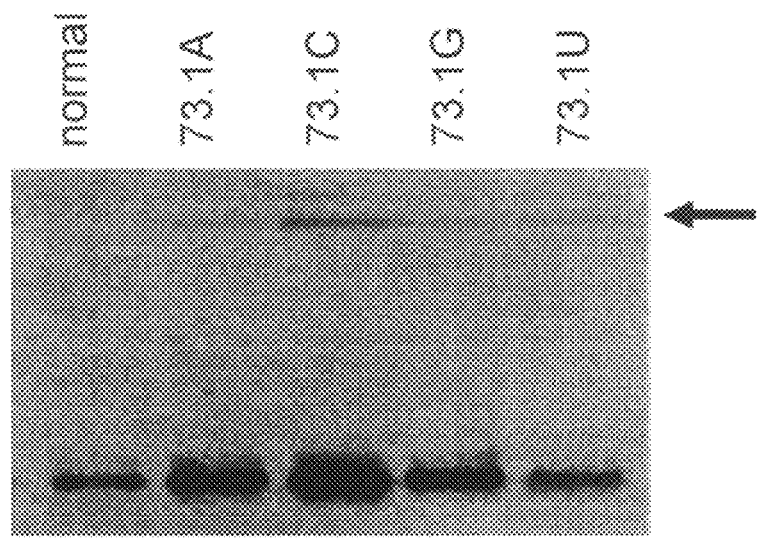
Figure 20B:
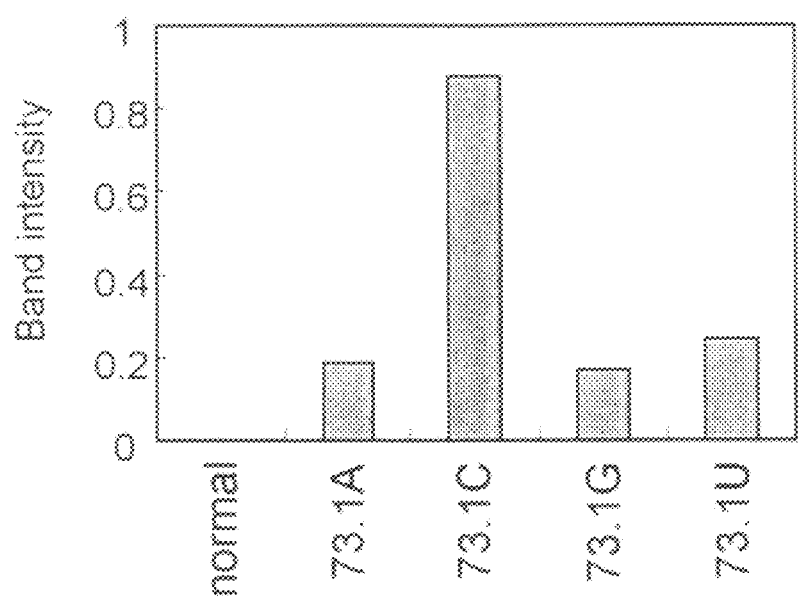

Meanwhile, FIG. 20A shows the results of Western blot with the use of streptavidin mRNA (SA83UAG) in which the 83$^{rd}$ side was substituted with UAG and tRNA to which fluorescent substanceylated tyrosine was added. FIG. 20B shows Western blot band intensities of proteins subjected to introduction. As shown in FIGS. 20A and 20B, tRNA into which A, C, G, or U had been inserted just before the CCA sequence at the 3' end exhibited a higher level of introduction activity than that of the original tRNA. In particular, good efficiency was obtained with the use of tRNA into which a single base C had been inserted.

(2) Mutant tRNA for Yeast-Derived Phenylalanine

Figure 21:
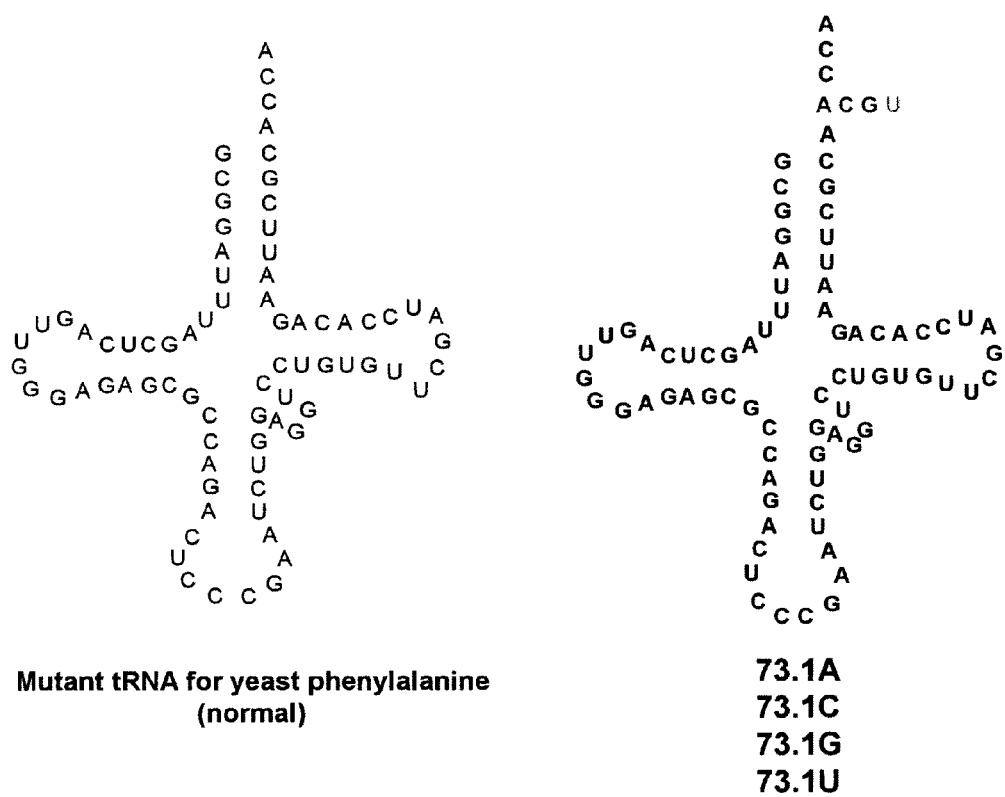
Figure 22A:
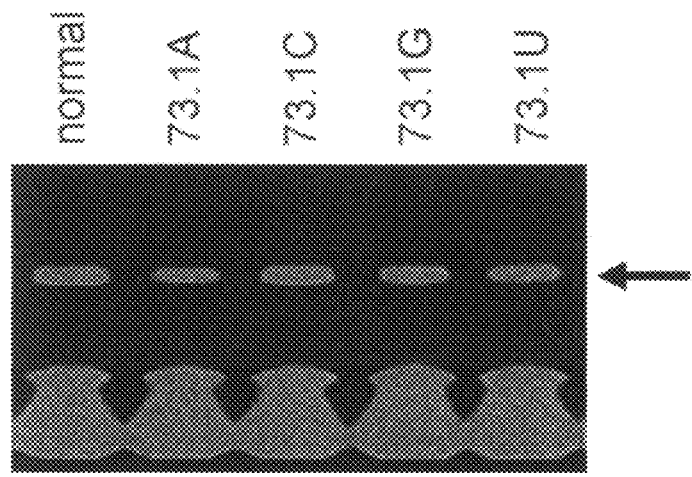
Figure 22B:
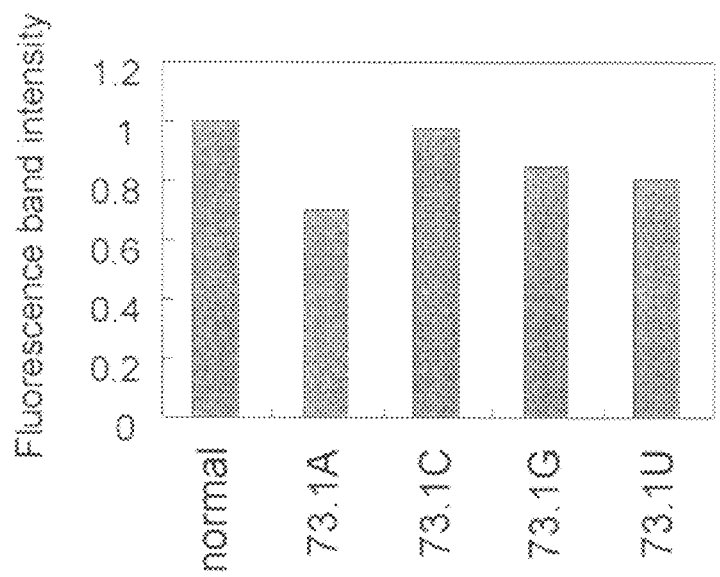

A mutant tRNA for yeast-derived phenylalanine having CCCG as an anticodon (YF(CCCG)), in which a base had been inserted or deleted at one terminal, was produced by the method described in Example 1. Subsequently, the introduction of fluorescent-labeled amino acid was evaluated by the method described in Example 2. Note that a streptavidin mRNA used contained CGGG at the Tyr83 site instead of UAG. FIG. 21 shows the structures of mutant tRNAs (SEQ ID NOS: 39 and 40). FIG. 22A shows the results of fluorescence imaging in the case involving the use of tRNA to which fluorescent-labeled amino acid was added. FIG. 22B shows the fluorescence band intensities of proteins subjected to introduction with the use of the individual mutants. As shown in FIGS. 22A and 22B, tRNA into which a single base had been inserted just before the CCA sequence at the 3' end and tRNA in which a single base located just before the CCA sequence had been removed exhibited high levels of introduction activity comparable to those of the original tRNAs.

Figure 23A:
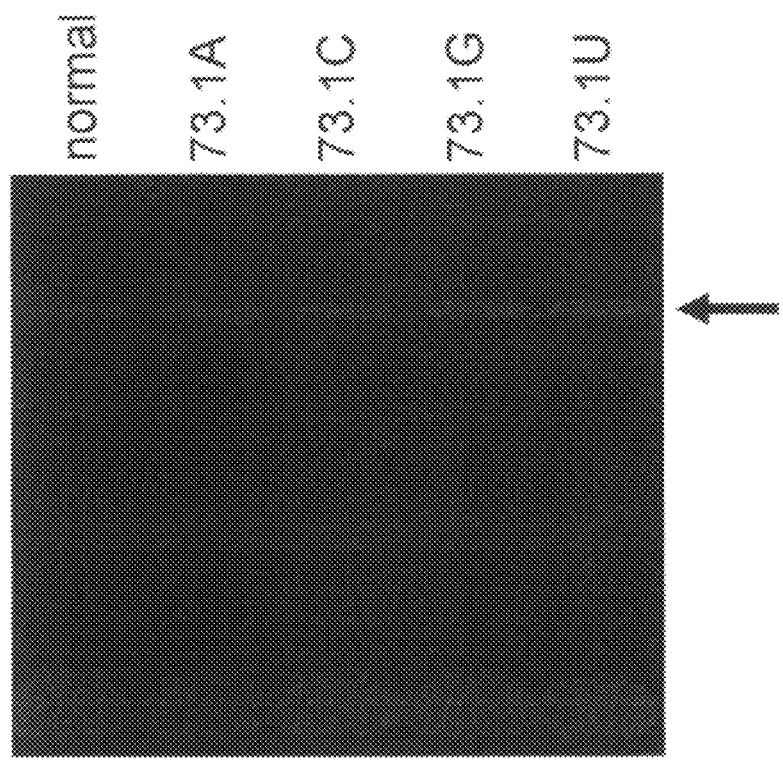
Figure 23B:
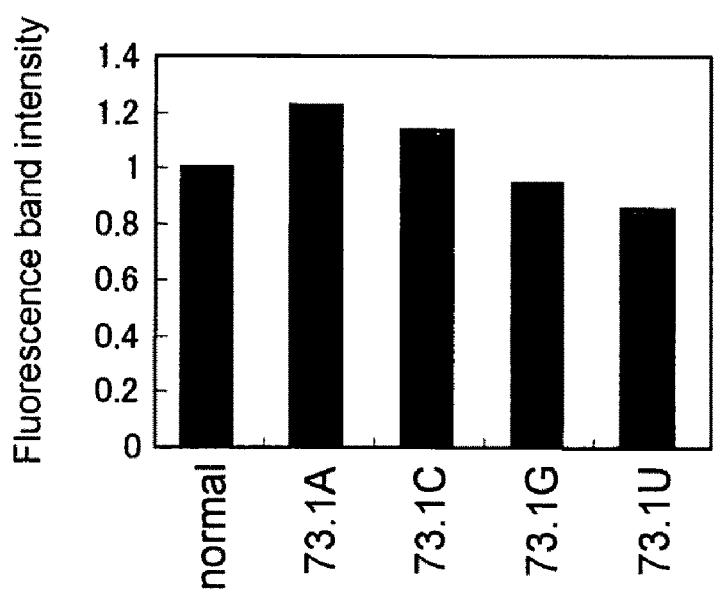

Further, with the use of streptavidin mRNA having a T7tag sequence at the N terminal into which CGGG had been inserted just after the T7tag sequence, the introduction of fluorescent-labeled amino acid was evaluated by the method described in Example 2. FIG. 23A shows the results of fluorescence imaging in the case involving the use of tRNA to which fluorescent-labeled amino acid was added. FIG. 23B shows the fluorescence band intensities of proteins subjected to introduction with the use of the individual mutants. As shown in FIGS. 23A and 23B, tRNA into which a single base had been inserted just before the CCA sequence at the 3' end exhibited a higher level of introduction activity than that of the original tRNA.

The sequence of streptavidin mRNA having a T7tag sequence at the N terminal into which CGGG has been introduced just the T7tag sequence is shown below (SEQ ID NO: 41). The sequence ranges from a start codon to a stop codon. The underlined part corresponds to the inserted CGGG codon.

```
AUGGCUAGCAUGACUGGUGGACAGCAAAUGGGUCCCCGGGAGUAACGA

AUUCCAUAUGGACCCGUCCAAGGACUCCAAAGCUCAGGUUUCUGCAGC

CGAAGCUGGUAUCACUGGCACCUGGUAUAACCAACUGGGGUCGACUUU
```

-continued
```
CAUUGUGACCGCUGGUGCGGACGGAGCUCUGACUGGCACCUACGAAUC

UGCGGUUGGUAACGCAGAAUCCCGCUACGUACUGACUGGCCGUUAUGA

CUCUGCACCUGCCACCGAUGGCUCUGGUACCGCUCUGGGCUGGACUGU

GGCUUGGAAAAACAACUAUCGUAAUGCGCACAGCGCCACUACGUGGUC

UGGCCAAUACGUUGGCGGUGCUGAGGCUCGUAUCAACACUCAGUGGCU

GUUAACAUCCGGCACUACCGAAGCGAAUGCAUGGAAAUCGACACUAGU

AGGUCAUGACACCUUUACCAAAGUUAAGCCUUCUGCUGCUAGCAUUGA

UGCUGCCAAGAAAGCAGGCGUAAACAACGGUAACCCUCUAGACGCUGU

UCAGCAACACCACCACCACCACCACUAA
```

Industrial Applicability

Functional modification and structural and functional analysis of proteins have been carried out by introducing unnatural amino acids into proteins. An example of an existing method for introducing an unnatural amino acid into a protein is a method wherein a codon located at a target site for introduction has been substituted with a stop codon UAG and translation is carried out in the presence of tRNA having an anticodon CUA and being aminoacylated with an unnatural amino acid. However, when such tRNA translates UAG, it competes with a termination factor. In the case of a conventionally used yeast Phe tRNA, such competition with a termination factor is strongly induced, resulting in a decrease in the efficiency of introduction of unnatural amino acids.

Thus, the present inventors searched for a tRNA that can introduce an unnatural amino acid into a protein with good efficiency with the use of a stop codon UAG and found such tRNA from among tRNAs derived from a variety of living species. Further, they have found tRNAs that can introduce an unnatural amino acid into a protein with good efficiency by modifying the above tRNA. With the use of such tRNAs, it becomes possible to synthesize a fluorescent-labeled protein into which a fluorescent-labeled unnatural amino acid has been introduced (WO2004/009709 A1). It also becomes possible to detect interaction of proteins and other molecules with better efficiency by introducing fluorescent-labeled unnatural amino acids, which can be a donor and an acceptor for fluorescence resonance energy transfer, into specific sites of a protein.

For instance, it becomes possible to synthesize streptavidin into which a fluorescent-labeled unnatural amino acid BODIPY FL-aminophenylalanine has been introduced into the Tyr83 site, and to introduce fluorescent-labeled unnatural amino acids, which can be a donor and an acceptor for fluorescence resonance energy transfer, into a maltose binding protein by combining the amino acids with a 4-base codon CGGG.

Amino acids to be introduced are not limited to fluorescent-labeled unnatural amino acids. Thus, the present invention can be applied to any type of amino acid or amino acid analog that can be introduced into proteins, such as hydroxy acid. In addition, since tRNA exhibits translation activity in different living species, the tRNA of the present invention is not limited to E. coli cell-free translation systems and thus can be used for translation in cells or any type of cell-free translation system derived from living species.

All publications, patents, and patent applications cited herein are incorporated herein by reference in their entirety.

The invention claimed is:

1. A mutant tRNA, which is a mutant of tRNA for tryptophan obtained from a microorganism selected from the group consisting of *Mycoplasma capricolum, Bacillus halodouranns, Bacillus subtillis, Borrelia burgdorferi, Mycoplasma genitalium, Mycoplasma pneumoniae* 1, *Mycoplasma pneumoniae* 2 and *Staphylococcus aureus* N315,
   wherein the mutation consists of;
   (i) G at the 5' end,
   (ii) C at 5th base from the 3' end which pairs with the G of (i) at the 5' end, and A at 4th base from the 3' end which is adjacent to the 3' side of the C of (ii),
   wherein the mutant tryptophan tRNA (mtRNAcuA$_{CUA}^{trp}$) pairs with a UAG codon and has CUA as an anticodon; and
   where said mtRNA$_{CUA}^{trp}$ has a higher efficiency of incorporation of an unnatural amino acid, a modified amino acid or a derivative thereof into a protein in an in-vitro cell-free translation system compared to the wild type tRNA$^{trp}$ or to a tRNA$_{CUA}^{trp}$ that does not comprise the mutations of (i), (ii) or (iii).

2. The mutant tRNA of claim 1, which consists of nucleotide sequence selected from the group consisting of SEQ ID NO:1, SEQ ID NO:2, SEQ ID NO:4, SEQ ID NO:5, SEQ ID NO:6, SEQ ID NO:18, SEQ ID NO:19, SEQ ID NO:20 and SEQ ID NO:25.

3. The mutant tRNA of claim 1 into which a single base A, C, G, or U has been inserted at the 4th position from the 3' end, which is adjacent to 5' side of ACC sequence located at 1st to 3rd position from the 3' end.

4. The mutant tRNA of claim 1, which is aminoacylated with an amino acid derivative and wherein the amino acid derivative is selected from the group consisting of hydroxy acid, mercapto acid, and carboxylic acid.

5. The mutant tRNA of claim 1, wherein the amino acid is fluorescently-labeled.

6. A method for introducing an amino acid selected from the group consisting of an unnatural amino acid, a modified amino acid, or a derivative thereof into a protein, the method comprising:

providing an mRNA of a protein into which said amino acid is introduced; the mutant tRNA of claim 1 and
allowing the mutant tRNA to pair with the UAG codon, wherein the mRNA has a UAG codon that is a codon corresponding to a site at which an amino acid is introduced thereby introducing said amino acid into the protein.

7. A method of producing a protein comprising two different phosphor amino acids in an in-vitro translation system, wherein the method comprises:
   preparing an mRNA into which a single 4-base codon and a single UAG codon have been inserted at specified positions;
   preparing two mutant tRNA molecules of claim 1 comprising anti-codons that pair with the 4-base codon and the UAG codon, and wherein one of the tRNA molecules is bound to an amino acid labeled with the fluorescent energy donor and the other tRNA is bound to an amino acid labeled with a fluorescent energy acceptor; and
   allowing the translation system to synthesize the protein wherein, the protein encoded by said mRNA displays a change in distance and orientation upon interaction with other molecules and results in a change in the efficiency of fluorescence resonance energy transfer.

8. The method of claim 6, wherein protein synthesis is carried out in a cell-free translation system.

9. The method of claim 7, wherein protein synthesis is carried out in a cell-free translation system.

10. A method for introducing an amino acid selected from the group consisting of an unnatural amino acid, a modified amino acid, or a derivative thereof into a protein, the method comprising:
    introducing an amino acid into a protein in a manner such that mRNA of a protein into which an amino acid is introduced and the mutant tRNA of claim 3 are employed; and
    allowing the mutant tRNA to pair with the UAG codon, wherein the mRNA has a UAG codon that is a codon corresponding to a site at which an amino acid is introduced.

11. A method of producing a protein comprising two different phosphor amino acids in an in-vitro translation system, wherein the method comprises preparing an mRNA into which a single 4-base codon and a single UAG codon have been inserted at specified positions;

preparing two mutant tRNA molecules of claim 3 comprising anti-codons that pair with the 4-base codon and the UAG codon, and wherein one of the tRNA molecules is bound to an amino acid labeled with the fluorescent energy donor and the other tRNA is bound to an amino acid labeled with a fluorescent energy acceptor; and allowing the translation system to synthesize the protein wherein, the protein encoded by said mRNA displays a change in distance and orientation upon interaction with other molecules and results in a change in the efficiency of fluorescence resonance energy transfer.

* * * * *